US007638297B2

(12) United States Patent
Anderson et al.

(10) Patent No.: US 7,638,297 B2
(45) Date of Patent: Dec. 29, 2009

(54) COMPOSITIONS OF ORTHOGONAL LYSYL-TRNA AND AMINOACYL-TRNA SYNTHETASE PAIRS AND USES THEREOF

(75) Inventors: J. Christopher Anderson, San Francisco, CA (US); Ning Wu, Brookline, MA (US); Stephen Santoro, Cambridge, MA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 222 days.

(21) Appl. No.: 10/563,686

(22) PCT Filed: Jul. 7, 2004

(86) PCT No.: PCT/US2004/022187

§ 371 (c)(1),
(2), (4) Date: Aug. 3, 2006

(87) PCT Pub. No.: WO2005/019415

PCT Pub. Date: Mar. 3, 2005

(65) Prior Publication Data

US 2007/0042461 A1     Feb. 22, 2007

Related U.S. Application Data

(60) Provisional application No. 60/537,149, filed on Jan. 15, 2004, provisional application No. 60/528,815, filed on Dec. 10, 2003, provisional application No. 60/485,451, filed on Jul. 7, 2003.

(51) Int. Cl.
C12P 21/06       (2006.01)
C07H 21/04       (2006.01)
C12N 9/10        (2006.01)

(52) U.S. Cl. .................. 435/69.1; 435/193; 435/252.33; 435/488

(58) Field of Classification Search .................. None
See application file for complete search history.

(56) References Cited

U.S. PATENT DOCUMENTS 7,045,337 B2    5/2006   Schultz et al.
7,083,970 B2    8/2006   Schultz et al.

FOREIGN PATENT DOCUMENTS

WO    WO 02/085923 A2    10/2002

OTHER PUBLICATIONS

Bednar et al. (1991) "Introduction of unnatural amino acids into chalcone isomerase," *Bioconjuq. Chem.*, 2(4):211-216.
Anderson (Aug. 2003) "Pathway engineering of the expanding genetic code." Thesis presented for the degree of Doctor of Philosophy in Chemistry, The Scripps Research Institute, La Jolla, CA. Call No. QD1000. A63 (2003);UMI Publication No. 3111397.
Anderson and Schultz (2003) "Adaptation of an Orthogonal Archaeal Leucyl-tRNA and Synthetase Pair for Four-base, Amber, and Opal Suppression." *Biochemistry*, 42: 9598-9608.
Anderson et al. (2004) "An expanding genetic code with a functional quadruplet codon." *Proceedings of the National Academy of Sciences, USA*, 101(20): 7566-7571.
Anderson et al. (2002) "Exploring the limits of codon and anticodon size." *Chemistry & Biology*, 9: 237-244.
Bossi and Roth (1981) "Four-base codons ACCA, ACCU and ACCC are recognized by frameshift suppressor sufJ." *Cell*, 25(2): 489-496.
Chen et al. (1994) "Properties of the lysyl-tRNA synthetase gene and product from the extreme thermophile *Thermus thermophilus*." *Journal of Bacteriology*, 176(9): 2699-2705.
Chin and Schultz (2002) "In Vivo Photocrosslinking with Unnatural Amino Acid Mutagenesis." *ChemBioChem*, 3(11): 1135-1137.
Chin et al. (2003) "An expanded eukaryotic genetic code." *Science*. 301: 964-967.
Chin et al. (2002) "Addition of a photocrosslinking amino acid to the genetic code of *Escherichia coli.*" *Proceedings of the National Academy of Sciences, USA*, 99(17): 11020-11024.
Curran and Yarus (1987) "Reading frame selection and transfer RNA anticodon loop stacking." *Science*, 238: 1545-1550.
Furter (1998) "Expansion of the genetic code: Site-directed p-fluorophenylalanine incorporation in *Escherichia coli.*" *Protein Science*, 7(2): 419-426.
Hohsaka and Sisido (2002) "Incorporation of non-natural amino acids into proteins." *Current Opinion in Chemical Biology*, 6: 809-815.
Hohsaka et al., (1999) "Incorporation of two nonnatural amino acids into proteins through extension of the genetic code." *Nucleic Acids Symposium Series*, 42: 79-80.
Hohsaka et al. (2001) "Five-base codons for incorporation of non-natural amino acids into proteins." *Nucleic Acids Research*, 29(17): 3646-3651.
Hou et al., (1992) "Novel transfer RNAs that are active in *Escherichia coli.*" *Biochemistry*, 31: 4157-4160.
Ibba et al. (1999) "Substrate recognition by class I lysyl-tRNA synthetases: a molecular basis for gene displacement." *Proceedings of the National Academy of Sciences, USA*, 96(2): 418-423.
Kobayashi et al. (2003) "Structural basis for orthogonal tRNA specific of tyrosyl-tRNA synthetases for genetic code expansion." *Nature Structural Biology*, 10(6): 425-432.
Kwok and Wong (1980) "Evolutionary relationship between *Halobacterium cutirubrum* and eukaryotes determined by use of aminoacyl-tRNA synthetases as phylogenetic probes." *Canadian Journal of Biochemistry*, 58: 213-218.
Magliery et al. (2001) "Expanding the genetic code: selection of efficient suppressors of four-base codons and identification of "shifty" four-base codons with a library approach in *Escherichia coli.*" *Journal of Molecular Biology*, 307: 755-769.

(Continued)

*Primary Examiner*—Anand U Desai
*Assistant Examiner*—Kagnew H Gebreyesus
(74) *Attorney, Agent, or Firm*—Quine Intellectual Property Law Group; Gary Baker

(57) ABSTRACT

Compositions and methods of producing components of protein biosynthetic machinery that include orthogonal lysyl-tRNAs, orthogonal lysyl-aminoacyl-tRNA synthetases, and orthogonal pairs of lysyl-tRNAs/synthetases, which incorporate homoglutamines into proteins are provided in response to a four base codon. Methods for identifying these orthogonal pairs are also provided along with methods of producing proteins with homoglutamines using these orthogonal pairs.

15 Claims, 9 Drawing Sheets

OTHER PUBLICATIONS

Mehl et al. (2003) "Generation of a bacterium with a 21 amino acid genetic code." *Journal of the American Chemistry Society*, 125: 935-939.

O'Connor (2002) "Insertions in the anticodon loop of tRNA(1)(Gln)(sufG) and tRNA(Lys) promote quadruplet decoding of CAAA." *Nucleic Acids Research*, 30(9): 1985-1990.

Santoro et al. (2003) "An archaebacteria-derived glutamyl-tRNA synthetase and tRNA pair for unnatural amino acid mutagenesis of proteins in *Escherichia coli*." *Nucleic Acids Research*, 31(23): 6700-6709.

Santoro et al. (2002) "An efficient system for the evolution of aminoacyl-tRNA synthetase specificity." *Nature Biotechnology*, 20:1044-1048.

Terada et al. (2002) "Functional convergence of two lysyl-tRNA synthetases with unrelated topologies." *Nature Structural Biology*, 9(4): 257-262.

Wang et al. (2000) "A New Functional Suppressor tRNA/Aminoacyl-tRNA Synthetase Pair for the in Vivo Incorporation of Unnatural Amino Acids into Proteins." *Journal of the American Chemistry Society*, 122: 5010-5011.

Wang et al. (2001) "Expanding the genetic code." *Science*, 292: 498-500.

Wang et al. (2003) "Addition of the keto functional group to the genetic code of *Escherichia coli*." *Proceedings of the National Academy of Sciences*, USA, 100: 56-61.

Yarus et al. (1986) "Actions of the anticodon arm in translation on the phenotypes of RNA mutants." *Journal of Molecular Biology*, 192(2): 235-255.

Ambrogelly et al. (2002) "Functional Annotation of Class I Lysyl-tRNA Synthetae Phylogeny Indicated a Limited Role for Gene Transfer." *Journal of Bacteriology*, 184(16): 4594-4600.

Cropp and Schultz (2004) "An Expanding Genetic Cods." *TRENDS on Genetics*, 20(17): 625-630.

Kawarabayasi et al. (1998) "Complete Sequence and Gene Organization of the Genome of a Hyper-thermophilic Archaebacterium, *Pryococcus horikoshii* 0T3." *DNA Research*, 5: 55-76.

Mejlhelde et al. (2001) "Adding new meanings to the genetic code." *Nature Biotechnology*, 19(6): 532-533.

Database Accession No. 057963; Abstract XP-002470658, Aug. 1, 1998.

SEQUENCE LISTING

<160> NUMBER OF SEQ ID NOS: 37

<210> SEQ ID NO 1
<211> LENGTH: 78
<212> TYPE: RNA
<213> ORGANISM: Pyrococcus abyssi

<400> SEQUENCE: 1
gggccgguag cuuagccugg uuagagcggc ggacucuuaa uccgcaggcu gggggguucaa    60 auccccccg gccgcca    78

<210> SEQ ID NO 2
<211> LENGTH: 78
<212> TYPE: RNA
<213> ORGANISM: Pyrococcus furiosus -continued

<400> SEQUENCE: 2
gggccgguag cuuagccugg uuagagcggc ggacucuuaa uccgcagguc gggdgguucaa    60 aucccccccg gcccgcca    78

<210> SEQ ID NO 3
<211> LENGTH: 78
<212> TYPE: RNA
<213> ORGANISM: Pyrococcus horikoshii

<400> SEQUENCE: 3
gggccgguag cuuagccugg uuagagcggc ggacucuuaa uccgcagguc gggdgguucaa    60 aucccccccg gcccgcca    78

<210> SEQ ID NO 4
<211> LENGTH: 78
<212> TYPE: RNA
<213> ORGANISM: Pyrococcus abyssi

<400> SEQUENCE: 4
gggccgguag cucagccugg ucagagcacc gggcuuuuaa cccggugguc gcggguucaa    60
aucccgcccg gcccgcca    78

<210> SEQ ID NO 5
<211> LENGTH: 78
<212> TYPE: RNA
<213> ORGANISM: Pyrococcus horikoshii

<400> SEQUENCE: 5
gggccgguag cucagccugg ucagagcacc gggcuuuuaa cccggugguc gcggguucaa    60
aucccgcccg gcccgcca    78

<210> SEQ ID NO 6
<211> LENGTH: 78
<212> TYPE: RNA
<213> ORGANISM: Pyrococcus furiosus

<400> SEQUENCE: 6
gggccgguag cucagccugg uuagagcacc gggcuuuuaa cccggugguc gcggguucaa    60
aucccgcccg gcccgcca    78

<210> SEQ ID NO 7
<211> LENGTH: 78
<212> TYPE: RNA
<213> ORGANISM: Pyrobaculum aerophilum

<400> SEQUENCE: 7
gggcccguag cucagcccgg uuagagcggc gggcuuuuaa cccguagguc gugdgguucga    60 aucccaccgg gcccgcca    78

<210> SEQ ID NO 8
<211> LENGTH: 77
<212> TYPE: RNA
<213> ORGANISM: Thermoplasma acidophilum

<400> SEQUENCE: 8
ggguccguag cuuagcuagg uagagcgaug gacucuuaau ccauagguca ggggguccaaa    60 uccccucgga cccgcca    77

<210> SEQ ID NO 9
<211> LENGTH: 77
<212> TYPE: RNA
<213> ORGANISM: Thermoplasma volcanium

<400> SEQUENCE: 9
ggguccguag cuuagcuagg uagagcgaug gacucuuaau ccauagguca gggguccaaa    60
uccccucgga cccgcca                                                  77

<210> SEQ ID NO 10
<211> LENGTH: 77
<212> TYPE: RNA
<213> ORGANISM: Archaeoglobus fulgidus

<400> SEQUENCE: 10
gggccgguag cuuagccagg cagagcgcgg gacucuuaau cccgcagucg gggguucaaa    60
ucccucccgg cccgcca                                                  77

<210> SEQ ID NO 11
<211> LENGTH: 77
<212> TYPE: RNA
<213> ORGANISM: Halobacterium sp. NRC-1

<400> SEQUENCE: 11
gggccgguag cucagucugg cagagcgacg gacucuuaau ccgucggucg cguguucaaa    60
ucgcgcccgg cccgcca                                                  77

<210> SEQ ID NO 12
<211> LENGTH: 77
<212> TYPE: RNA
<213> ORGANISM: Thermoplasma acidophilum

<400> SEQUENCE: 12
gggcccguag cucagccagg uagagcaucu ggcuuuuaac caggugguca gggguucgaa    60
cccccucggg cccgcca                                                  77

<210> SEQ ID NO 13
<211> LENGTH: 77
<212> TYPE: RNA
<213> ORGANISM: Thermoplasma volcanium

<400> SEQUENCE: 13
gggcccguag cucagccagg uagagcaucu ggcuuuuaac caggugguca gggguucgaa    60
cccccucggg cccgcca                                                  77

<210> SEQ ID NO 14
<211> LENGTH: 77
<212> TYPE: RNA
<213> ORGANISM: Methanococcus jannaschii

<400> SEQUENCE: 14
gggcccguag cucagucugg cagagcgccu ggcuuuuaac caggugguog aggguucaaa    60 ucccuucggg cccgcca                                                  77

<210> SEQ ID NO 15
<211> LENGTH: 77
<212> TYPE: RNA
<213> ORGANISM: Methanobacterium thermoautotrophicum

<400> SEQUENCE: 15
gggcccguag cucagucugg cagagcgcuu ggcuuuuaac caaguggucg cggguucaau    60
ucccgucggg cccgcca                                                  77

<210> SEQ ID NO 16
<211> LENGTH: 77
<212> TYPE: RNA
<213> ORGANISM: Methanosarcina mazeii

<400> SEQUENCE: 16
gggcccguag cuuagucugg uagagcgccu gacuuuuaau caggcggucg aggguucgaa    60
ucccuucggg cccgcca                                                  77

<210> SEQ ID NO 17
<211> LENGTH: 77
<212> TYPE: RNA
<213> ORGANISM: Sulfolobus tokodaii

<400> SEQUENCE: 17
gggcccguag cucagccagg uagagcggcg ggcucuuaac ccguaggucc cggguucaaa    60
ucccggcggg cccgcca                                                  77

<210> SEQ ID NO 18
<211> LENGTH: 77
<212> TYPE: RNA
<213> ORGANISM: Sulfolobus tokodaii

<400> SEQUENCE: 18
gggcccguag cucagccagg uagagcggcg ggcuuuuaac ccguaggucc cggguucaaa    60
ucccggcggg cccgcca                                                  77

<210> SEQ ID NO 19
<211> LENGTH: 77
<212> TYPE: RNA
<213> ORGANISM: Pyrobaculum aerophilum

<400> SEQUENCE: 19
gggcccguag cucagccugg uagagcggcg ggcucuuaac ccguaggucg uggguucgaa    60
ucccaccggg cccgcca                                                  77

<210> SEQ ID NO 20
<211> LENGTH: 77
<212> TYPE: RNA
<213> ORGANISM: Archaeoglobus fulgidus

<400> SEQUENCE: 20
gggcucguag cucagccagg cagagcgacg ggcuuuuaac ccgucggucg cggguucaaa    60
ucccgucgag cccgcca                                                  77

<210> SEQ ID NO 21
<211> LENGTH: 76
<212> TYPE: RNA
<213> ORGANISM: Sulfolobus solfataricus

<400> SEQUENCE: 21
gggcccguag cuuagccagg uagagcgacg ggcucuuaac ccguagucccc ggguucgaau   60 cccggcgggc ccgcca                                                   76

<210> SEQ ID NO 22
<211> LENGTH: 79
<212> TYPE: RNA
<213> ORGANISM: Aeropyrum pernix

<400> SEQUENCE: 22
gggcccguag cucagccugg uagagcggcg ggcucuuacc ccgcggaagu cccggguuca    60
aaucccggcg ggcccgcca                                                 79

<210> SEQ ID NO 23
<211> LENGTH: 80
<212> TYPE: RNA
<213> ORGANISM: Artificial
<220> FEATURE:
<223> OTHER INFORMATION: consensus tRNA
<220> FEATURE:
<221> NAME/KEY: misc_feature
<222> LOCATION: (36)..(36)
<223> OTHER INFORMATION: n indicates no consensus (u or c)
<220> FEATURE:
<221> NAME/KEY: misc_feature
<222> LOCATION: (43)..(43)
<223> OTHER INFORMATION: n indicates no consensus (gap or c)
<220> FEATURE:
<221> NAME/KEY: misc_feature
<222> LOCATION: (44)..(44)
<223> OTHER INFORMATION: n indicates no consensus (gap or g)

<400> SEQUENCE: 23
gggcccguag cucagccugg uuagagcggc gggcunuuaa ccnncggagg ucgcggguuc    60
aaaucccgcc gggcccgcca                                                80

<210> SEQ ID NO 24
<211> LENGTH: 77
<212> TYPE: RNA
<213> ORGANISM: Artificial
<220> FEATURE:
<223> OTHER INFORMATION: consensus-derived tRNA AKCUA

<400> SEQUENCE: 24
gggcccguag cucagccugg uagagcggcg ggcucuaaac ccgcaggucg cggguucaaa    60
ucccgccggg cccgcca                                                   77

<210> SEQ ID NO 25
<211> LENGTH: 78
<212> TYPE: RNA
<213> ORGANISM: Artificial
<220> FEATURE:
<223> OTHER INFORMATION: consensus-derived tRNA library
<220> FEATURE:
<221> NAME/KEY: misc_feature
<222> LOCATION: (1)..(4)
<223> OTHER INFORMATION: n is a, c, g or u
<220> FEATURE:
<221> NAME/KEY: misc_feature
<222> LOCATION: (71)..(74)
<223> OTHER INFORMATION: n is a, c, g or u

<400> SEQUENCE: 25
nnnnccguag cucagccugg uagagcggcg ggcuuccuaa cccgcagguc gcggguucaa    60
aucccgccgg nnnngcca                                                  78

<210> SEQ ID NO 26
<211> LENGTH: 78
<212> TYPE: RNA
<213> ORGANISM: Artificial

-continued

```
<220> FEATURE:
<223> OTHER INFORMATION: mutant tRNA

<400> SEQUENCE: 26
ugguccguag cucagccugg uagagcggcg ggcuuccuca cccgcagguc gcggguucaa    60
aucccgccgg acuagcca                                                  78

<210> SEQ ID NO 27
<211> LENGTH: 1092
<212> TYPE: DNA
<213> ORGANISM: Artificial
<220> FEATURE:
<223> OTHER INFORMATION: mutant tRNA synthetase

<400> SEQUENCE: 27
atggttcatt gggccgatta tattgctgat aaaataatta gagagagggg ggagaaggag    60
aagtacgttg ttgagagtgg aataacgcca agtggttacg ttcacgttgg aactttagg    120 gagctttta cagcttatat tgtgggccat gccctaaggg ataagggta tgaggttagg    180 cacatccaca tgtgggatga ttatgataga tttaggaagg ttccaaggaa cgttccccag    240
gaatggaaag attacctggg aatgcccatt agtgaagttc ctgatccctg gggatgccat    300
gagagttatg ctgaacactt catgagaaag ttcgaggagg aggtagaaaa attagggatc    360
gaagttgact ttctttatgc gagtgaactc tacaagagag gggaatattc tgaggagata    420
aggttagcct ttgagaaaag ggataagata atggagatac taaacaagta tagggaaatt    480
gcgaaacaac ctcccttcc agagaactgg tggcccgcaa tggtttactg ccctgagcat    540
aggagggaag cagagatcat tgaatgggat ggggctgga aggttaagta taagtgcccc    600
gaaggtcacg agggatgggt tgatataagg agtgggaacg tgaaactgag gtggcgtgtt    660
gattggccca tgcgttggtc tcactttggc gttgacttcg aacctgctgg aaaggatcat    720
cttgtggctg gttcaagcta cgatacggga aaggagatta taaggaagt ttatggaaag    780 gaagctccgt tatctttaat gtatgagttt gttggaatta gggggcagaa ggggaagatg    840
agtggtagta agggaaatgt tatttactc agcgatctgt atgaggttct tgagccaggt    900
ctcgttagat ttatctacgc tcggcatagg ccaaacaagg agataaagat agatctaggt    960
cttggcattc taaacctcta cgatgagttc gataaagttg agagaatata cttcgggttt   1020
gagggtggta aggtgatga tgaagaatta aggaggactt acgagctttc ggtgatgctg   1080
ccaacttact ga                                                      1092

<210> SEQ ID NO 28
<211> LENGTH: 363
<212> TYPE: PRT
<213> ORGANISM: Artificial
<220> FEATURE:
<223> OTHER INFORMATION: mutant tRNA synthetase

<400> SEQUENCE: 28

Met Val His Trp Ala Asp Tyr Ile Ala Asp Lys Ile Ile Arg Glu Arg
1               5                   10                  15

Gly Glu Lys Glu Lys Tyr Val Val Glu Ser Gly Ile Thr Pro Ser Gly
            20                  25                  30

Tyr Val His Val Gly Asn Phe Arg Glu Leu Phe Thr Ala Tyr Ile Val
        35                  40                  45

Gly His Ala Leu Arg Asp Lys Gly Tyr Glu Val Arg His Ile His Met
    50                  55                  60
```

```
Trp Asp Asp Tyr Asp Arg Phe Arg Lys Val Pro Arg Asn Val Pro Gln
 65                  70                  75                  80

Glu Trp Lys Asp Tyr Leu Gly Met Pro Ile Ser Glu Val Pro Asp Pro
                 85                  90                  95

Trp Gly Cys His Glu Ser Tyr Ala Glu His Phe Met Arg Lys Phe Glu
            100                 105                 110

Glu Glu Val Glu Lys Leu Gly Ile Glu Val Asp Phe Leu Tyr Ala Ser
        115                 120                 125

Glu Leu Tyr Lys Arg Gly Glu Tyr Ser Glu Glu Ile Arg Leu Ala Phe
    130                 135                 140

Glu Lys Arg Asp Lys Ile Met Glu Ile Leu Asn Lys Tyr Arg Glu Ile
145                 150                 155                 160

Ala Lys Gln Pro Pro Leu Pro Glu Asn Trp Trp Pro Ala Met Val Tyr
                165                 170                 175

Cys Pro Glu His Arg Arg Glu Ala Glu Ile Ile Glu Trp Asp Gly Gly
            180                 185                 190

Trp Lys Val Lys Tyr Lys Cys Pro Glu Gly His Glu Gly Trp Val Asp
        195                 200                 205

Ile Arg Ser Gly Asn Val Lys Leu Arg Trp Arg Val Asp Trp Pro Met
    210                 215                 220

Arg Trp Ser His Phe Gly Val Asp Phe Glu Pro Ala Gly Lys Asp His
225                 230                 235                 240

Leu Val Ala Gly Ser Ser Tyr Asp Thr Gly Lys Glu Ile Ile Lys Glu
                245                 250                 255

Val Tyr Gly Lys Glu Ala Pro Leu Ser Leu Met Tyr Glu Phe Val Gly
            260                 265                 270

Ile Lys Gly Gln Lys Gly Lys Met Ser Gly Ser Lys Gly Asn Val Ile
        275                 280                 285

Leu Leu Ser Asp Leu Tyr Glu Val Leu Glu Pro Gly Leu Val Arg Phe
    290                 295                 300

Ile Tyr Ala Arg His Arg Pro Asn Lys Glu Ile Lys Ile Asp Leu Gly
305                 310                 315                 320

Leu Gly Ile Leu Asn Leu Tyr Asp Glu Phe Asp Lys Val Glu Arg Ile
                325                 330                 335

Tyr Phe Gly Val Glu Gly Gly Lys Gly Asp Asp Glu Glu Leu Arg Arg
            340                 345                 350

Thr Tyr Glu Leu Ser Val Met Leu Pro Thr Tyr
        355                 360

<210> SEQ ID NO 29
<211> LENGTH: 1572
<212> TYPE: DNA
<213> ORGANISM: Artificial
<220> FEATURE:
<223> OTHER INFORMATION: mutant tRNA synthetase

<400> SEQUENCE: 29
atggttcatt gggccgatta tattgctgat aaaataatta gagagagggg ggagaaggag      60
aagtacgttg ttgagagtgg aataacgcca agtggttacg ttcacgttgg gaactttagg     120
gagcttttta cagcttatat tgtgggccat gccctaaggg ataaggggta tgaggttagg     180
cacatccaca tgtgggatga ttatgataga tttaggaagg ttccaaggaa cgttccccag     240
gaatggaaag attacctggg aatgcccatt agtgaagttc ctgatccctg ggatgccat      300 gagagttatg ctgaacactt catgagaaag ttcgaggagg aggtagaaaa attagggatc     360
```

-continued

```
gaagttgact ttctttatgc gagtgaactc tacaagagag gggaatattc tgaggagata     420
aggttagcct ttgagaaaag ggataagata atggagatac taaacaagta tagggaaatt     480
gcgaaacaac ctccccttcc agagaactgg tggcccgcaa tggtttactg ccctgagcat     540
aggagggaag cagagatcat tgaatgggat ggggctgga aggttaagta taagtgcccc      600
gaaggtcacg agggatgggt tgatataagg agtgggaacg tgaaactgag gtggcgtgtt     660
gattggccca tgcgttggtc tcactttggc gttgacttcg aacctgctgg aaaggatcat     720
cttgtggctg gttcaagcta cgatacggga aaggagatta taaggaagt ttatggaaag     780 gaagctccgt tatctttaat gtatgagttt gttggaatta aggggcagaa ggggaagatg     840
agtggtagta agggaaatgt tatttactc agcgatctgt atgaggttct tgagccaggt     900
ctcgttagat ttatctacgc tcggcatagg ccaaacaagg agataaagat agatctaggt     960
cttggcattc taaacctcta cgatgagttc gataaagttg agagaatata cttcggggtt    1020
gagggtggta aggtgatga tgaagaatta aggaggactt acgagctttc aatgcctaag    1080
aagcctgaga gattagtcgc tcaagctcct tttaggttcc tagcggtgtt ggttcagtta    1140
ccgcatttaa ccgaagaaga cataataaat gttctaatca acagggaca tattcccagg    1200 gatctatcca aggaggacgt tgagagggtt aaacttagga taaaccttgc taggaattgg    1260
gttaaaaagt atgcccctga ggatgttaaa ttctcaatac ttgagaaacc tccagaagtt    1320
gaggtaagtg agatgttag ggaggccatg aatgaggttg ctgagtggct tgagaatcat    1380
gaggaattta gcgttgaaga gtttaataac attctattcg aagttgccaa gaggaggggg    1440
atatccagta gggagtggtt ttcgacgctc tacagattat ttattggaaa ggaaagggga    1500
ccgagattgg ccagtttcct ggcatctctt gataggagtt tcgttattaa acgacttaga    1560
cttgagggat ag                                                       1572
```

<210> SEQ ID NO 30
<211> LENGTH: 523
<212> TYPE: PRT
<213> ORGANISM: Artificial
<220> FEATURE:
<223> OTHER INFORMATION: mutant tRNA synthetase

<400> SEQUENCE: 30

```
Met Val His Trp Ala Asp Tyr Ile Ala Asp Lys Ile Ile Arg Glu Arg
1               5                   10                  15

Gly Glu Lys Glu Lys Tyr Val Val Glu Ser Gly Ile Thr Pro Ser Gly
                20                  25                  30

Tyr Val His Val Gly Asn Phe Arg Glu Leu Phe Thr Ala Tyr Ile Val
            35                  40                  45

Gly His Ala Leu Arg Asp Lys Gly Tyr Glu Val Arg His Ile His Met
        50                  55                  60

Trp Asp Asp Tyr Asp Arg Phe Arg Lys Val Pro Arg Asn Val Pro Gln
65                  70                  75                  80

Glu Trp Lys Asp Tyr Leu Gly Met Pro Ile Ser Glu Val Pro Asp Pro
                85                  90                  95

Trp Gly Cys His Glu Ser Tyr Ala Glu His Phe Met Arg Lys Phe Glu
            100                 105                 110

Glu Glu Val Glu Lys Leu Gly Ile Glu Val Asp Phe Leu Tyr Ala Ser
        115                 120                 125

Glu Leu Tyr Lys Arg Gly Glu Tyr Ser Glu Glu Ile Arg Leu Ala Phe
    130                 135                 140
```

Glu Lys Arg Asp Lys Ile Met Glu Ile Leu Asn Lys Tyr Arg Glu Ile
145                 150                 155                 160

Ala Lys Gln Pro Pro Leu Pro Glu Asn Trp Trp Pro Ala Met Val Tyr
                165                 170                 175

Cys Pro Glu His Arg Arg Glu Ala Glu Ile Ile Glu Trp Asp Gly Gly
            180                 185                 190

Trp Lys Val Lys Tyr Lys Cys Pro Glu Gly His Glu Gly Trp Val Asp
        195                 200                 205

Ile Arg Ser Gly Asn Val Lys Leu Arg Trp Arg Val Asp Trp Pro Met
210                 215                 220

Arg Trp Ser His Phe Gly Val Asp Phe Glu Pro Ala Gly Lys Asp His
225                 230                 235                 240

Leu Val Ala Gly Ser Ser Tyr Asp Thr Gly Lys Glu Ile Ile Lys Glu
                245                 250                 255

Val Tyr Gly Lys Glu Ala Pro Leu Ser Leu Met Tyr Glu Phe Val Gly
            260                 265                 270

Ile Lys Gly Gln Lys Gly Lys Met Ser Gly Ser Lys Gly Asn Val Ile
        275                 280                 285

Leu Leu Ser Asp Leu Tyr Glu Val Leu Glu Pro Gly Leu Val Arg Phe
290                 295                 300

Ile Tyr Ala Arg His Arg Pro Asn Lys Glu Ile Lys Ile Asp Leu Gly
305                 310                 315                 320

Leu Gly Ile Leu Asn Leu Tyr Asp Glu Phe Asp Lys Val Glu Arg Ile
                325                 330                 335

Tyr Phe Gly Val Glu Gly Gly Lys Gly Asp Asp Glu Glu Leu Arg Arg
            340                 345                 350

Thr Tyr Glu Leu Ser Met Pro Lys Lys Pro Glu Arg Leu Val Ala Gln
        355                 360                 365

Ala Pro Phe Arg Phe Leu Ala Val Leu Val Gln Leu Pro His Leu Thr
370                 375                 380

Glu Glu Asp Ile Ile Asn Val Leu Ile Lys Gln Gly His Ile Pro Arg
385                 390                 395                 400

Asp Leu Ser Lys Glu Asp Val Glu Arg Val Lys Leu Arg Ile Asn Leu
                405                 410                 415

Ala Arg Asn Trp Val Lys Lys Tyr Ala Pro Glu Asp Val Lys Phe Ser
            420                 425                 430

Ile Leu Glu Lys Pro Pro Glu Val Glu Val Ser Gly Asp Val Arg Glu
        435                 440                 445

Ala Met Asn Glu Val Ala Glu Trp Leu Glu Asn His Glu Glu Phe Ser
450                 455                 460

Val Glu Glu Phe Asn Asn Ile Leu Phe Glu Val Ala Lys Arg Arg Gly
465                 470                 475                 480

Ile Ser Ser Arg Glu Trp Phe Ser Thr Leu Tyr Arg Leu Phe Ile Gly
                485                 490                 495

Lys Glu Arg Gly Pro Arg Leu Ala Ser Phe Leu Ala Ser Leu Asp Arg
            500                 505                 510

Ser Phe Val Ile Lys Arg Leu Arg Leu Glu Gly
        515                 520

<210> SEQ ID NO 31
<211> LENGTH: 4813
<212> TYPE: DNA
<213> ORGANISM: Artificial
<220> FEATURE:
<223> OTHER INFORMATION: plasmid pACKO-A184TAG

```
<220> FEATURE:
<221> NAME/KEY: misc_feature
<222> LOCATION: (3749)..(3749)
<223> OTHER INFORMATION: n is a, c, g, or t
<220> FEATURE:
<221> NAME/KEY: misc_feature
<222> LOCATION: (3769)..(3769)
<223> OTHER INFORMATION: n is a, c, g, or t

<400> SEQUENCE: 31
gaactccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttggccc agggcttccc     360
ggtatcaaca gggacaccag gatttatta ttctgcgaag tgatcttccg tcacaggtat      420
ttattcggcg caaagtgcgt cgggtgatgc tgccaactta ctgatttagt gtatgatggt     480 gttttgagg tgctccagtg gcttctgttt ctatcagctg tccctcctgt tcagctactg      540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgccccctg acaagcatca cgaaatctga cgctcaaatc      900
agtggtggcg aaacccgaca ggactataaa gataccaggc gtttcccct ggcggctccc      960 tcgtgcgctc tcctgttcct gccttcggtt taccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320 cgaaaaccg ccctgcaagg cggttttttc gttttcagag caagagatta gcgcagacc      1380 aaaacgatct caagaagatc atcttattaa tcagataaaa tatttctaga tttcagtgca     1440
atttatctct tcaaatgtag cacctgaagt cagcccata cgatataagt tgtaattctc      1500
atgtttgaca gcttatcatc gataagcttt aatgcggtag tttatcacag ttaaattgct     1560
aacgcagtca ggcaccgtgt atgaaatcta caatgcgct catcgtcatc ctcggcaccg     1620
tcaccctgga tgctgtaggc ataggcttgg ttatgccggt actgccggc ctcttgcggg      1680 atatcggttt cttagacgtc aggtggcact tttcggggaa atgtgcgcgg aaccccctatt   1740 tgtttatttt tctaaataca ttcaaatatg tatccgctca tgagacaata accctgataa    1800
atgcttcaat aatattgaaa aaggaagagt atgagtattc aacatttccg tgtcgccctt    1860 attcccttttt ttgcggcatt ttgccttcct gtttttgctc acccagaaac gctggtgaaa    1920
gtaaaagatg ctgaagatca gttgggtgca cgagtgggt acatcgaact ggatctcaac     1980
agcggtaaga tccttgagag ttttcgcccc gaagaacgtt ttccaatgat gagcactttt    2040
```

```
aaagttctgc tatgtggcgc ggtattatcc cgtgttgacg ccgggcaaga gcaactcggt    2100
cgccgcatac actattctca gaatgacttg gttgagtact caccagtcac agaaaagcat    2160
cttacggatg gcatgacagt aagagaatta tgcagtgctg ccataaccat gagtgataac    2220
actgcggcca acttacttct gacaacgatc ggaggaccga aggagctaac cgcttttttg    2280
cacaacatgg gggatcatgt aactcgcctt gatcgttggg aaccggagct gaatgaagcc    2340
ataccaaacg acgagcgtga caccacgatg ccttaggcaa tggcaacaac gttgcgcaaa    2400
ctattaactg gcgaactact tactctagct tcccggcaac aattaataga ctggatggag    2460
gcggataaag ttgcaggacc acttctgcgc tcggcccttc cggctggctg gtttattgct    2520
gataaatctg gagccggtga gcgtgggtct cgcggtatca ttgcagcact ggggccagat    2580
ggtaagccct cccgtatcgt agttatctac acgacgggga gtcaggcaac tatggatgaa    2640
cgaaatagac agatcgctga gataggtgcc tcactgatta agcattggca ccaccaccac    2700
caccactaac ccgggaccaa gtttactcat atatacttta gattgattta aaacttcatt    2760
tttaatttaa aaggatctag gtgaagatcc ttttttgataa tctcatgacc aaaatccctt    2820
aacggcatgc accattcctt gcggcggcgg tgctcaacgg cctcaaccta ctactgggct    2880
gcttcctaat gcaggagtcg cataagggag agcgtctggc gaaggggga tgtgctgcaa    2940 ggcgattaag ttgggtaacg ccagggtttt cccagtcacg acgttgtaaa acgacggcca    3000
gtgccaagct taaaaaaat ccttagcttt cgctaaggat ctgcagttat aatctctttc    3060
taattggctc taaaatcttt ataagttctt cagctacagc attttttaaa tccattggat    3120
gcaattcctt attttaaat aaactctcta actcctcata gctattaact gtcaaatctc    3180
caccaaattt ttctggcctt tttatggtta aaggatattc aaggaagtat ttagctatct    3240
ccattattgg atttccttca acaactccag ctgggcagta tgctttcttt atcttagccc    3300
taatctcttc tggagagtca tcaacagcta taaaattccc ttttgaagaa ctcatctttc    3360
cttctccatc caaacccgtt aagacagggt tgtgaataca aacaaccttt tttggtaaaa    3420
gctcccttgc taacatgtgt attttttctct gctccatccc tccaactgca acatcaacgc    3480
ctaaataatg aatatcatta acctgcatta ttggatagat aacttcagca acctttggat    3540
tttcatcctc tcttgctata agttccatac tccttcttgc tctttttaag gtagttttta    3600
aagccaatct atagacattc agtgtataat ccttatcaag ctggaattca gcgttacaag    3660
tattacacaa agttttttat gttgagaata ttttttgat ggggcgccac ttattttga    3720 tcgttcgctc aaagaagcgg cgccagggnt gttttctttt tcaccagtna gacgggcaac    3780
agaacgccat gagcggcctc atttcttatt ctgagttaca acagtccgca ccgctgtccg    3840
gtagctcctt ccggtgggcg cggggcatga ctatcgtcgc cgcacttatg actgtcttct    3900
ttatcatgca actcgtagga caggtgccgg cagcgcccaa cagtccccg gccacggggc    3960 ctgccaccat acccacgccg aaacaagcgc cctgcaccat tatgttccgg atctgcatcg    4020
caggatgctg ctggctaccc tgtggaacac ctacatctgt attaacgaag cgctaaccgt    4080
ttttatcagg ctctgggagg cagaataaat gatcatatcg tcaattatta cctccacggg    4140
gagagcctga gcaaactggc ctcaggcatt tgagaagcac acggtcacac tgcttccggt    4200
agtcaataaa ccggtaaacc agcaatagac ataagcggct atttaacgac cctgccctga    4260
accgacgacc gggtcgaatt tgctttcgaa tttctgccat tcatccgctt attatcactt    4320
attcaggcgt agcaccaggc gtttaagggc accaataact gccttaaaaa aattacgccc    4380
cgccctgcca ctcatcgcag tactgttgta attcattaag cattctgccg acatggaagc    4440
```

```
catcacagac ggcatgatga acctgaatcg ccagcggcat cagcaccttg tcgccttgcg    4500
tataatattt gcccatggtg aaaacggggg cgaagaagtt gtccatattg gccacgttta    4560
aatcaaaact ggtgaaactc acccagggat tggctgagac gaaaaacata ttctcaataa    4620
accctttagg gaataggcc aggttttcac cgtaacacgc cacatcttgc gaatatatgt    4680
gtagaaactg ccggaaatcg tcgtggtatt cactccagag cgatgaaaac gtttcagttt    4740
gctcatggaa aacggtgtaa caagggtgaa cactatccca tcaccagc tcaccgtctt    4800 tcattgccat acg                                                      4813

<210> SEQ ID NO 32
<211> LENGTH: 4814
<212> TYPE: DNA
<213> ORGANISM: Artificial
<220> FEATURE:
<223> OTHER INFORMATION: plasmid pACKO-A184AGGA
<220> FEATURE:
<221> NAME/KEY: misc_feature
<222> LOCATION: (3750)..(3750)
<223> OTHER INFORMATION: n is a, c, g, or t
<220> FEATURE:
<221> NAME/KEY: misc_feature
<222> LOCATION: (3770)..(3770)
<223> OTHER INFORMATION: n is a, c, g, or t

<400> SEQUENCE: 32
gaactccgga tgagcattca tcaggcgggc aagaatgtga ataaaggccg gataaaactt      60
gtgcttattt ttctttacgg tctttaaaaa ggccgtaata tccagctgaa cggtctggtt     120
ataggtacat tgagcaactg actgaaatgc ctcaaaatgt tctttacgat gccattggga     180
tatatcaacg gtggtatatc cagtgatttt tttctccatt ttagcttcct tagctcctga     240
aaatctcgat aactcaaaaa atacgcccgg tagtgatctt atttcattat ggtgaaagtt     300
ggaacctctt acgtgccgat caacgtctca ttttcgccaa aagttgggcc agggcttccc     360
ggtatcaaca gggacaccag gatttattta ttctgcgaag tgatcttccg tcacaggtat     420
ttattcggcg caaagtgcgt cgggtgatgc tgccaactta ctgatttagt gtatgatggt     480
gtttttgagg tgctccagtg gcttctgttt ctatcagctg tccctcctgt tcagctactg     540
acggggtggt gcgtaacggc aaaagcaccg ccggacatca gcgctagcgg agtgtatact     600
ggcttactat gttggcactg atgagggtgt cagtgaagtg cttcatgtgg caggagaaaa     660
aaggctgcac cggtgcgtca gcagaatatg tgatacagga tatattccgc ttcctcgctc     720
actgactcgc tacgctcggt cgttcgactg cggcgagcgg aaatggctta cgaacggggc     780
ggagatttcc tggaagatgc caggaagata cttaacaggg aagtgagagg gccgcggcaa     840
agccgttttt ccataggctc cgcccccctg acaagcatca cgaaatctga cgctcaaatc     900
agtggtggcg aaacccgaca ggactataaa gataccaggc gtttccccct ggcggctccc     960
tcgtgcgctc tcctgttcct gcctttcggt ttaccggtgt cattccgctg ttatggccgc    1020
gtttgtctca ttccacgcct gacactcagt tccgggtagg cagttcgctc caagctggac    1080
tgtatgcacg aaccccccgt tcagtccgac cgctgcgcct tatccggtaa ctatcgtctt    1140
gagtccaacc cggaaagaca tgcaaaagca ccactggcag cagccactgg taattgattt    1200
agaggagtta gtcttgaagt catgcgccgg ttaaggctaa actgaaagga caagttttgg    1260
tgactgcgct cctccaagcc agttacctcg gttcaaagag ttggtagctc agagaacctt    1320
cgaaaaaccg ccctgcaagg cggttttttc gttttcagag caagagatta gcgcagacc    1380 aaaacgatct caagaagatc atcttattaa tcagataaaa tatttctaga tttcagtgca    1440
```

```
atttatctct tcaaatgtag cacctgaagt cagccccata cgatataagt tgtaattctc    1500
atgtttgaca gcttatcatc gataagcttt aatgcggtag tttatcacag ttaaattgct    1560
aacgcagtca ggcaccgtgt atgaaatcta acaatgcgct catcgtcatc ctcggcaccg    1620
tcaccctgga tgctgtaggc ataggcttgg ttatgccggt actgccgggc ctcttgcggg    1680
atatcggttt cttagacgtc aggtggcact tttcggggaa atgtgcgcgg aaccccctatt    1740 tgtttatttt tctaaataca ttcaaatatg tatccgctca tgagacaata accctgataa    1800
atgcttcaat aatattgaaa aaggaagagt atgagtattc aacatttccg tgtcgccctt    1860
attccctttt ttgcggcatt ttgccttcct gtttttgctc acccagaaac gctggtgaaa    1920
gtaaaagatg ctgaagatca gttgggtgca cgagtgggtt acatcgaact ggatctcaac    1980
agcggtaaga tccttgagag ttttcgcccc gaagaacgtt ttccaatgat gagcactttt    2040
aaagttctgc tatgtggcgc ggtattatcc cgtgttgacg ccgggcaaga gcaactcggt    2100
cgccgcatac actattctca gaatgacttg gttgagtact caccagtcac agaaaagcat    2160
cttacggatg gcatgacagt aagagaatta tgcagtgctg ccataaccat gagtgataac    2220
actgcggcca acttacttct gacaacgatc ggaggaccga aggagctaac cgcttttttg    2280
cacaacatgg gggatcatgt aactcgcctt gatcgttggg aaccggagct gaatgaagcc    2340
ataccaaacg acgagcgtga caccacgatg cctaggagca atggcaacaa cgttgcgcaa    2400
actattaact ggcgaactac ttactctagc ttcccggcaa caattaatag actggatgga    2460
ggcggataaa gttgcaggac cacttctgcg ctcggccctt ccggctggct ggtttattgc    2520
tgataaatct ggagccggtg agcgtgggtc tcgcggtatc attgcagcac tggggccaga    2580
tggtaagccc tcccgtatcg tagttatcta cacgacgggg agtcaggcaa ctatggatga    2640
acgaaataga cagatcgctg agataggtgc ctcactgatt aagcattggc accaccacca    2700
ccaccactaa cccgggacca agtttactca tatatacttt agattgattt aaaacttcat    2760
ttttaattta aaaggatcta ggtgaagatc cttttttgata atctcatgac caaaatccct    2820
taacggcatg caccattcct tgcggcggcg gtgctcaacg gcctcaacct actactgggc    2880
tgcttcctaa tgcaggagtc gcataaggga gagcgtctgg cgaaggggg atgtgctgca    2940 aggcgattaa gttgggtaac gccagggttt tcccagtcac gacgttgtaa acgacggcc    3000 agtgccaagc ttaaaaaaaa tccttagctt tcgctaagga tctgcagtta atctctttt    3060 ctaattggct ctaaaatctt tataagttct tcagctacag catttttaa atccattgga    3120 tgcaattcct tattttaaa taactctct aactcctcat agctattaac tgtcaaatct    3180
ccaccaaatt tttctggcct ttttatggtt aaaggatatt caaggaagta tttagctatc    3240
tccattattg gatttccttc aacaactcca gctgggcagt atgctttctt tatcttagcc    3300
ctaatctctt ctggagagtc atcaacagct ataaaattcc ctttgaaga actcatcttt    3360 ccttctccat ccaaacccgt taagacaggg ttgtgaatac aaacaacctt ttttggtaaa    3420
agctcccttg ctaacatgtg tattttttctc tgctccatcc ctccaactgc aacatcaacg    3480
cctaaataat gaatatcatt aacctgcatt attggataga taacttcagc aacctttgga    3540
ttttcatcct ctcttgctat aagttccata ctccttcttg ctctttttaa ggtagttttt    3600
aaagccaatc tatagacatt cagtgtataa tccttatcaa gctggaattc agcgttacaa    3660
gtattacaca aagttttttta tgttgagaat atttttttga tggggcgcca cttatttttg    3720
atcgttcgct caaagaagcg gcgccagggn tgttttttctt ttcaccagtn agacgggcaa    3780
cagaacgcca tgagcggcct catttcttat tctgagttac aacagtccgc accgctgtcc    3840
```

-continued

```
ggtagctcct tccggtgggc gcggggcatg actatcgtcg ccgcacttat gactgtcttc    3900
tttatcatgc aactcgtagg acaggtgccg gcagcgccca acagtccccc ggccacgggg    3960
cctgccacca tacccacgcc gaaacaagcg ccctgcacca ttatgttccg gatctgcatc    4020
gcaggatgct gctggctacc ctgtggaaca cctacatctg tattaacgaa gcgctaaccg    4080
tttttatcag gctctgggag gcagaataaa tgatcatatc gtcaattatt acctccacgg    4140
ggagagcctg agcaaactgg cctcaggcat ttgagaagca cacggtcaca ctgcttccgg    4200
tagtcaataa accggtaaac cagcaataga cataagcggc tatttaacga ccctgccctg    4260
aaccgacgac cgggtcgaat ttgctttcga atttctgcca ttcatccgct tattatcact    4320
tattcaggcg tagcaccagg cgtttaaggg caccaataac tgccttaaaa aaattacgcc    4380
ccgccctgcc actcatcgca gtactgttgt aattcattaa gcattctgcc gacatggaag    4440
ccatcacaga cggcatgatg aacctgaatc gccagcggca tcagcacctt gtcgccttgc    4500
gtataatatt tgcccatggt gaaacgggg gcgaagaagt tgtccatatt ggccacgttt    4560
aaatcaaaac tggtgaaact cacccaggga ttggctgaga cgaaaaacat attctcaata    4620 aacccttag ggaaataggc caggttttca ccgtaacacg ccacatcttg cgaatatatg    4680
tgtagaaact gccggaaatc gtcgtggtat tcactccaga gcgatgaaaa cgtttcagtt    4740
tgctcatgga aaacggtgta acaagggtga acactatccc atatcaccag ctcaccgtct    4800
ttcattgcca tacg                                                      4814
```

<210> SEQ ID NO 33
<211> LENGTH: 4338
<212> TYPE: DNA
<213> ORGANISM: Artificial
<220> FEATURE:
<223> OTHER INFORMATION: plasmid pACKO-Bla
<220> FEATURE:
<221> NAME/KEY: misc_feature
<222> LOCATION: (3274)..(3274)
<223> OTHER INFORMATION: n is a, c, g, or t
<220> FEATURE:
<221> NAME/KEY: misc_feature
<222> LOCATION: (3294)..(3294)
<223> OTHER INFORMATION: n is a, c, g, or t

<400> SEQUENCE: 33

```
gaactccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa agttggccc agggcttccc    360 ggtatcaaca gggacaccag gatttatta ttctgcgaag tgatcttccg tcacaggtat    420
ttattcggcg caaagtgcgt cgggtgatgc tgccaactta ctgatttagt gtatgatggt    480 gttttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
```

```
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaccg ccctgcaagg cggttttttc gttttcagag caagagatta gcgcagacc    1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcggttt cttagacgtc aggtggcact tttcggggaa atgtgcgcgg aacccctatt   1740
tgtttatttt tctaaataca ttcaaatatg tatccgctca tgagacaata accctgataa   1800
atgcttcaat aatattgaaa aaggaagagt atgagtattc aacatttccg tgtcgccctt   1860
attcccttt ttgcggcatt ttgccttcct gttttgctc acccagaaac actagtgcag    1920
caatggcaac aacgttgcgc aaactattaa ctggcgaact acttactcta gcttcccggc   1980
aacaattaat agactggatg gaggcggata aagttgcagg accacttctg cgctcggccc   2040
ttccggctgg ctggtttatt gctgataaat ctggagccgg tgagcgtggg tctcgcggta   2100
tcattgcagc actggggcca gatggtaagc cctcccgtat cgtagttatc tacacgacgg   2160
ggagtcaggc aactatggat gaacgaaata gacagatcgc tgagataggt gcctcactga   2220
ttaagcattg gtaacccggg accaagttta ctcatatata ctttagattg atttaaaact   2280
tcatttttaa tttaaaagga tctaggtgaa gatcctttt gataatctca tgaccaaaat    2340
cccttaacgg catgcaccat tccttgcggc ggcggtgctc aacggcctca acctactact   2400
gggctgcttc ctaatgcagg agtcgcataa gggagagcgt ctggcgaaag ggggatgtgc   2460
tgcaaggcga ttaagttggg taacgccagg gttttcccag tcacgacgtt gtaaaacgac   2520
ggccagtgcc aagcttaaaa aaaatcctta gctttcgcta aggatctgca gttataatct   2580
ctttctaatt ggctctaaaa tctttataag ttcttcagct acagcatttt ttaaatccat   2640
tggatgcaat tccttatttt taaataaact ctctaactcc tcatagctat taactgtcaa   2700
atctccacca aattttttctg gccttttat ggttaaagga tattcaagga agtatttagc    2760
tatctccatt attggatttc cttcaacaac tccagctggg cagtatgctt tctttatctt   2820
agccctaatc tcttctggag agtcatcaac agctataaaa ttccctttg aagaactcat    2880
ctttccttct ccatccaaac ccgttaagac agggttgtga atacaaacaa ccttttttgg   2940
taaaagctcc cttgctaaca tgtgtatttt tctctgctcc atccctccaa ctgcaacatc   3000
aacgcctaaa taatgaatat cattaacctg cattattgga tagataactt cagcaacctt   3060
tggattttca tcctctcttg ctataagttc catactcctt cttgctcttt ttaaggtagt   3120
ttttaaagcc aatctataga cattcagtgt ataatcctta tcaagctgga attcagcgtt   3180
acaagtatta cacaaagttt tttatgttga gaatattttt ttgatggggc gccacttatt   3240
```

```
tttgatcgtt cgctcaaaga agcggcgcca gggntgtttt tcttttcacc agtnagacgg    3300
gcaacagaac gccatgagcg gcctcatttc ttattctgag ttacaacagt ccgcaccgct    3360
gtccggtagc tccttccggt gggcgcgggg catgactatc gtcgccgcac ttatgactgt    3420
cttctttatc atgcaactcg taggacaggt gccggcagcg cccaacagtc ccccggccac    3480
ggggcctgcc accatacccc cgccgaaaca agcgccctgc accattatgt tccggatctg    3540
catcgcagga tgctgctggc taccctgtgg aacacctaca tctgtattaa cgaagcgcta    3600
accgttttta tcaggctctg ggaggcagaa taaatgatca tatcgtcaat tattacctcc    3660
acggggagag cctgagcaaa ctggcctcag gcatttgaga agcacacggt cacactgctt    3720
ccggtagtca ataaaccggt aaaccagcaa tagacataag cggctattta acgaccctgc    3780
cctgaaccga cgaccgggtc gaatttgctt tcgaatttct gccattcatc cgcttattat    3840
cacttattca ggcgtagcac caggcgttta agggcaccaa taactgcctt aaaaaaatta    3900
cgccccgccc tgccactcat cgcagtactg ttgtaattca ttaagcattc tgccgacatg    3960
gaagccatca cagacggcat gatgaacctg aatcgccagc ggcatcagca ccttgtcgcc    4020
ttgcgtataa tatttgccca tggtgaaaac ggggggcgaag aagttgtcca tattggccac    4080
gtttaaatca aaactggtga aactcaccca gggattggct gagacgaaaa acatattctc    4140
aataaaccct ttagggaaat aggccaggtt ttcaccgtaa cacgccacat cttgcgaata    4200
tatgtgtaga aactgccgga aatcgtcgtg gtattcactc cagagcgatg aaaacgtttc    4260
agtttgctca tggaaaacgg tgtaacaagg gtgaacacta tcccatatca ccagctcacc    4320
gtctttcatt gccatacg                                                  4338

<210> SEQ ID NO 34
<211> LENGTH: 2271
<212> TYPE: DNA
<213> ORGANISM: Artificial
<220> FEATURE:
<223> OTHER INFORMATION: plasmid  pKQ

<400> SEQUENCE: 34
atggatccga gctcgagatc tgcagctggt accatatggg aattcgaagc ttgggcccga      60
acaaaaactc atctcagaag aggatctgaa tagcgccgtc gaccatcatc atcatcatca     120
ttgagtttaa acggtctcca gcttggctgt tttggcggat gagagaagat tttcagcctg     180
atacagatta aatcagaacg cagaagcggt ctgataaaac agaatttgcc tggcggcagt     240
agcgcggtgg tcccacctga ccccatgccg aactcagaag tgaaacgccg tagcgccgat     300
ggtagtgtgg ggtctcccca tgcgagagta gggaactgcc aggcatcaaa taaaacgaaa     360
ggctcagtcg aaagactggg cctttcgttt tatctgttgt ttgtcggtga acgatatctg     420 ctttttcttcg cgaattaatt ccgcttcgca acatgtgagc aaaaggccag caaaaggcca     480
ggaaccgtaa aaaggccgcg ttgctggcgt ttttccatag gctccgcccc cctgacgagc     540
atcacaaaaa tcgacgctca agtcagaggt ggcgaaaccc gacaggacta taaagatacc     600
aggcgtttcc ccctggaagc tccctcgtgc gctctcctgt tccgaccctg ccgcttaccg     660
gatacctgtc cgcctttctc ccttcgggaa gcgtggcgct ttctcatagc tcacgctgta     720
ggtatctcag ttcggtgtag gtcgttcgct ccaagctggg ctgtgtgcac gaaccccccg     780
ttcagcccga ccgctgcgcc ttatccggta actatcgtct gagtccaacc cggtaagac      840 acgacttatc gccactggca gcagccactg gtaacaggat tagcagagcg aggtatgtag     900
gcggtgctac agagttcttg aagtggtggc ctaactacgg ctacactaga aggacagtat     960
```

| | |
|---|---:|
| ttggtatctg cgctctgctg aagccagtta ccttcggaaa aagagttggt agctcttgat | 1020 |
| ccggcaaaca aaccaccgct ggtagcggtg gttttttttgt ttgcaagcag cagattacgc | 1080 |
| gcagaaaaaa aggatctcaa gaagatcctt tgatcttttc tacggggtct gacgctcagt | 1140 |
| ggaacgaaaa ctcacgttaa gggattttgg tcatgagttg tgtctcaaaa tctctgatgt | 1200 |
| tacattgcac aagataaaaa tatatcatca tgaacaataa aactgtctgc ttacataaac | 1260 |
| agtaatacaa ggggtgttat gagccatatt caacgggaaa cgtcttgctc gaggccgcga | 1320 |
| ttaaattcca acatggatgc tgatttatat gggtataaat gggctcgcga taatgtcggg | 1380 |
| caatcaggtg cgacaatcta tcgattgtat gggaagcccg atgcgccaga gttgtttctg | 1440 |
| aaacatggca aaggtagcgt tgccaatgat gttacagatg agatggtcag actaaactgg | 1500 |
| ctgacggaat ttatgcctct tccgaccatc aagcatttta tccgtactcc tgatgatgca | 1560 |
| tggttactca ccactgcgat ccccgggaaa acagcattcc aggtattaga agaatatcct | 1620 |
| gattcaggtg aaaatattgt tgatgcgctg gcagtgttcc tgcgccggtt gcattcgatt | 1680 |
| cctgtttgta attgtccttt taacagcgat cgcgtatttc gtctcgctca ggcgcaatca | 1740 |
| cgaatgaata acggtttggt tgatgcgagt gattttgatg acgagcgtaa tggctggcct | 1800 |
| gttgaacaag tctggaaaga atgcataag cttttgccat tctcaccgga ttcagtcgtc | 1860 |
| actcatggtg atttctcact tgataacctt atttttgacg aggggaaatt aataggttgt | 1920 |
| attgatgttg gacgagtcgg aatcgcagac cgataccagg atcttgccat cctatggaac | 1980 |
| tgcctcggtg agttttctcc ttcattacag aaacggcttt ttcaaaaata tggtattgat | 2040 |
| aatcctgata tgaataaatt gcagtttcat ttgatgctcg atgagttttt ctaatcagaa | 2100 |
| ttggttaatt ggttgtaaca ctggcagagc attacgctga cttgacggga cggcggcttt | 2160 |
| gttgaataaa tcgaactttt gctgagttga aggatcctcg ggagttgtca gcctgtcccg | 2220 |
| cttataagat catacgccgt tatacgttgt ttacgctttg aggaattaac c | 2271 |

<210> SEQ ID NO 35
<211> LENGTH: 4582
<212> TYPE: DNA
<213> ORGANISM: Artificial
<220> FEATURE:
<223> OTHER INFORMATION: plasmid pKQ-PhKep

<400> SEQUENCE: 35

| | |
|---|---:|
| atggttcatt gggccgatta tattgctgat aaaataatta gagagagggg ggagaaggag | 60 |
| aagtacgttg ttgagagtgg aataacgcca agtggttacg ttcacgttgg aactttagg | 120 |
| gagcttttta cagcttatat tgtgggccat gccctaaggg ataaggggta tgaggttagg | 180 |
| cacatccaca tgtgggatga ttatgataga tttaggaagg ttccaaggaa cgttccccag | 240 |
| gaatggaaag attacctggg aatgcccatt agtgaagttc ctgatccctg gggatgccat | 300 |
| gagagttatg ctgaacactt catgagaaag ttcgaggagg aggtagaaaa attagggatc | 360 |
| gaagttgact ttcttatgc gagtgaactc tacaagagag gggaatattc tgaggagata | 420 |
| aggttagcct ttgagaaaag ggataagata atggagatac taaacaagta tagggaaatt | 480 |
| gcgaaacaac ctcccccttcc agagaactgg tggcccgcaa tggtttactg ccctgagcat | 540 |
| aggagggaag cagagatcat tgaatggat ggggctgga aggttaagta taagtgccc | 600 |
| gaaggtcacg agggatgggt tgatataagg agtgggaacg tgaaactgag gtggcgtgtt | 660 |
| gattggccca tgcgttggtc tcactttggc gttgacttcg aacctgctgg aaaggatcat | 720 |
| cttgtggctg gttcaagcta cgatacggga aaggagatta taaaggaagt ttatggaaag | 780 |

```
gaagctccgt tatctttaat gtatgagttt gttggaatta aggggcagaa ggggaagatg    840
agtggtagta agggaaatgt tattttactc agcgatctgt atgaggttct tgagccaggt    900
ctcgttagat ttatctacgc tcggcatagg ccaaacaagg agataaagat agatctaggt    960
cttggcattc taaacctcta cgatgagttc gataaagttg agagaatata cttcggggtt   1020
gagggtggta aggtgatga tgaagaatta aggaggactt acgagctttc ggtgatgctg   1080
ccaacttact gatttagtgt atgatggtgt ttttgaggtg ctccagtggc ttctgtttct   1140
atcagctgtc cctcctgttc agctactgac ggggtggtgc gtaacggcaa aagcaccgcc   1200
ggacatcagc gctatctctg ctctcactgc cgtaaaacat ggcaactgca gttcacttac   1260
accgcttctc aacccggtac gcaccagaaa atcattgata tggccatgaa tggcgttgga   1320
tgccgggcaa ccgcccgcat tatgggcgtt ggcctcaaca cgattttccg ccatttaaaa   1380
aactcaggcc gcagtcggta acctcgcgca tacagccggg cagtgacgtc atcgtctgcg   1440
cggaaatgga cgaacagtgg ggatacgtcg gtgctaaatc gcgccagcgc tggctgtttt   1500
acgcgtatga caggctccgg aagacggttg ttgcgcacgt attcggtgaa cgcactatgg   1560
cgacgctggg gcgtcttatg agcctgctgt caccctttga cgtggtgata tggatgacgg   1620
atggctggcc gctgtatgaa tcccgcctga agggaaagct gcacgtaatc agcaagcgat   1680
atacgcagcg aattgagcgg cataacctga atctgaggca gcacctggca cggctgggac   1740
ggaagtcgct gtcgttctca aaatcggtgg agctgcatga caaagtcatc gggcattatc   1800
tgaacataaa acactatcaa taagttggag tcattacccc gagctttcaa tgcctaagaa   1860
gcctgagaga ttagtcgctc aagctccttt taggttccta gcggtgttgg ttcagttacc   1920
gcatttaacc gaagaagaca taataaatgt tctaatcaaa cagggacata ttcccaggga   1980
tctatccaag gaggacgttg agagggttaa acttaggata aaccttgcta ggaattgggt   2040
taaaaagtat gccctgagg atgttaaatt ctcaatactt gagaaacctc cagaagttga   2100
ggtaagtgaa gatgttaggg aggccatgaa tgaggttgct gagtggcttg agaatcatga   2160
ggaatttagc gttgaagagt ttaataacat tctattcgaa gttgccaaga ggaggggat   2220 atccagtagg gagtggtttt cgacgctcta cagattattt attggaaagg aaaggggacc   2280
gagattggcc agtttcctgg catctcttga taggagtttc gttattaaac gacttagact   2340
tgagggataa gaattcgaag cttgggcccg aacaaaaact catctcagaa gaggatctga   2400
atagcgccgt cgaccatcat catcatcatc attgagttta acggtctcc agcttggctg   2460 ttttggcgga tgagagaaga ttttcagcct gatacagatt aaatcagaac gcagaagcgg   2520
tctgataaaa cagaatttgc ctggcggcag tagcgcggtg gtcccacctg accccatgcc   2580
gaactcagaa gtgaaacgcc gtagcgccga tggtagtgtg gggtctcccc atgcgagagt   2640
agggaactgc caggcatcaa ataaaacgaa aggctcagtc gaaagactgg gcctttcgtt   2700
ttatctgttg tttgtcggtg aacgatatct gcttttcttc gcgaattaat tccgcttcgc   2760
aacatgtgag caaaaggcca gcaaaggcc aggaaccgta aaaaggccgc gttgctggcg   2820
tttttccata ggctccgccc ccctgacgag catcacaaaa atcgacgctc aagtcagagg   2880
tggcgaaacc cgacaggact ataaagatac caggcgtttc cccctggaag ctccctcgtg   2940
cgctctcctt ttccgaccct gccgcttacc ggatacctgt ccgcctttct cccttcggga   3000
agcgtggcgc tttctcatag ctcacgctgt aggtatctca gttcggtgta ggtcgttcgc   3060
tccaagctgg gctgtgtgca cgaacccccc gttcagcccg accgctgcgc cttatccggt   3120
aactatcgtc ttgagtccaa cccggtaaga cacgacttat cgccactggc agcagccact   3180
```

```
ggtaacagga ttagcagagc gaggtatgta ggcggtgcta cagagttctt gaagtggtgg    3240
cctaactacg gctacactag aaggacagta tttggtatct gcgctctgct gaagccagtt    3300
accttcggaa aaagagttgg tagctcttga tccggcaaac aaaccaccgc tggtagcggt    3360 ggttttttg tttgcaagca gcagattacg cgcagaaaaa aaggatctca agaagatcct     3420
ttgatctttt ctacggggtc tgacgctcag tggaacgaaa actcacgtta agggattttg    3480
gtcatgagtt gtgtctcaaa atctctgatg ttacattgca caagataaaa atatatcatc    3540
atgaacaata aaactgtctg cttacataaa cagtaataca aggggtgtta tgagccatat    3600
tcaacgggaa acgtcttgct cgaggccgcg attaaattcc aacatggatg ctgatttata    3660
tgggtataaa tgggctcgcg ataatgtcgg gcaatcaggt gcgacaatct atcgattgta    3720
tgggaagccc gatgcgccag agttgtttct gaaacatggc aaaggtagcg ttgccaatga    3780
tgttacagat gagatggtca gactaaactg gctgacggaa tttatgcctc ttccgaccat    3840
caagcatttt atccgtactc ctgatgatgc atggttactc accactgcga tccccgggaa    3900
aacagcattc caggtattag aagaatatcc tgattcaggt gaaaatattg ttgatgcgct    3960
ggcagtgttc ctgcgccggt tgcattcgat tcctgttgt aattgtcctt ttaacagcga     4020
tcgcgtattt cgtctcgctc aggcgcaatc acgaatgaat aacggtttgg ttgatgcgag    4080 tgatttgat gacgagcgta atggctggcc tgttgaacaa gtctggaaag aaatgcataa     4140
gcttttgcca ttctcaccgg attcagtcgt cactcatggt gatttctcac ttgataacct    4200 tattttgac gaggggaaat taataggttg tattgatgtt ggacgagtcg gaatcgcaga    4260
ccgataccag gatcttgcca tcctatggaa ctgcctcggt gagttttctc cttcattaca    4320
gaaacggctt tttcaaaaat atggtattga taatcctgat atgaataaat tgcagtttca    4380
tttgatgctc gatgagtttt tctaatcaga attggttaat tggttgtaac actggcagag    4440
cattacgctg acttgacggg acggcggctt tgttgaataa atcgaacttt tgctgagttg    4500
aaggatcctc gggagttgtc agcctgtccc gcttataaga tcatacgccg ttatacgttg    4560
tttacgcttt gaggaattaa cc                                            4582

<210> SEQ ID NO 36
<211> LENGTH: 30
<212> TYPE: DNA
<213> ORGANISM: Artificial
<220> FEATURE:
<223> OTHER INFORMATION: oligonucleotide primer

<400> SEQUENCE: 36
cagtggaatt cagtaagttg gcagcatcac                                      30

<210> SEQ ID NO 37
<211> LENGTH: 31
<212> TYPE: DNA
<213> ORGANISM: Artificial
<220> FEATURE:
<223> OTHER INFORMATION: oligonucleotide primer

<400> SEQUENCE: 37
cattggaatt cgagtaagtt ggcagcatca c                                    31
```

COMPOSITIONS OF ORTHOGONAL LYSYL-TRNA AND AMINOACYL-TRNA SYNTHETASE PAIRS AND USES THEREOF

CROSS-REFERENCE TO RELATED APPLICATIONS

This application is a 371 application of International Application No. PCT/US2004/022187 filed Jul. 7, 2004 which claims priority to and benefit of Provisional Patent Application U.S. Ser. No. 60/485,451, filed Jul. 7, 2003; Provisional Patent Application U.S. Ser. No. 60/528,815, filed Dec. 10, 2003; and Provisional Patent Application U.S. Ser. No. 60/537,149, filed Jan. 15, 2004, the disclosures of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant DE-FG0300ER45812 from the Department of Energy. The government may have certain rights to this invention.

FIELD OF THE INVENTION

The invention is in the field of translation biochemistry. The invention relates to methods for producing and compositions of orthogonal tRNAs, orthogonal aminoacyl-tRNA synthetases, and pairs thereof, that incorporate unnatural amino acids, e.g., homoglutamines, into proteins in response to selector codons such as four base and stop selector codons. This includes the incorporation of multiple different unnatural amino acids into a single protein chain in response to stop and four base selector codons. The invention also relates to methods of producing proteins in cells using such pairs and related compositions.

BACKGROUND OF THE INVENTION

Although, with few exceptions, the genetic codes of all known organisms encode the same twenty amino acids, all that is required to add a new amino acid to the repertoire of an organism is a unique tRNA/aminoacyl-tRNA synthetase pair, a source of the amino acid, and a unique selector codon that specifies the amino acid (Furter (1998) *Protein Sci.*, 7:419-426). Previously, we have shown that the amber nonsense codon, TAG, together with orthogonal *M. jannaschii* and *E. coli* tRNA/synthetase pairs can be used to genetically encode a variety of amino acids with novel properties in *E. coli* (Wang et al., (2000) *J. Am. Chem. Soc.*, 122:5010-5011; Wang et al., (2001) *Science*, 292:498-500; Wang et al., (2003) *Proc. Natl. Acad. Sci. U.S.A.*, 100:56-61; Chin et al., (2002) *Proc. Natl. Acad. Sci. U.S.A.*, 99:11020-11024), and yeast (Chin and Schultz, (2002) *ChemBioChem*, 3:1135-1137), respectively. The limited number of noncoding triplet codons, however, severely restricts the ultimate number of amino acids encoded by any organism.

There are many examples of naturally occurring +1 frameshift suppressors including UAGN suppressors derived from Su7 encoding glutamine (Magliery et al., (2001) *J. Mol. Biol.*, 307:755-769), sufJ-derived suppressors of ACCN codons encoding threonine (Anderson et al., (2002) *Chem. Biol.*, 9:237-244) and CAAA suppressors derived from tRNA$^{Lys}$ and tRNA$^{Gln}$ (Anderson and Schultz, (2003) *Biochemistry*, 42(32):9598-608). Moreover, genetic selections have been used to identify efficient four- and five-base codon suppressor tRNAs from large libraries of mutant tRNAs, including an *E. coli* tRNA$_{UCCU}^{Ser}$ suppressor (Ibba et al., (1999) *Proc. Natl. Acad. Sci. U.S.A.*, 96:418-423; Kwok and Wong, (1980) *Can. J. Biochem.*, 58:213-218). This natural phenomena has been extended for unnatural amino acid mutagenesis in vitro using chemically aminoacylated tRNAs. A variety of amino acids, including fluorophore/quencher pairs (Terada et al., (2002) *Nat. Struct. Biol.*, 9:257-262), have been incorporated into protein in response to AGGU and CGGG (Hou et al., (1992) *Biochemistry*, 31:4157-4160; Yarus et al., (1986) *J. Mol. Biol.*, 192:235-255; Miller, (1972) *Experiments in molecular genetics*, Cold Spring Harbor Laboratory, Cold Spring Harbor, N.Y). To further expand the genetic code, there is a need to develop improved and/or additional components of the biosynthetic machinery, e.g., orthogonal tRNAs, orthogonal aminoacyl-tRNA synthetases and/or unique codons. This invention fulfills these and other needs, as will be apparent upon review of the following disclosure.

SUMMARY OF THE INVENTION

The present invention provides novel translation systems that produce protein products using orthogonal tRNA and orthogonal aminoacyl tRNA synthetases. The invention relates to the assembled translation system, the methods for using the translation system, and the translation products produced by the system. This technology finds a number of uses as discussed herein, for example, but not limited to, the production of therapeutic products, diagnostic reagents and industrial enzymes.

In one aspect, the invention provides a translation system that uses an orthogonal lysyl tRNA (lysyl O-tRNA) or a modified variant of that O-tRNA and/or an orthogonal aminoacyl tRNA synthetase (O-RS) that preferentially charges an orthogonal lysyl tRNA with one or more amino acid or a modified variant of that O-RS. In some embodiments, the translation system is in a cell, for example, an *E. coli* cell. The amino acid optionally coupled to the O-tRNA is an unnatural amino acid, for example homoglutamine.

In some embodiments of the translation system, the lysyl O-tRNA, the variant of the O-tRNA, the O-RS, or both the O-tRNA and the O-RS, are derived from *Pyrococcus horikoshii* (PhKRS). Various O-RSs that find use with the translation system, include PhKRS, E444G, PhΔAD, and an I41 and/or S268 mutant of PhΔAD. In some embodiments, the *Pyrococcus horikoshii* O-RS, when expressed in an *E. coli* cell displays a toxicity that is the same as or less than the toxicity of an I41 and/or S268 mutant of PhΔAD.

The lysyl O-tRNA or the variant O-tRNA optionally includes a recognition sequence for a four base codon or an amber codon. For example, the lysyl O-tRNA or variant can include a recognition sequence for AGGA. In related aspects of the translation system, the lysyl O-tRNA or variant uses an anti-codon loop with the sequence CU(X)$_n$XXXAA. In some embodiments of this aspect, the CU(X)$_n$XXXAA sequence can be CUCUAAA or CUUCCUAA. Examples include the lysyl O-tRNA or variant thereof that includes the sequences found in SEQ ID NO:24 or SEQ ID NO:26.

In some embodiments of the invention, the O-RS, the lysyl O-tRNA or the variants are at least 50% as effective at suppressing a stop or frame shift selector codon as E444G, PhΔAD, or an I41 and/or S268 mutant of PhΔAD, in combination with an O-tRNA of SEQ ID NO:24 or SEQ ID NO:26. In other embodiments, the translation system uses an additional O-RS and an additional O-tRNA, where these additional components suppress a frame shift selector codon that is different from a frame shift selector codon suppressed by the lysyl O-tRNA or O-tRNA variant and the O-RS that preferentially charges the lysyl O-tRNA or O-tRNA variant. In other embodiments, the translation system suppresses both a four base selector codon and a stop selector codon in a target nucleic acid that encodes a target polypeptide. The four base selector codon optionally uses the sequence AGGA and the stop selector codon optionally uses the sequence TAG or UAG. In some embodiments, the translation system includes a target nucleic acid that comprises a four base selector codon. The translation system optionally incorporates a protein encoded by the target nucleic acid. For example, this protein can incorporate a homoglutamine residue.

The translation system optionally incorporates a target nucleic acid that encodes a four base selector codon and a stop selector codon. In some aspects, the translation system incorporates a protein encoded by the target nucleic acid, where the protein includes at least two different unnatural amino acids.

The invention provides, e.g., a translation system that uses a first orthogonal tRNA (O-tRNA) that recognizes a four base selector codon, a first orthogonal aminoacyl tRNA synthetase (O-RS) that preferentially charges the O-tRNA with a first unnatural amino acid, a second O-tRNA that recognizes a stop selector codon, and a second O-RS that preferentially charges the second O-tRNA with a second unnatural amino acid. In one embodiment, the four base selector codon is AGGA, and the stop codon is UAG. Optionally, the translation system is in a cell.

In some embodiments of the translation system, the first or second O-tRNA is an orthogonal lysyl tRNA (lysyl O-tRNA) or modified variant. Optionally, the first O-tRNA is an orthogonal lysyl tRNA (lysyl O-tRNA) or suitable variant and the second O-tRNA is an orthogonal tyrosyl tRNA (tyrosyl O-tRNA) or suitable variant. Optionally, the translation system incorporates a nucleic acid encoding at least a four base selector codon and a stop selector codon. In these embodiments, the four base selector codon can be AGGA and the stop selector codon can be TAG or UAG, and the nucleic acid to be translated is typically an expressed RNA. In some embodiments, the protein encoded by the nucleic acid incorporates at least two different unnatural amino acids, for example homoglutamine and a second unnatural amino acid, such as an electrophillic amino acid. The translation system can include any of a variety of unnatural amino acids, including, e.g., homoglutamine. In one example, the protein in the translation system is homologous to myoglobin, but includes an unnatural amino acid such as homoglutamine.

The present invention provides compositions that incorporate, but are not limited to, the amino acid sequences of PhKRS, E444G, PhΔAD, an I41 and/or S268 mutant of PhΔAD, or a conservative variant of these proteins. The invention similarly provides nucleic acids that encode PhKRS, E444G, PhΔAD, an I41 and/or S268 mutant of PhΔAD, and/or any conservative variant of these sequences. The invention provides nucleic acids that incorporate in part or consist entirely of a tRNA that corresponds to SEQ ID NO:24 or SEQ ID NO:26, or any conservative variants of these sequences.

In other aspects, the invention provides compositions that incorporate, but are not limited to, an orthogonal aminoacyl-tRNA synthetase (O-RS), wherein the O-RS preferentially aminoacylates an O-tRNA with a homoglutamine. This O-RS can include a mutation corresponding to an I41 and/or S268 mutation of PhΔAD, or any conservative variant of this protein. In some embodiments, the O-RS preferentially aminoacylates the O-tRNA with an efficiency of at least 50% of the efficiency of an I41 and/or S268 mutation of PhΔAD. In some embodiments, the O-RS is derived from *Pyrococcus horikoshii*. In some embodiments where both the O-RS and O-tRNA are present in the composition, the O-tRNA recognizes a four base selector codon, for example, an AGGA sequence.

In some embodiments where the above composition includes or is present within a cell, the O-RS can be encoded by one or more nucleic acids in the cell, which can be, for example, an *E. coli* cell. The composition can incorporate a translation system. In compositions that incorporate a cell and where the O-RS is encoded by one or more nucleic acids in the cell, the cell can further include an orthogonal-tRNA (O-tRNA) that recognizes a first selector codon and a homoglutamine, e.g., where the O-RS preferentially aminoacylates the O-tRNA with the homoglutamine. In some embodiments, the cell can include a target nucleic acid that encodes a polypeptide of interest, where the target nucleic acid encodes a selector codon that is recognized by the O-tRNA.

The O-tRNA is optionally encoded entirely or partially by a polynucleotide sequence as set forth in SEQ ID NO:24 or SEQ ID NO:26, or a complementary polynucleotide sequence thereof, and the O-RS incorporates an amino acid sequence corresponding to E444G, PhΔAD, an I41 and/or S268 mutant of PhΔAD, or any conservative variant of that sequence. It will be appreciated that any nucleic acid sequence herein can be represented in an RNA or DNA form; thus, unless context dictates otherwise, sequences such as SEQ ID NO: 24 or 25 optionally include RNA and/or DNA forms, whether expressly shown or not. In some embodiments, the O-RS and O-tRNA are at least 50% as effective at suppressing a stop or frame shift selector codon as E444G, PhΔAD, or an I41 and/or S268 mutant of PhΔAD, in combination with an O-tRNA of SEQ ID NO:24 or SEQ ID NO:26. In embodiments where the composition incorporates a cell, the cell can be an *E. coli* cell. A cell of this composition can further include an additional different O-tRNA/O-RS pair and an additional different unnatural amino acid, where the O-tRNA recognizes a second selector codon and the O-RS preferentially aminoacylates the O-tRNA with the second unnatural amino acid. The cell can optionally further include a target nucleic acid that encodes the first and second selector codons. Furthermore still, a cell of this composition can include a protein encoded by the target nucleic acid, where the protein incorporates at least two different unnatural amino acids.

The invention also provides a protein that includes at least one homoglutamine. In some embodiments, the protein includes an amino acid sequence that is at least 75% identical to a sequence of a wild-type therapeutic protein, a diagnostic protein, an industrial enzyme, or any portion of these proteins. Optionally, the protein exists in conjunction with a pharmaceutically acceptable carrier.

In another aspect, the invention provides methods for selecting an active orthogonal-aminoacyl-tRNA synthetase (O-RS) that loads a homoglutamine on an orthogonal tRNA (O-tRNA). These methods utilize a first step of subjecting a population of cells to selection, where the cells collectively include, 1) the O-tRNA, where the O-tRNA is orthogonal to members of the population of cells that comprise the O-tRNA; 2) a plurality of O-RSs that have one or more active O-RS members that load the O-tRNA with a homoglutamine in one or more cells of the population; 3) a polynucleotide that encodes a selectable marker, where the polynucleotide encodes at least one selector codon that is recognized by the O-tRNA; and, 4) homoglutamine. In this selection, the target cell in the population that comprises the active O-RS is identified by an enhanced suppression efficiency of the selectable marker as compared to a suppression efficiency of a control cell lacking the plurality of RSs but harboring the O-tRNA. The second step of the method is the selection procedure that selects the target cell that harbors an active O-RS. The invention further provides the orthogonal aminoacyl-tRNA synthetase identified by any of the selection methods.

In some embodiments of these methods, the cells are additionally selected to eliminate cells that comprise a non-target O-RS that charges the O-tRNA with an amino acid other than homoglutamine. In some embodiments, the selection is a positive selection and the selectable marker is a positive selection marker.

In various embodiments of these methods, the plurality of RSs can come from any of a variety of sources, including, but not limited to, mutant RSs, RSs derived from one or more species other than the first species or both mutant RSs and RSs derived from a species other than the first species.

The invention also provides methods for producing a protein in a cell with a homoglutamine at a specified position. The method includes the steps of growing, in an appropriate medium, a cell that harbors a nucleic acid that encodes at least one selector codon and encodes a protein; e.g., where the cell further includes an orthogonal-tRNA (O-tRNA) that recognizes the selector codon and an orthogonal aminoacyl-tRNA synthetase (O-RS) that preferentially aminoacylates the O-tRNA with homoglutamine; providing the homoglutamine; and incorporating the homoglutamine into the specified position in response to the selector codon, thereby producing the protein. In one embodiment of this method, the amino acid sequence of the O-RS uses entirely, or in part, the amino acid sequence of E444G, PhΔAD, an I41 and/or S268 mutant of PhΔAD, or a conservative variant thereof.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Unless defined herein and below in the reminder of the specification, all technical and scientific terms used herein have the same meaning as commonly understood by one of ordinary skill in the art to which the invention pertains.

Orthogonal lysyl-tRNA: As used herein, an orthogonal lysyl-tRNA (lysyl-O-tRNA) is a tRNA that is orthogonal to a translation system of interest, where the tRNA is: (1) identical or substantially similar to a naturally occurring lysyl tRNA, (2) derived from a naturally occurring lysyl tRNA by natural or artificial mutagenesis, (3) derived by any process that takes a sequence of a wild-type or mutant lysyl tRNA sequence of (1) or (2) into account, (4) homologous to a wild-type or mutant lysyl tRNA; (5) homologous to any example tRNA that is designated as a substrate for a lysyl tRNA synthetase in TABLE 1, or (6) a conservative variant of any example tRNA that is designated as a substrate for a lysyl tRNA synthetase in TABLE 1. The lysyl tRNA can exist charged with an amino acid, or in an uncharged state. It is also to be understood that a "lysyl-O-tRNA" optionally is charged (aminoacylated) by a cognate synthetase with an amino acid other than lysine, e.g., with the amino acid homoglutamine. Indeed, it will be appreciated that a lysyl-O-tRNA of the invention is advantageously used to insert essentially any amino acid, whether natural or artificial, into a growing polypeptide, during translation, in response to a selector codon.

Orthogonal lysyl amino acid synthetase: As used herein, an orthogonal lysyl amino acid synthetase (lysyl-O-RS) is an enzyme that preferentially aminoacylates the lysyl-O-tRNA with an amino acid in a translation system of interest. The amino acid that the lysyl-O-RS loads onto the lysyl-O-tRNA can be any amino acid, whether natural or artificial, and is not limited herein. The synthetase is optionally the same as or homologous to a naturally occurring lysyl amino acid synthetase, or the same as or homologous to a synthetase designated as a lysyl-O-RS in TABLE 1. For example, the lysyl-O-RS can be a conservative variant of a lysyl-O-RS of TABLE 1, and/or can be at least 50%, 60%, 70%, 80%, 90%, 95%, 98%, 99% or more identical in sequence to a lysyl-O-RS of TABLE 1.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to the ability of an endogenous tRNA to function with the endogenous tRNA synthetase; or of an orthogonal aminoacyl-tRNA synthetase to function with an endogenous tRNA compared to the ability of an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even undetectable efficiency, when compared to aminoacylation of an endogenous tRNA by the endogenous RS. In another example, an orthogonal RS aminoacylates any endogenous tRNA in a cell of interest with reduced or even undetectable efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Cognate: The term "cognate" refers to components that function together, e.g., an orthogonal tRNA and an orthogonal aminoacyl-tRNA synthetase that preferentially aminoacylates the orthogonal tRNA. The components can also be referred to as being "complementary."

Preferentially aminoacylates: The term "preferentially aminoacylates" indicates that an O-RS charges a particular tRNA with a given amino acid more efficiently than it charges other tRNAs. For example, the O-RS can charge a cognate O-tRNA with an efficiency (e.g., 70% efficiency, 75% efficiency, 85% efficiency, 90% efficiency, 95% efficiency, or 99% or more efficiency), as compared to the O-RS aminoacylating a non-cognate tRNA (e.g., a tRNA used as a substrate for creating the cognate O-tRNA, e.g., via mutation).

Selector codon: The term "selector codon" refers to a codon recognized by an O-tRNA in a translation process that is not typically recognized by an endogenous tRNA. Typical examples include stop codons, codons comprising 4 our more bases, and/or the like. An O-tRNA anticodon loop recognizes a selector codon, e.g., in an expressed RNA, e.g., an mRNA, and inserts its amino acid into a polypeptide being translated by translation system components. For example, in one embodiment herein, the O-tRNA recognizes a selector codon such as a four base codon and adds an unnatural amino acid, such as a homoglutamine, into a polypeptide being produced by the translation process. Selector codons can include, e.g., nonsense codons, such as stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, etc.

Suppression activity: As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various means by which suppression activity can be quantitated. Percent suppression of a particular O-tRNA and ORS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, such as a homoglutamine, that is not one of the 20 common naturally occurring amino acids or the rare natural amino acids seleno cysteine or pyrrolysine.

Derived from: As used herein, the term "derived from" refers to a component that is isolated from or made using a specified molecule or organism, or information from the specified molecule or organism.

Positive selection or screening marker: As used herein, the term "positive selection or screening marker" refers to a marker that when present, e.g., expressed, activated, or the like, results in identification of a cell that comprises a trait corresponding to the marker, e.g., cells with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/acZ (β-galactosidase), Adh (alcohol dehydrogenase), his3, ura3, leu2, lys2, or the like.

Eukaryote; As used herein, the term "eukaryote" refers to organisms belonging to the phylogenetic domain Eucarya, such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g.,

*Methanococcus jannaschii* (Mj), *Methanosarcina mazei* (Mm), *Methanobacterium thermoautotrophicum* (Mt), *Methanococcus maripaludis*, *Methanopyrus kandleri*, *Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum*, *Pyrococcus abyssi*, *Sulfolobus solfataricus* (Ss), *Sulfolobus tokodaii*, *Aeuropyrum pernix* (Ap), *Thermoplasma acidophilum*, *Thermoplasma volcanium*, etc.) phylogenetic domains.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS will aminoacylate a complementary O-tRNA or a conservative variant O-tRNA with an unnatural amino acid, e.g., a homoglutamine, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which a tRNA of the invention recognizes a selector codon and incorporates a relevant amino acid, e.g., an unnatural amino acid such as homoglutamine, which is carried by the tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 1 provides a sequence alignment of archaeal tRNA$^{Lys}$ sequences.(SEQ ID NOs:1-23, from top to bottom). Genomic sequences derived from Pa, *Pyrococcus abyssi*; Pf, *Pyrococcus furiosus*; Ph, *Pyrococcus horikoshii*; Pya, *Pyrobaculum aerophilum*; Ta, *Thermoplasma acidophilum*; Tv, *Thermoplasma volcanum*; Af, *Archaeoglobus fulgidus*; Hh, *Halobacterium* sp. NRC-1; Mj, *Methanococcus jannaschii*; Mt. *Methanobacterium thermeautotrophicum*; Mm, *Methanosarcina mazei*; St, *Sulfolobus tokodaii*; Ss, *Sulfolobus solfataricus*; Ap, *Aeropyrum pernix* were aligned with the GCG program pileup and displayed with the program prettybox.

FIG. 6A shows the structure of the PhKRS active site. Residues E41 and Y268 make specific contacts with the lysine substrate. These residues were simultaneously randomized for the construction of active site libraries. FIG. 6B shows the structures of various amino acids.

FIG. 7A, the myoglobin gene with an AGGA codon at position G24 was expressed in the presence of the AK$_{UCCU}$ tRNA and either PhΔAD, an hGln-specific variant, or JYRS. Expression of myoglobin by amber suppression at position S4 was similarly attempted with PhΔAD or JYRS. b, hGln was incorporated by AGGA suppression at position 24 and AzPhe was incorporated by amber suppression at position 75 in a single polypeptide.

DETAILED DESCRIPTION

Figure 2A:
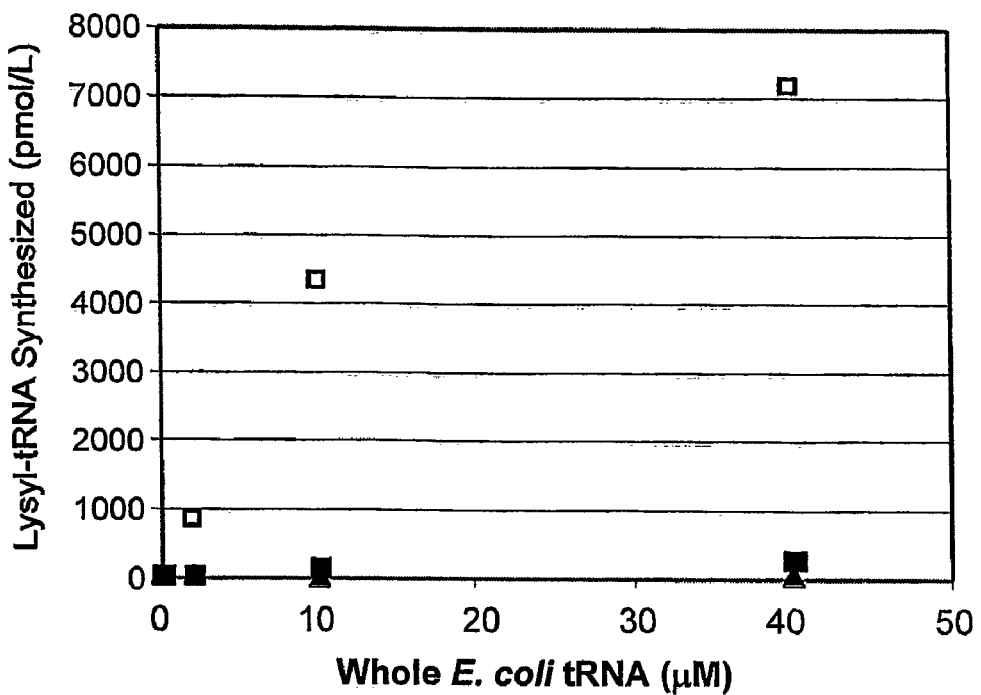
FIG. 2, Panels A and B provides histograms illustrating cross-species aminoacylation in vitro. (A) Aminoacylation of whole *E. coli* tRNA, or (B) whole halobacterial tRNA by EcKRS (□), PhKRS (■), or no synthetase (▲). Assays were performed in 20 μL reactions containing 50 mM Tris-Cl, pH 7.5, 30 mM KCl, 20 mM MgCl$_2$, 3 mM glutathione, 0.1 mg/mL BSA, 10 mM ATP, 1 μM [$^3$H] lysine (Amersham), 750 nM synthetase, and 0, 2, 10, or 40 μM whole tRNA at 37° C. for 20 minutes.

In order to add additional synthetic amino acids, such as a homoglutamine, to the genetic code, in vivo, new orthogonal pairs of an aminoacyl-tRNA synthetase and a tRNA are needed that can function efficiently in the translational machinery, but that are "orthogonal," to the translation system at issue, meaning that the pairs function independently of the synthetases and tRNAs endogenous to the translation system. Desired characteristics of the orthologous pair include tRNA that decode or recognize only a specific new codon, e.g., a selector codon, that is not decoded by any endogenous tRNA, and aminoacyl-tRNA synthetases that preferentially aminoacylate (or charge) its cognate tRNA with only a specific non-natural amino acid, e.g., a homoglutamine. The O-tRNA is also desireably not aminoacylated by endogenous synthetases. For example, in *E. coli*, an orthogonal pair will include an aminoacyl-tRNA synthetase that does not substantially aminoacylate any of the endogenous tRNAs, e.g., of which there are 40 in *E. coli*, and an orthogonal tRNA that is not aminoacylated by any of the endogenous synthetases, e.g., of which there are 21 in *E. coli*.

Here we report the generation of a new orthogonal synthetase/tRNA pair derived from archaeal tRNA$^{Lys}$ sequences that efficiently and selectively incorporate the amino acid homoglutamine (hGln) into myoglobin in response to the four-base selector codon AGGA. Frameshift suppression with hGln does not significantly affect protein yields or cell growth rates, and was shown to be mutually orthogonal with suppression of TAG by a second O-tRNA-ORS pair. This work shows that neither the number of available triplet codons, nor the translational machinery itself, represents a significant barrier to further expansion of the code.

In order to encode unnatural amino acids with quadruplet codons in vivo, one has to generate an orthogonal tRNA (O-tRNA) that uniquely recognizes this codon and a corresponding synthetase that uniquely aminoacylates only this O-tRNA with an unnatural amino acid of interest. Because the anticodon loop of the previously generated orthogonal *M. jannaschii* amber suppressor tRNA is a key recognition element for the cognate synthetase, JYRS, it was difficult to extend this loop to decode a four-base codon. Although it may be possible to relax the anticodon binding specificity of JYRS, it would likely be difficult to construct mutually orthogonal pairs that distinguish amber and four-base suppressors using exclusively the anticodon sequence. Therefore, a system that permits the simultaneous incorporation of two or more different unnatural amino acids into a polypeptide in response to two or more different selector codons are achieved herein using orthogonal pairs with different origins.

This invention provides compositions of and methods for identifying and producing additional orthogonal tRNA-aminoacyl-tRNA synthetase pairs, e.g., O-tRNA/O-RS pairs that can be used to incorporate unnatural amino acids, e.g., homoglutamine. An example O-tRNA of the invention is capable of mediating incorporation of a homoglutamine into a protein that is encoded by a polynucleotide, which comprises a selector codon that is recognized by the O-tRNA, e.g., in vivo. The anticodon loop of the O-tRNA recognizes the selector codon on an mRNA and incorporates its amino acid, e.g., a homoglutamine, at this site in the polypeptide. An orthogonal aminoacyl-tRNA synthetase of the invention preferentially aminoacylates (or charges) its O-tRNA with only a specific unnatural amino acid.

Orthogonal tRNA/Orthogonal Aminoacyl-tRNA Synthetases and Pairs Thereof

Translation systems that are suitable for making proteins that include one or more unnatural amino acids are described in International Publication Numbers WO 2002/086075, entitled "METHODS AND COMPOSITION FOR THE PRODUCTION OF ORTHOGANOL tRNA-AMINOACYL-tRNA SYNTHETASE PAIRS" and WO 2002/085923, entitled "IN VIVO INCORPORATION OF UNNATURAL AMINO ACIDS." In addition, see International Application Number PCT/US2004/011786, filed Apr. 16, 2004. Each of these applications is incorporated herein by reference in its entirety. Such translation systems generally comprise cells (which can be non-eukaryotic cells such as *E. coli*, or eukaryotic cells such as yeast) that include an orthogonal tRNA (O-tRNA), an orthogonal aminoacyl tRNA synthetase (O-RS), and an unnatural amino acid (in the present invention, homoglutamine is an example of such an unnatural amino acid), where the O-RS aminoacylates the O-tRNA with the homoglutamine. An orthogonal pair of the invention includes an O-tRNA, e.g., a suppressor tRNA, a frameshift tRNA, or the like, and an O-RS. Individual components are also provided in the invention.

In general, when an orthogonal pair recognizes a selector codon and loads an amino acid in response to the selector codon, the orthogonal pair is said to "suppress" the selector codon. That is, a selector codon that is not recognized by the translation system's (e.g., cell's) endogenous machinery is not ordinarily translated, which can result in blocking production of a polypeptide that would otherwise be translated from the nucleic acid. An O-tRNA of the invention recognizes a selector codon and includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the sequence listing herein. The O-RS aminoacylates the O-tRNA with an unnatural amino acid of interest, such as a homoglutamine. The cell uses the O-tRNA/O-RS pair to incorporate the unnatural amino acid into a growing polypeptide chain, e.g., via a nucleic acid that comprises a polynucleotide that encodes a polypeptide of interest, where the polynucleotide comprises a selector codon that is recognized by the O-tRNA. In certain desireable aspects, the cell can include an additional O-tRNA/O-RS pair, where the additional O-tRNA is loaded by the additional O-RS with a different unnatural amino acid. For example, one of the O-tRNAs can recognize a four base codon and the other can recognize a stop codon. Alternately, multiple different stop codons or multiple different four base codons can specifically recognize different selector codons.

In certain embodiments of the invention, a cell such as an *E. coli* cell that includes an orthogonal tRNA (O-tRNA), an orthogonal aminoacyl-tRNA synthetase (O-RS), a homoglutamine and a nucleic acid that comprises a polynucleotide that encodes a polypeptide of interest, where the polynucleotide comprises the selector codon that is recognized by the O-tRNA. The translation system can also be a cell-free system, e.g., any of a variety of commercially available "in vitro" transcription/translation systems in combination with an O-tRNA/ORS pair and an unnatural amino acid as described herein.

In one embodiment, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In one aspect, the suppression efficiency of the O-RS and the O-tRNA together is at least about, e.g., 35%, 40%, 45%, 50%, 60%, 75%, 80%, or 90% or more of the suppression efficiency of an orthogonal synthetase pair as set forth in the sequence listings herein.

As noted, the invention optionally includes multiple O-tRNA/O-RS pairs in a cell or other translation system, which allows incorporation of more than one unnatural amino acid, e.g., a homoglutamine and another unnatural amino acid. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon), can further comprise a second orthogonal pair, e.g., leucyl, lysyl, glutamyl, etc., (where the second O-tRNA recognizes a different selector codon, e.g., an opal, four-base codon, or the like). Desirably, the different orthogonal pairs are derived from different sources, which can facilitate recognition of different selector codons.

The O-tRNA and/or the O-RS can be naturally occurring or can be, e.g., derived by mutation of a naturally occurring tRNA and/or RS, e.g., by generating libraries of tRNAs and/or libraries of RSs, from any of a variety of organisms and/or by using any of a variety of available mutation strategies. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) of the invention desireably mediates incorporation of an unnatural amino acid, such as homoglutamine, into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to an O-tRNA comprising or encoded by a polynucleotide sequence as set forth in the O-tRNA sequences in the sequence listing herein.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and O-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatived lacZ construct, where the construct has a corresponding sense codon at desired position rather than a selector codon.

Examples of O-tRNAs of the invention are set forth in the sequence listing herein. See also, the tables, examples and figures herein for sequences of exemplary O-tRNA and O-RS molecules. See also, the section entitled "Nucleic Acid and Polypeptide Sequence and Variants" herein. In an RNA molecule, such as an O-RS mRNA, or O-tRNA molecule, Thymine (T) is replace with Uracil (U) relative to a given sequence (or vice versa for a coding DNA), or complement thereof. Additional modifications to the bases can also be present.

The invention also includes conservative variations of O-tRNAs corresponding to particular O-tRNAs herein. For example, conservative variations of O-tRNA include those molecules that function like the particular O-tRNAs, e.g., as in the sequence listing herein and that maintain the tRNA L-shaped structure by virtue of appropriate self-complementarity, but that do not have a sequence identical to those, e.g., in the sequence listing, figures or examples herein (and, desireably, are other than wild type tRNA molecules). See also, the section herein entitled "Nucleic acids and Polypeptides Sequence and Variants."

The composition comprising an O-tRNA can further include an orthogonal aminoacyl-tRNA synthetase (O-RS), where the O-RS preferentially aminoacylates the O-tRNA with an unnatural amino acid such as homoglutamine. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell. See also, the section herein entitled "Orthogonal aminoacyl-tRNA synthetases."

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TPC arm or loop, other regions of the tRNA molecule, or a combination thereof. Typically, mutations in a tRNA include mutating the anticodon loop of each member of the library of mutant tRNAs to allow recognition of a selector codon. The method can further include adding an additional sequence (CCA) to a terminus of the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the similarity (and/or inferred homology) of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a prokaryotic organism, a synthetase and/or a tRNA is chosen that does not display close sequence similarity to prokaryotic organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (S) that is endogenous to the cell. This provides a pool of tRNAs that are orthogonal to the cell of the first species.

In certain embodiments, in the negative selection, a selector codon(s) is introduced into a polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal tRNA, which cannot be efficiently charged by endogenous *E. coli* synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a 4-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest, are sensitive to the antibiotic. Therefore, tRNAs that: (i) are not substrates for endogenous host, e.g., *Escherichia coli*, synthetases; (ii) can be aminoacylated by the synthetase of interest; and (iii) are functional in translation, survive both selections.

Accordingly, the same marker can be either a positive or negative marker, depending on the context in which it is screened. That is, the marker is a positive marker if it is screened for, but a negative marker if screened against.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In one aspect of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that loads an unnatural amino acid such as homoglutamine in response to a selector codon. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See also, Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in International patent applications WO 2002/086075, entitled "Methods and compositions for the production of orthogonal tRNA-aminoacyltRNA synthetase pairs;" and, U.S. Ser. No. 60/479,931, and 60/496,548 entitled "EXPANDING THE EUKARYOTIC GENETIC CODE." See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100(10): 5676-5681.

Orthogonal Aminoacyl-tRNA Synthetase (O-RS)

An O-RS of the invention preferentially aminoacylates an O-tRNA with an unnatural amino acid such as homoglutamine in vitro or in vivo. An O-RS of the invention can be provided to the translation system, e.g., a cell, by a polypeptide that includes an O-RS and/or by a polynucleotide that encodes an O-RS or a portion thereof. For example, an example O-RS comprises an amino acid sequence as set forth in the sequence listing and examples herein, or a conservative variation thereof. In another example, an O-RS, or a portion thereof, is encoded by a polynucleotide sequence that encodes an amino acid comprising sequence in the sequence listing or examples herein, or a complementary polynucleotide sequence thereof. See, e.g., the tables and examples herein for sequences of exemplary O-RS molecules. See also, the section entitled "Nucleic Acid and Polypeptide Sequence and Variants" herein.

Methods for identifying an orthogonal aminoacyl-tRNA synthetase (O-RS), e.g., an O-RS, for use with an O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes an (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled amino acid or unnatural amino acid, e.g., a labeled homoglutamine). The active RS that more efficiently aminoacylates the second set of tRNAs compared to the first set of tRNAs is typically selected, thereby providing an efficient (optimized) orthogonal aminoacyl-tRNA synthetase for use with the O-tRNA. An O-RS, identified by the method, is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, WO 2002/085923, entitled "IN VIVO INCORPORATION OF UNNATURAL AMINO ACIDS;" and International Application Number PCT/US2004/011786, filed Apr. 16, 2004.

Identified O-RS can be further manipulated to alter substrate specificity of the synthetase, so that only a desired unnatural amino acid, e.g., a homoglutamine, but not any of the common 20 amino acids, are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential posit on(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., a homoglutamine. In one aspect of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in WO 2002/086075 entitled "Methods and compositions for the production of orthogonal tRNA-aminoacyltRNA synthetase pairs;" and International Application Number PCT/US2004/011786, filed Apr. 16, 2004.

Source and Host Organisms

The translational components of the invention can be derived from non-eukaryotic organisms. For example, the orthogonal O-tRNA can be derived from a non-eukaryotic organism (or a combination of organisms), e.g., an archaebacterium, such as *Methanococcus jannaschii*, *Methanobacterium thermoautotrophicum*, *Halobacterium* such as *Haloferax volcanii* and *Halobacterium* species NRC-1,

*Archaeoglobus fulgidus, Pyrococcus furiosus, Pyrococcus horikoshii, Aeuropyrum pernix, Methlanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a eubacterium, such as *Escherichia coli, Thermus thermophilus, Bacillus stearothermphilus*, or the like, while the orthogonal O-RS can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms. In one preferred example embodiment, the lysyl synthetase/tRNA pair of the archaen *Pyrococcus horikoshii* is used as an orthogonal pair, e.g., in an *E. coli*-based translation system. As described herein, this pair can be modified to recognize a four base selector codon and can be modified to charge the O-tRNA with an unnatural amino acid such as homoglutamine. This orthogonal pair (or modified forms thereof) can also be combined with previously described orthogonal pairs, e.g., those derived from *Methanococcus jannaschii*, e.g., that are modified to recognize stop selector codons. This provides for production of proteins that comprise two different unnatural amino acids in a translation system of interest by including a coding nucleic acid for such proteins that include two or more selector codons that are each recognized by an O-tRNA/O-RS pair.

The O-tRNA, O-RS or O-tRNA/O-RS pair can be selected or screened in vivo or in vitro and/or used in a cell, e.g., a non-eukaryotic cells, or eukaryotic cells, to produce a polypeptide with a homoglutamine or other unnatural amino acid of interest. A non-eukaryotic cell can be from any of a variety of sources, e.g., a eubacterium, such as *Escherichia coli, Thermus thermophilus, Bacillus stearothermphilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like. A eukaryotic cell can be from any of a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of cells with translational components of the invention are also a feature of the invention.

See also, International Application Number PCT/US2004/011786, filed Apr. 16, 2004, for screening O-tRNA and/or O-RS in one species for use in another species.

Selector Codons

Selector codons of the invention expand the genetic codon framework of the protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon (e.g., AGGA), a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple different unnatural amino acids, using these different selector codons.

In one embodiment, the methods involve the use of a selector codon that is a stop codon for the incorporation of a homoglutamine in vivo in a cell. For example, an O-tRNA is produced that recognizes a four base selector codon and is aminoacylated by an O-RS with a homoglutamine. This O-tRNA is not recognized by the translation system's endogenous aminoacyl-tRNA synthetases. Conventional site-directed mutagenesis can be used to introduce the selector codon at the site of interest in a target polynucleotide encoding a polypeptide of interest. See also, e.g., Sayers, J. R., et al. (1988), "5',3' Exonuclease in phosphorothioate-based oligonucleotide-directed mutagenesis." *Nucleic Acids Res,* 791-802. When the O-RS, O-tRNA and the nucleic acid that encodes a polypeptide of interest are combined, e.g., in vivo, the homoglutamine is incorporated in response to the selector codon to give a polypeptide containing the homoglutamine at the specified position.

The incorporation of unnatural amino acids such as homoglutamine, in vivo, can be done without significant perturbation of the host cell. For example, in non-eukaryotic cells, such as *Escherichia coli*, because the suppression efficiency of a stop selector codon, the UAG codon, depends upon the competition between the O-tRNA, e.g., the amber suppressor tRNA, and release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for a UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present that modulate release factor action, e.g., reducing agents such as dithiothretiol (DTT).

Unnatural amino acids, including, e.g., homoglutamines can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNA$_{Arg}$, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC, and the like. Methods of the invention include using extended codons based on frameshift suppression. Four or more base codons can insert, e.g., one or multiple unnatural amino acids, such as a homoglutamine, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach, in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.* 121: 34. C(3CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of $tRNA^{Leu}$ derivatives with NCUA anticodons to suppress UAGN codons (N can be U, A, G, or C), and found that the quadruplet UAGA can be decoded by a $tRNA^{Leu}$ with a UCUA anticodon with an efficiency of 13 to 26% with little decoding in the 0 or −1 frame. See Moore et al., (2000) *J. Mol. Biol.,* 298:195. In one embodiment, extended codons based on rare codons or nonsense codons can be used in invention, which can reduce missense read through and frameshift suppression at other unwanted sites. In the examples herein, an orthogonal pair that recognizes an AGGA selector codon and that inserts a homoglutamine during protein translation is described.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.,* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.,* 122:10714. Because extended codons and unnatural codons are intrinsically orthogonal to natural codons, the methods of the invention can take advantage of this property to generate orthogonal tRNAs for them.

A translational bypassing system can also be used to incorporate a homoglutamine or other unnatural amino acid into a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I;

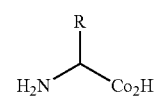

I

An unnatural amino acid is typically any structure having Formula I wherein the R group is any substituent other than one used in the twenty natural amino acids. See e.g., *Biochemistry* by L. Stryer, $3^{rd}$ ed. 1988, Freeman and Company, New York, for structures of the twenty natural amino acids. Note that, the unnatural amino acids of the invention can be naturally occurring compounds other than the twenty alpha-amino acids above (or, of course, artificially produced synthetic compounds).

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest in incorporating unnatural amino acids into proteins it to have the ability to incorporate a homoglutamine. In other unnatural amino acids, for example, R in Formula I optionally comprises an alkyl-, aryl-, acyl-, keto-, azido-, hydroxyl-, hydrazine, cyano-, halo-, hydrazide, alkenyl, alkynyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, redox-active amino acids, amino thioacid containing amino acids, and amino acids containing one or more toxic moiety. In some embodiments, the unnatural amino acids have a photoactivatable cross-linker. In one embodiment, the unnatural amino acids have a saccharide moiety attached to the amino acid side chain and/or other carbohydrate modification.

In addition to unnatural amino acids that contain novel side chains, unnatural amino acids also optionally comprise modified backbone structures, e.g., as illustrated by the structures of Formula II and III:

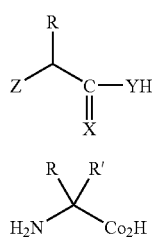

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid. Additional unnatural amino acid structures of the invention include homo-beta-type structures, e.g., where there is, e.g., a methylene or amino group sandwiched adjacent to the alpha carbon, e.g., isomers of homo-beta-tyrosine, alpha-hydrazino-tyrosine. See, e.g.,

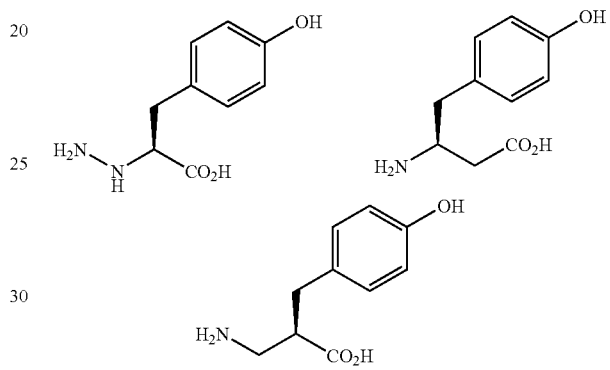

Many unnatural amino acids are based on natural amino acids, such as tyrosine, glutamine, phenylalanine, and the like. For example, tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenyalanines, and meta-substituted phenylalanines, wherein the substituent comprises a hydroxy group, a methoxy group, a methyl group, an allyl group, an aldehyde or keto group, or the like. Specific examples of unnatural amino acids include, but are not limited to, homoglutamine, a 3,4-dihydroxy-L-phenylalanine, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided in, for example, FIGS. 16, 17, 18, 19, 26, and 29 of WO 2002/085923 entitled "In vivo incorporation of unnatural amino acids."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.*, 38, 4660-4669; King, F. E. & Kidd, D. A. A. (1949) *A New Synthesis of Glutamine and of γ-Dipeptides of Glutamic Acid from Phthylated Intermediates. J. Chem. Soc.* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of 4-Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L-and D-a-Amino-Adipic Acids, L-a-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also International Application Number PCT/US03/41346, entitled "Protein Arrays," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., toxicity assays in, e.g., International Application Number PCT/US03/41346, entitled "Protein Arrays," filed on Dec. 22, 2003; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 213944. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave & Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "Non-Stochastic Generation of Genetic Vaccines and Enzymes" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology*, 20(7): 707-712; and Zhang et al. (2002) "Genome shuffling leads to rapid phenotypic improvement in bacteria" Nature, February 7, 415(6872): 644646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of Corynebacterium 2,5-diketo-D-gluconic acid reductase or use in vitamin C biosynthesis" *Biochemistry*, 41(20), 6226-36; Selivonova et al. (2001) "Rapid Evolution of Novel Traits in Microorganisms" *Applied and Environmental Microbiology*, 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating Homoglutamine

The invention provides compositions and methods of producing orthogonal components for incorporating a homoglutamine into a growing polypeptide chain in response to a selector codon, e.g., stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate homoglutamines into growing polypeptide chains.

A composition of the invention includes an orthogonal aminoacyl-tRNA synthetase (O-RS), where the O-RS preferentially aminoacylates an O-tRNA with a homoglutamine. In certain embodiments, the O-RS comprises an amino acid sequence of PhKRS, E444G, PhΔAD, an I41 and/or S268 mutant of PhΔAD, or a conservative variation thereof. In certain embodiments of the invention, the O-RS preferentially aminoacylates the O-tRNA with an efficiency of at least 50% of the efficiency of an I41 and/or S268 mutation of PhΔAD.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, a 80%, or a 90% or more suppression efficiency in the presence of a cognate synthetase in response to a selector codon as compared to the O-tRNA comprising or encoded by a polynucleotide sequence as set forth in the sequence listings and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA lacking the O-RS, In one aspect, the suppression efficiency of the O-RS and the O-tRNA together is at least 45% of the suppression efficiency of an orthogonal tyrosyl-tRNA synthetase pair derived from *Methanococcus jannaschii*.

A composition that includes an O-tRNA can optionally include a cell (e.g., a non-eukaryotic cell, such as an *E. coli* cell and the like, or a eukaryotic cell), and/or a translation system.

A cell (e.g., a non-eukaryotic cell, or a eukaryotic cell) comprising a translation system is also provided by the invention, where the translation system includes an orthogonal-tRNA (O-tRNA); an orthogonal aminoacyl-tRNA synthetase (O-RS); and, a homoglutamine. Typically, the O-RS preferentially aminoacylates the O-tRNA with an efficiency of at least 50% of the efficiency of an I41 and/or S268 mutation of PhΔAD. The O-tRNA recognizes the first selector codon, and the O-RS preferentially aminoacylates the O-tRNA with the homoglutamine. In one embodiment, the O-tRNA comprises or is encoded by a polynucleotide sequence as set forth in SEQ ID NO.: 24 or SEQ ID NO.: 26, or a complementary polynucleotide sequence thereof. In one embodiment, the O-RS comprises an amino acid sequence of PhKRS, E444G, PhΔAD, an I41 and/or S268 mutant of PhΔAD, or a conservative variation thereof.

A cell of the invention can optionally further comprise an additional different O-tRNA/O-RS pair and a second unnatural amino acid, e.g., where this O-tRNA recognizes a second selector codon and this O-RS preferentially aminoacylates the O-tRNA with the second unnatural amino acid amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention includes an *E. coli* cell that includes an orthogonal-tRNA (O-tRNA), an orthogonal aminoacyl-tRNA synthetase (O-RS), a homoglutamine, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with an efficiency of at least 50% of the efficiency of a polypeptide comprising an amino acid sequence of any listed O-RS sequence herein.

In certain embodiments of the invention, an O-tRNA of the invention comprises or is encoded by a polynucleotide sequence as set forth in the sequence listings or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention includes an artificial (e.g., manmade, and not naturally occurring) polynucleotide comprising a nucleotide sequence encoding a polypeptide as set forth in the sequence listings herein, and/or is complementary to or that polynucleotide sequence. A polynucleotide of the invention can also includes a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that are orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges a homoglutamine onto an O-tRNA are also provided. For example, methods include subjecting to selection a population of cells of a first species, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., a non-eukaryotic cell, such as an *E. coli* cell or the like, or a eukaryotic cell) with a homoglutamine at a specified position are also a feature of the invention. For example, a method includes growing, in an appropriate medium, a cell, where the cell comprises a nucleic acid that comprises at least one selector codon and encodes a protein, providing the homoglutamine, and incorporating the homoglutamine into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the homoglutamine. A protein produced by this method is also a feature of the invention.

The invention also provides compositions that include proteins, where the proteins comprise, e.g., a homoglutamine. In certain embodiments, the protein comprises an amino acid sequence that is at least 75% identical to that of a known protein, e.g., a therapeutic protein, a diagnostic protein, an industrial enzyme, or portion thereof. Optionally, the composition comprises a pharmaceutically acceptable carrier.

Nucleic Acid and Polypeptide Sequence and Variants

As described above and below, the invention provides for nucleic acid polynucleotide sequences, e.g., O-tRNAs and O-RSs, and polypeptide amino acid sequences, e.g., O-RSs, and, e.g., compositions, systems and methods comprising said sequences. Examples of said sequences, e.g., O-tRNAs and O-RSs are disclosed herein (see the sequence listings and examples herein). However, one of skill in the art will appreciate that the invention is not limited to those exact sequences, e.g., as in the Examples and listing. One of skill will appreciate that the invention also provides, e.g., many related and unrelated sequences with the functions described herein, e.g., encoding an appropriate O-tRNA or an O-RS.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in the sequence listings; a polynucleotide that is complementary to or that encodes a polynucleotide sequence thereof. A polynucleotide of the invention also includes a polynucleotide that encodes an amino acid sequence comprising any of those in the sequence listings or examples herein. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA) or any tRNA or coding nucleic acid thereof in a listing or example herein. A polynucleotide also includes an artificial polynucleotide that is, e.g., at least 75%, at least 80%, at least 90%, at least 95%, at least 98% or more identical to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally similar sequence are included in the invention. Variants of the nucleic acid polynucleotide sequences, wherein the variants hybridize to at least one disclosed sequence and recognize a selector codon, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with an amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

| Nonpolar and/or Aliphatic Side Chains | Polar, Uncharged Side Chains | Aromatic Side Chains | Positively Charged Side Chains | Negatively Charged Side Chains |
| --- | --- | --- | --- | --- |
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Nucleic Acid Hybridization

Comparative hybridization can be used to identify nucleic acids of the invention, such as those in the sequence listings herein, including conservative variations of nucleic acids of the invention, and this comparative hybridization method is a one method of distinguishing nucleic acids of the invention from unrelated nucleic acids. In addition, target nucleic acids which hybridize to a nucleic acid represented by those of the sequence listing under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel, supra. Hames and Higgins (1995) Gene Probes 1 IRL Press at Oxford University Press, Oxford, England, (Hames and Higgins 1) and Hames and Higgins (1995) Gene Probes 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any previously known tRNA or RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any previously known RS sequence.

The invention also provides target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more homoglutamine, e.g. unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation A) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3rd Ed.). Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include homoglutamines, orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode a homoglutamine in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature,* 328:731 (1987); Schneider, B., et al., *Protein Expr. Purif* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition Scientific American Books, NY*. In addition, essentially any nucleic acid (and virtually any labeled nucleic acid, whether standard or nonstandard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Proteins or polypeptides of interest, e.g., having at least one homoglutamine, are a feature of the invention, as are polypeptides comprising two or more different unnatural amino acids. An excipient (e.g., a pharmaceutically acceptable excipient) can also be present with the protein. Optionally, a protein of the invention will include a post-translational modification.

Methods of producing a protein in a cell with a homoglutamine or other unnatural amino acid at a specified position are also a feature of the invention. For example, a method includes growing, in an appropriate medium, the cell, where the cell comprises a nucleic acid that comprises at least one selector codon and encodes a protein; and, providing the homoglutamine or other unnatural amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the homoglutamine or other unnatural amino acid. In certain embodiments, the O-tRNA comprises at least about, e.g., a 45%, a 50%, a 60%, a 75%, a 80%, or a 90% or more suppression efficiency in the presence of a cognate synthetase in response to the selector codon as compared to the O-tRNA comprising or encoded by a polynucleotide sequence as set forth in the sequence listing and examples herein. A protein produced by this method is also a feature of the invention.

The invention also provides compositions that include proteins, where the proteins comprise a homoglutamine. In certain embodiments, the protein comprises an amino acid sequence that is at least 75% identical to that of a target protein such as a therapeutic protein, a diagnostic protein, an industrial enzyme, or portion thereof, e.g., differing from the target protein by introduction of one or more unnatural amino acid such as homoglutamine.

The compositions of the invention and compositions made by the methods of the invention optionally are present in a cell. The O-tRNA/O-RS pairs or individual components of the invention can then be used in a host system's translation machinery, which results in a homoglutamine being incorporated into a protein. International Application Number PCT/US2004/011786, filed Apr. 16, 2004, entitled "Expanding the Eukaryotic Genetic Code;" and, WO 2002/085923, entitled "IN VIVO INCORPORATION OF UNNATURAL AMINO ACIDS" describe this process, and are incorporated herein by reference. For example, when an O-tRNA/O-RS pair is introduced into a host, e.g., *Escherichia coli*, the pair leads to the in vivo incorporation of homoglutamine, e.g., a synthetic amino acid, such as derivative of a tyrosine or phenylalanine amino acid, which can be exogenously added to the growth medium, into a protein, in response to a selector codon. Optionally, the compositions of the present invention can be in an in vitro translation system, or in an in vivo system(s).

A cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises a homoglutamine or multiple unnatural amino acids, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one homoglutamine is a feature of the invention.

The incorporation of a homoglutamine or other unnatural amino acids can be done to, e.g., tailor changes in protein structure and/or function, e.g., to change size, acidity, nucleophilicity, hydrogen bonding, hydrophobicity, accessibility of protease target sites, target to a moiety (e.g., for a protein array), etc. Proteins that include a homoglutamine can have enhanced or even entirely new catalytic or physical properties. For example, the following properties are optionally modified by inclusion of a homoglutamine or other unnatural amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one homoglutamines are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652. In addition, one or more unnatural amino acids can be incorporated into a polypeptide to provide a molecular tag, e.g., to fix the polypeptide to a solid support. See e.g., "PROTEIN ARRAYS" by Wang and Schultz, filed Dec. 22, 2003, international publication number WO2004/058946 for an extended discussion of methods of making arrays using polypeptides that comprise unnatural amino acids.

In one aspect of the invention, a composition includes at least one protein with at least one, e.g., at least two, at least three, at least four, at least five, at least six, at least seven, at least eight, at least nine, or at least ten or more unnatural amino acids, e.g., homoglutamines and/or other unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the homoglutamine. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes an unnatural amino acid such as a homoglutamine, or that encodes multiple different unnatural amino acids (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more homoglutamine can be found, but not limited to, those in International Application Number PCT/US2004/011786, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more homoglutamines include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of homoglutamines described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more homoglutamines) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4/VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one homoglutamine are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2003 catalogue and price list), and the corresponding protein sequences and genes and, typically, many variants thereof, are well-known (see, e.g., Genbank). Any of them can be modified by the insertion of one or more homoglutamine or other unnatural amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, e.g., homoglutamines), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more homoglutamine or other unnatural amino acid of the invention. For example, the invention can include substituting one or more natural amino acids in one or more vaccine proteins with a homoglutamine, e.g., in proteins from infectious fungi, e.g., *Aspergillus, Candida* species; bacteria, particularly *E. coli*, which serves a model for pathogenic bacteria, as well as medically important bacteria such as Staphylococci (e.g., *aureus*), or Streptococci (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., vaccinia; Picornaviruses, e.g. polio; Togaviruses, e.g., rubella; Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for homoglutamine or other unnatural amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a homoglutamine. For example, a nucleic acid for a protein of interest is mutagenized to include one or more selector codon, providing for the insertion of the one or more homoglutamines. The invention includes any such variant, e.g., mutant, versions of any protein, e.g., including at least one homoglutamine. Similarly, the invention also includes corresponding nucleic acids, i.e., any nucleic acid with one or more selector codon that encodes one or more homoglutamine.

To make a protein that includes a homoglutamine, one can use host cells and organisms that are adapted for the in vivo incorporation of the homoglutamine via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., comprising homoglutamines in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in U.S. Ser. No. 60/479,931, 60/463,869, and 60/496,548 entitled "Expanding the Eukaryotic Genetic Code;" WO 2002/085923, entitled "IN VIVO INCORPORATION OF UNNATURAL AMINO ACIDS;" patent application entitled "Glycoprotein synthesis" filed Jan. 16, 2003, U.S. Ser. No. 60/441,450; and patent application entitled "Protein Arrays," U.S. Ser. No. 60/435,82 filed on Dec. 22, 2002.

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in a homoglutamine being incorporated into a protein. The patent application "In vivo Incorporation of Unnatural Amino Acids", WO 2002/085923 by Schultz, et al. describes this process and is incorporated herein by reference. For example, when an O-tRNA/O-RS pair is introduced into a host, e.g., *Escherichia coli*, the pair leads to the in vivo incorporation of a homoglutamine, which can be exogenously added to the growth medium, into a protein, e.g., myoglobin or a therapeutic protein, in response to a selector codon, e.g., an amber nonsense codon. Optionally, the compositions of the invention can be in an in vitro translation system, or in an in vivo system(s). Proteins with the homoglutamine can be used as therapeutic proteins and can be used to facilitate studies on protein structure, interactions with other protein, electron transfer processes in proteins, and the like.

Kits

Kits are also a feature of the invention. For example, a kit for producing a protein that comprises at least one homoglutamine in a cell is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes a homoglutamine. In another embodiment, the kit further comprises instructional materials for producing the protein. Any composition, system or device of the invention can also be associated with appropriate packaging materials (e.g., containers, etc.) for production in kit form.

EXAMPLES

The following examples are offered to illustrate, but not to limit the claimed invention. One of skill will recognize a variety of non-critical parameters that may be altered without departing from the scope of the claimed invention.

Example 1

Production of Orthogonal Synthetase/tRNA Pair Derived from Archael tRNA$^{LYS}$

An orthogonal synthetase-tRNA pair was constructed from the lysyl-tRNA synthetase of *Pyrococcus horikoshii*. Using an amber suppressor tRNA derived from the consensus of a multiple sequence alignment of archeal tRNAlys sequences, 32% amber suppression was observed in β-galactosidase assays. As such, this pair is a highly efficient system for the selective incorporation of unnatural amino acids into protein in *E. coli*.

The expansion of the genetic code of an organism to include additional amino acids beyond the common twenty requires a minimum of two novel genes: an aminoacyl-tRNA synthetase that selectively activates the unnatural amino acid and does not transfer the amino acid to endogenous tRNAs; and a cognate orthogonal tRNA that accepts the unnatural amino acid and is not charged by endogenous synthetases (Furter, (1998) *Protein Sci.*, 7:419-426). In addition, the tRNA deliver the amino acid in response to a noncoding codon, e.g., a nonsense or frameshift codon. Variants of a *Methanococcus jannaschii* tyrosyl tRNA-synthetase and cognate amber suppressor tRNA pair (Wang et al., (2000) *J. Am. Chem. Soc.*, 122:5010-5011; Wang et al., (2001) *Science*, 292:498-500) have been identified that fulfill these criteria, and have been used to efficiently incorporate a variety of unnatural amino acids, including keto-containing (Wang et al., (2003) *Proc. Natl. Acad. Sci. U.S.A.*, 100:56-61) and photo-crosslinking amino acids, into proteins in *E. coli* with high fidelity (Chin et al., (2002) *Proc. Natl. Acad. Sci. U.S.A.*, 99:11020-11024; Chin and Schultz, (2002) *ChemBioChem*, 3:1135-1137). Broadening the scope and number of unnatural amino acids that can be genetically encoded will likely use new orthogonal synthetase-tRNA pairs and new codons to encode them (Magliery et al., (2001) *J. Mol. Biol.*, 307:755-769; Anderson et al., (2002) *Chem. Biol.*, 9:237-244).

Recently a novel approach was taken to construct an orthogonal pair derived from the *Methanobacterium thermoautotrophicum* leucyl-tRNA synthetase and cognate orthogonal amber, opal, and four-base suppressor tRNAs derived from *Halobacterium* sp. NRC-1 (Anderson and Schultz, (2003) *Biochemistry*, 42(32):9598-608). The design of these suppressor tRNAs from the consensus sequence of a multiple sequence alignment of archaeal leucyl-tRNAs provided efficient, orthogonal frameshift and opal suppressors. Robust orthogonal suppressor tRNAs had CU(X)XXXAA anticodon loops (where (X)XX is the reverse complement sequence of the codon) and no mispaired bases in stem regions. We now report the use of this "consensus suppressor" strategy in the rational design of an efficient orthogonal synthetase-tRNA pair derived from archaeal tRNA$^{Lys}$ sequences and the lysyl-tRNA synthetase of the archaean *Pyrococcus horikoshii*.

This tRNA/synthetase pair has a number of attractive features for the construction of an orthogonal suppressor pair in *E. coli*. An orthogonal tRNA for use in *E. coli* should not cross-react with *E. coli* aminoacyl-tRNA synthetases. Despite the similarity between the tRNA$^{Lys}$ sequences of prokaryotes and archaea, the discriminator base 73 is A in prokaryotes and G in archaea (Ibba et al., (1999) *Proc. Natl. Acad. Sci. U.S.A.* 96:418-423), which prevents archaeal tRNA$^{Lys}$s from serving as substrates for *E. coli* synthetases.

Indeed, *E. coli* total cell lysates were found to poorly acylate tRNA from the archaean *Halobacterium cutirubrum* (Kwok and Wong, (1980) *Can. J. Biochem.,* 58:213-218). To construct suppressor tRNAs, changes to the sequence of the anticodon are allowed without adversely affecting aminoacylation activity. Studies on tRNA recognition by the lysyl-tRNA synthetase of the archaean *Pyrococcus horikoshii* (PhKRS) (Terada et al., (2002) *Nat. Struct. Biol.,* 9:257-262) revealed that the anticodon can be altered without impairing recognition of the tRNA. Therefore, it is likely that suppressor tRNAs for codons such as the amber nonsense codon, UAG, can be constructed from these tRNAs. Finally, the crystal structure of the archaeal type I lysyl-tRNA synthetase, PhKRS, is available (Terada et al., (2002) *Nat. Struct. Biol.,* 9:257-262) to facilitate changes in the amino acid specificity of the aminoacyl-tRNA synthetase.

Figure 1:
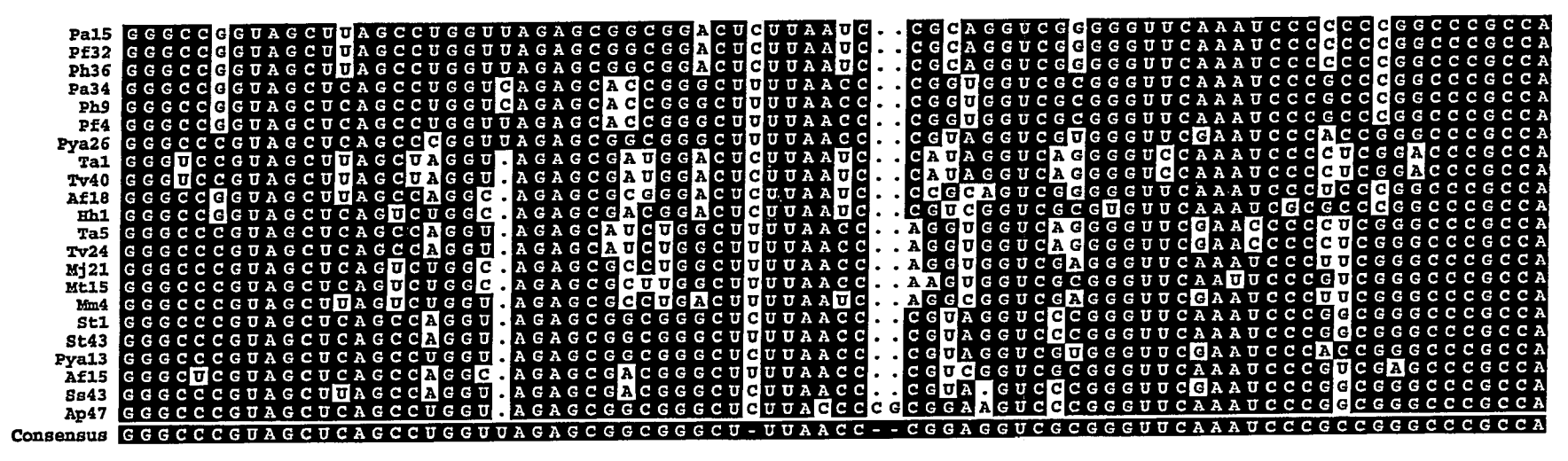
Figure 2B:
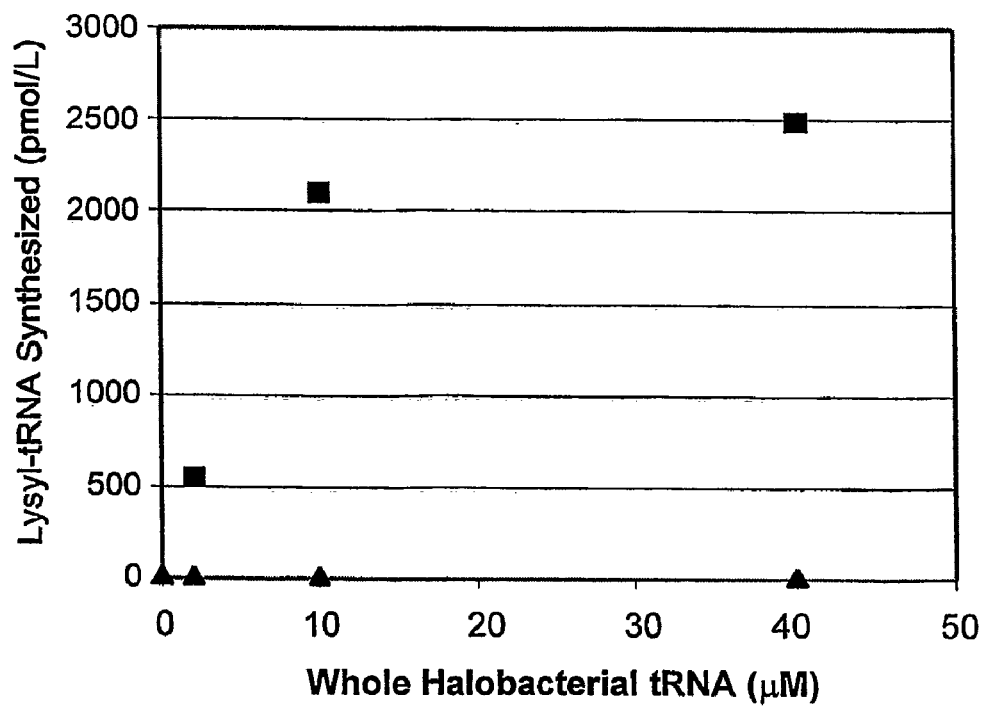

To determine whether PhKRS is orthogonal in *E. coli*, it was useful to demonstrate that the synthetase does not charge *E. coli* tRNA to any significant extent. The gene for PhKRS was PCR-amplified from genomic DNA, inserted into the plasmid pBAD-Myc/HisA (Invitrogen), and overexpressed. The resulting PhKRS protein was purified to homogeneity. Aminoacylation assays were performed on whole tRNA from *Halobacterium* sp. NRC-1 or *E. coli*. The sequences of the tRNA$^{Lys}$s from *Halobacterium* sp. NRC-1 and *Pyrococcus horikoshii* are highly homologous (FIG. 1). The halobacterial tRNA was, therefore, anticipated to be readily charged by PhKRS. Indeed, PhKRS charges a 14-fold greater amount of whole halobacterial tRNA than whole *E. coli* tRNA in 20 minutes (FIG. 2; 10 µM [tRNA]). Although PhKRS is able to weakly charge *E. coli* tRNA, the rate is 28-fold lower than the activity of the *E. coli* synthetase towards the same concentration of whole *E. coli* tRNA and only 7-fold over background charging. Furthermore, the highly homologous archaeal synthetase from *M. mariplaudis* could only weakly complement a lysS/lysU double mutant deficient in *E. coli* lysyl-tRNA synthetase (Ibba et al., (1999) *Proc. Natl. Acad. Sci. U.S.A.* 96:418-423). Therefore, PhKRS is likely to compete poorly with endogenous *E. coli* synthetases for charging of *E. coli* tRNAs in vivo.

To further characterize the orthogonality of PhKRS, we attempted to insert the PhKRS gene into the constitutive expression vector, pKQ. This plasmid contains the ribosome binding site, multiple cloning site, and rrnB terminator from plasmid pBAD-Myc/HisA (Invitrogen) under control of the constitutive glutamine promoter. The plasmid also contains a ColE1 origin of replication, and a kanamycin resistance selectable marker for plasmid maintenance. Unfortunately, the wild-type PhKRS gene appeared to be toxic when expressed constitutively. However, a serendipitous E444G mutant (plasmid pKQ-PhE444G) was identified that exhibited reduced toxicity when expressed in *E. coli*. The mechanism by which the E444G mutation alleviates apparent toxicity in this system has not been established. One possibility is that the mutation prevents the low-level cross-species mischarging of *E. coli* tRNA observed in vitro.

Figure 3:
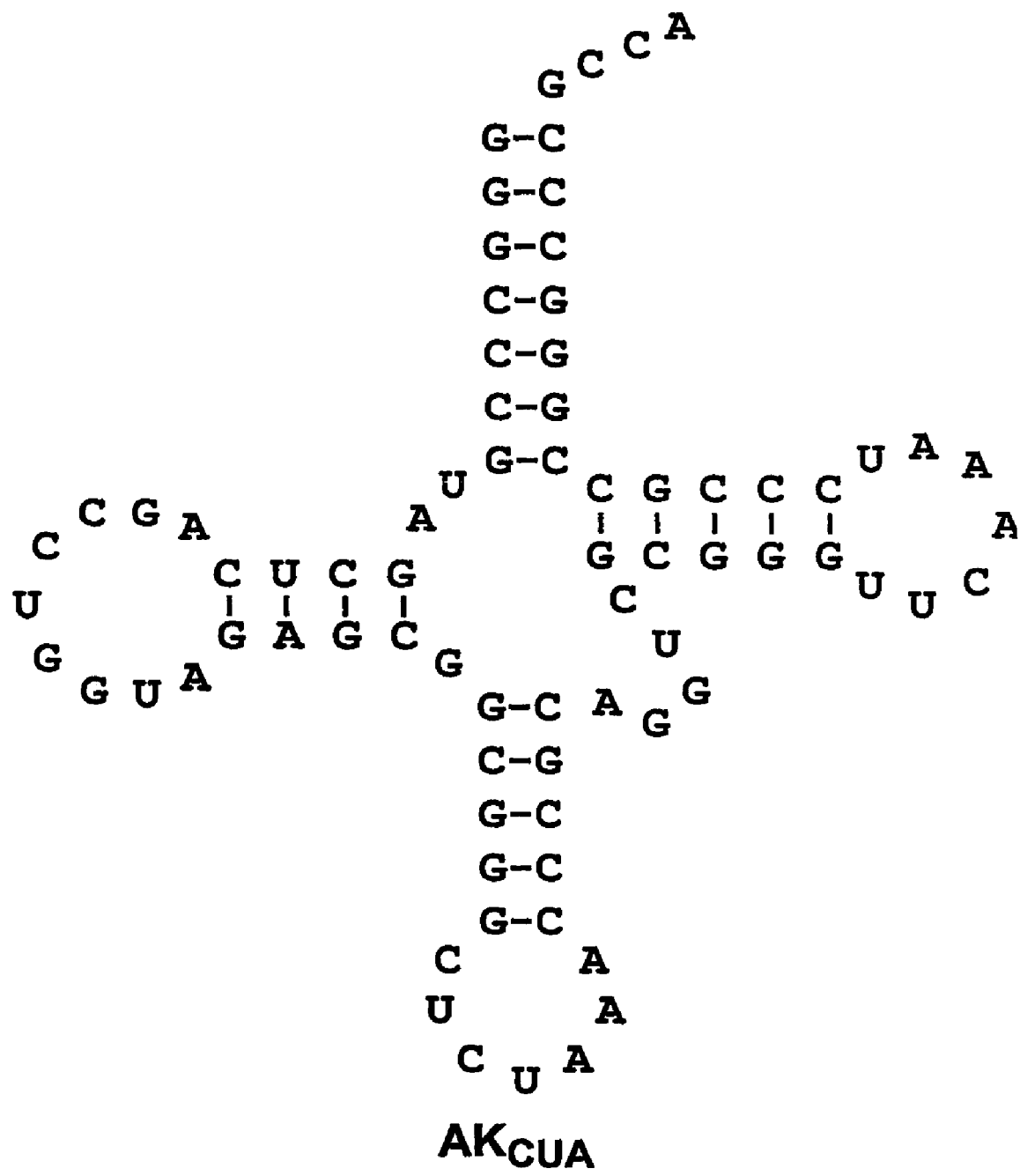
FIG. 3 schematically illustrates a consensus-derived amber suppressor tRNA (SEQ ID NO:24). The consensus for the family of archaeal tRNA$^{Lys}$ sequences is represented in a cloverleaf configuration. The anticodon loop was changed from the consensus to CUCUAAA to generate AK$_{CUA}$.
Figure 4:
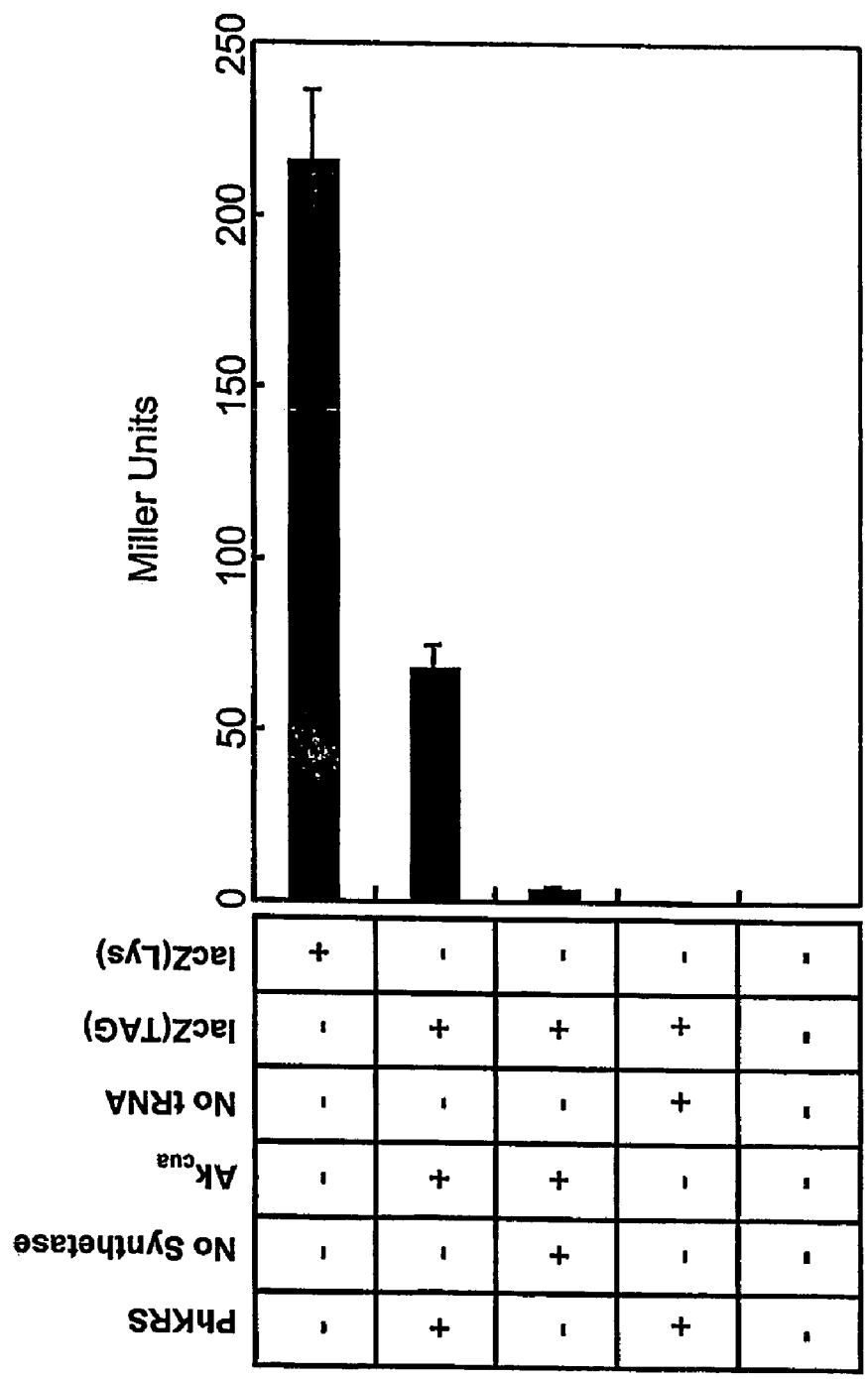
FIG. 4 provides a histogram illustrating in vivo activity of the orthogonal synthetase-tRNA pair. β-Galactosidase activity was determined in quadruplicate for GeneHogs cells (Invitrogen) transformed with the plasmids shown, or no plasmids. The E444G mutant of PhKRS was expressed from plasmid pKQ. Plasmid pKQ was used for samples containing no synthetase. AK$_{CUA}$ was expressed from plasmid pACGFP, and plasmid pACGFP was used for samples containing no tRNA. The lacZ reporter genes were from plasmid pLASC-lacZ. Cells were grown in 2YT media with the appropriate antibiotics to an OD$_{600}$ of 0.5 then assayed by the methods of Miller (Miller, (1972) *Experiments in molecular genetics*, Cold Spring Harbor Laboratory, Cold Spring Harbor, N.Y.).

The next step involved the construction of a nonsense suppressor tRNA that could be charged by PhKRS. The weak anticodon binding determinants observed for PhKRS suggest that the enzyme should accept tRNAs with a variety of anticodon sequences (Terada et al., (2002) *Nat. Struct. Biol.,* 9:257-262). Because amber suppression is the best-characterized and most efficient form of suppression in *E. coli* (Anderson et al., (2002) *Chem. Biol.,* 9:237-244), we constructed an orthogonal archaeal amber suppressor tRNA, AK$_{CUA}$, from the consensus sequence (Anderson and Schultz, (2003) *Biochemistry,* 42(32):9598-608). A multiple sequence alignment of all archaeal tRNA$^{Lys}$ sequences from available genomic sequences was performed using the GCG program pileup (FIG. 1). The consensus sequence of the aligned tRNAs was determined and a cloverleaf representation was generated (FIG. 3). The sequence was then inspected for non-canonical base pairs or base mismatches in stem regions, which have been found to reduce suppressor efficiency (Hou et al., (1992) *Biochemistry,* 31:4157-4160). No such mispairs were present in the tRNA$^{Lys}$ consensus sequence. The anticodon loop was then changed to CUCUAAA since this sequence has been found to be optimal for amber suppression (Yarus et al., (1986) *J. Mol. Biol.* 192:235-255). The designed tRNA sequence was constructed by the overlap extension of synthetic oligonucleotides (Genosys) and inserted between the EcoRI and PstI restriction sites of plasmid pACGFP (Magliery et al., (2001) *J. Mol. Biol.,* 307: 755-769) under the control of the strong, constitutive lpp promoter. The resulting plasmid, PAC-AK$_{CUA}$, also contains the p15A origin of replication and a chloramphenicol resistance selectable marker.

To examine the suppression efficiency of this potential orthogonal synthetase-tRNA pair, GeneHogs *E. coli* cells Invitrogen) were cotransformed with pKQ-PhE444G, pAC-AK$_{CUA}$, and a lacZ reporter plasmid pLASC-lacZ(TAG) (Anderson and Schultz, (2003) *Biochemistry,* 42(32):9598-608). This plasmid, derived from pSC101, contains an ampicillin resistance selectable marker and the lacZ gene encoding β-galactosidase under the control of the lpp promoter. There is an amber codon at a permissive site, residue 25, of the lacZ gene, which causes premature termination. In the absence of an amber suppressor tRNA, cells harboring pLASC-lacZ (TAG) have only 0.17% of the β-galactosidase activity observed for plasmid pLASC-lacZ(Lys) which contains an AAA (lysine) sense codon at position 25 and only 2-fold higher activity than cells containing no plasmids. If AK$_{CUA}$ is unable to be charged by endogenous *E. coli* synthetases, little amber suppression should be observed when the tRNA is coexpressed with pLASC-lacZ(TAG). Only 1.7% suppression (relative to the expression of lacZ(lys)) is observed for cells harboring pAC-AK$_{CUA}$ and pLASC-lacZ(TAG). If PhKRS is able to charge the orthogonal tRNA, then a higher level of amber suppression should be observed when plasmid pKQ-PhE444G is introduced into the system. Indeed, 32% suppression is observed. In comparison, the orthogonal *M. jannaschii*-derived tyrosine synthetase-tRNA pair described previously for *E. coli* exhibits a suppression efficiency of 18.5% in the presence of the cognate synthetase and 0.2% suppression in the absence of the synthetase. The *M. thermoautotrophicum*-derived leucine amber orthogonal pair gives 33.2% and 1.5% suppression with and without the cognate synthetase, respectively (Anderson and Schultz, (2003) *Biochemistry,* 42(32):9598-608).

In this example, we have identified the type I lysyl-tRNA synthetase and an amber suppressor tRNA derived from the multiple-sequence alignment of archaeal tRNA$^{Lys}$ sequences as an orthogonal synthetase-tRNA pair for the site-specific incorporation of unnatural amino acids in *E. coli*. The high efficiency (32% suppression) observed for the PhKRS/AK$_{CUA}$ pair demonstrates the effectiveness of the consensus sequence strategy for the construction of efficient orthogonal suppressor tRNAs.

Example 2

Frameshift Suppression with an Unnatural Amino Acid Eliminating the Toxicity of PHKRS An orthogonal tRNA-synthetase pair derived from the type I lysyl-tRNA synthetase of *Pyrococcus horikoshii* has been developed for use in *E. coli*. The tRNA portion of the system functioned very well as an orthogonal amber suppressor. The synthetase-expression plasmid pKQ-PhE444G was able to charge this tRNA, but toxicity effects were still observed. When expressed alone, cells harboring pKQ-PhE444G grow to 56% of the density observed for cells with no plasmid. Reporter plasmids PAC-AK$_{CUA}$ and PAC-AK$_{CUA}$ show moderate toxicity as well. When pKQ-PhE444G is cotransformed with plasmid PAC-AK$_{CUA}$, cell density is decreased to 17%. In addition, cells reach a density of only 5% when coexpressed with the β-lactamase reporter plasmid PAC-AK$_{CUA}$ (a derivative of plasmid pACKO-A184TAG). It is therefore clear that there is toxicity with both the tRNA and the synthetase in this system. Furthermore, there appears to be a synergistic effect wherein cells cotransformed with both plasmids are drastically reduced in viability. To address this issue, we sought a less toxic mutant of PhKRS.

It was anticipated that point or other mutations in PhKRS might reduce the toxicity of the synthetase while retaining charging activity. Therefore, pKQ-PhE444G was transformed into chemically competent XL1-red cells (Stratagene) and the cells were plated on LB-agar plates containing 25 ug/mL kanamycin. This strain has several genomic mutations that cause a high rate of mutagenesis in transformed plasmids. Approximately 100 colonies were scraped from this plate and amplified in 25 mL of liquid LB media supplemented with kanamycin. It was anticipated that nontoxic mutants of pKQ-PhE444G would grow faster than the wild-type, and serial culture of the cells would lead to the accumulation of these mutants. After 2 serial cultures with 10000-fold dilution at each step, the cells were miniprepped and introduced into Genehog cells containing plasmid pAC-AK$_{CUA}$ and plated on LB-agar plates containing 25 ug/mL each of kanamycin and chloramphenicol, and various concentrations of ampicillin. Greater than 90% of the transformed cells exhibited no apparent toxicity and were able to survive on LB-agar plates containing 1000 ug/mL ampicillin. Smaller colonies were observed even at 1500 ug/mL ampicillin indicating efficient amber suppression. One mutant synthetase, designated pKQ-PhKep, was isolated and characterized by restriction mapping and sequencing of the PhKRS open reading frame. The mutant gene contains an insertion of 778 bp following residue S357, but is otherwise the same sequence as plasmid pKQ-PhE444G. A BLAST search revealed that this insertion is homologous to a sequence annotated as "insAcp1" from plasmid p1658/97, but no other mention of this sequence has been observed in the literature, and the source of this sequence is unknown. When translated from the start codon of PhKRS, the predicted product of this gene is truncated 6 amino acids downstream of S357. To test whether the truncation of PhKRS was responsible for the elimination of toxicity, primer CA510R with sequence 5'-CAGTGGAATTCAGTAAGTTGGCAGCATCAC-3' (SEQ ID NO:36) was synthesized to explicitly construct the truncation mutant in plasmid pKQ. Plasmid pKQ-PhKep was PCR-amplified with CA279 and CA510R, and the product was subcloned into the NcoI and EcoRI sites of plasmid pKQ. The resulting plasmid, pKQ-PhΔAD (also known as pKQ-Ph510), was cotransformed with plasmid PAC-AK$_{CUA}$ and the resulting transformations were found to have a similar IC$_{50}$ to pKQ-PhKep-transformed cells and no apparent toxicity.

The truncation after residue S357 appears to delete the anticodon binding domain of PhKRS, and we wanted to examine how this deletion affects the tRNA recognition properties of the synthetase. Therefore, we overexpressed the synthetase to perform aminoacylation assays in vitro. The gene was PCR-amplified from pKQ-PhKep with CA279 and CA511 (5'-CATTGGAATTCGAGTAAGTTGGCAGCAT-CAC-3', SEQ ID NO:37) and subcloned into the NcoI and EcoRI sites of pBAD-Myc/HisA in frame with the C-terminal Myc/His tag. Protein wa's purified by Ni-NTA chromatography.

Example 3

Expanding the Genetic Code with Four-Base Codons and Unnatural Amino Acids

Although, with few exceptions, the genetic codes of all known organisms encode the same twenty amino acids, all that is required to add a new building block are a unique tRNA/aminoacyl-tRNA synthetase pair, a source of the amino acid, and a unique codon that specifies the amino acid (Wang et al., (2001) *Expanding the genetic code. Science* 292:498-500). Previously, we have shown that the amber nonsense codon, TAG, together with orthogonal *M. jannaschii* and *E. coli* tRNA/synthetase pairs can be used to genetically encode a variety a variety of amino acids with novel properties in *E. coli* (Wang et al., (2003) *Addition of the keto functional group to the genetic code of Escherichia coli. Proc. Natl. Acad. Sci. U.S.A.* 100:56-61; Santoro et al., (2002) *An efficient system for the evolution of aminoacyl-tRNA synthetase specificity. Nat. Biotechnol.* 20:1044-8; Chin et al., (2002) *Addition of a photocrosslinking amino acid to the genetic code of Escherichia coli. Proc. Natl. Acad. Sci. U.S.A.* 99:11020-11024; Mehl et al. (2003) *Generation of a bacterium with a 21 amino acid genetic code. J. Am. Chem. Soc.* 125:935-9), and yeast (Chin et al. (2003) *An expanded eukaryotic genetic code. Science* 301:964-7), respectively. The limited number of noncoding triplet codons, however, severely restricts the ultimate number of amino acids encoded by any organism. Here we report the generation of a new orthogonal synthetase/tRNA pair derived from archaeal tRNA$^{Lys}$ sequences that efficiently and selectively incorporates the amino acid homoglutamine (hGln) into myoglobin in response to the four-base codon AGGA. Frameshift suppression with hGln does not significantly affect protein yields or cell growth rates, and was shown to be mutually orthogonal with suppression of TAG. This work suggests that neither the number of available triplet codons nor the translational machinery itself represents a significant barrier to further expansion of the code.

There are many examples of naturally occurring +1 frameshift suppressors including UAGN (N=A, G, C or T) suppressors derived from Su7 encoding glutamine (Curran and Yarus (1987) *Reading frame selection and transfer RNA anticodon loop stacking. Science* 238:1545-50), sufJ-derived suppressors of ACCN codons encoding threonine (Bossi and Roth (1981) *Four-base codons ACCA, ACCU and ACCC are recognized by frameshift suppressor sufJ. Cell* 25:489-96), and CAAA suppressors derived from tRNA$^{Lys}$ and tRNA$^{Gln}$ (O'Connor (2002) *Insertions in the anticodon loop of tRNA (1)(Gln)(sufG) and tRNA(Lys) promote quadruplet decoding of CAAA. Nucleic Acids Res.* 30:1985-1990). Moreover, genetic selections have been used to identify efficient four- and five-base codon suppressor tRNAs from large libraries of mutant tRNAs, including an *E. coli* tRNA$_{UCCU}^{Ser}$ suppressor (Magliery et al., (2001) *Expanding the genetic code: selection of efficient suppressors of four-base codons and identification of "shifty" four-base codons with a library approach in Escherichia coli. J. Mol. Biol.* 307:755-769; Anderson et al., (2002) *Exploring the limits of codon and anticodon size. Chem. Biol.* 9:237-244; Hohsaka et al., (1999) *Incorporation of two nonnatural amino acids into proteins through extension of the genetic code. Nucleic Acids Symp. Ser.* 42:79-80; Hohsaka et al., (2001) *Five-base codons for incorporation of* nonnatural amino acids into proteins. *Nucleic Acids Res.* 29:3646-51; Hohsaka and Sisido (2002) *Incorporation of non-natural amino acids into proteins. Curr. Opin. Chem. Biol.* 6:809-15).

In order to encode unnatural amino acids with quadruplet codons in vivo, one has to generate a tRNA that uniquely recognizes this codon and a corresponding synthetase that uniquely aminoacylates only this tRNA with the unnatural amino acid of interest. Because the anticodon loop of the previously generated orthogonal *M. jannaschii* amber suppressor tRNA is a key recognition element for the cognate synthetase, JYRS, it was difficult to engineer this tRNA to decode a four-base codon. Although it may be possible to relax the anticodon binding specificity of JYRS, it would likely be difficult to construct mutually orthogonal pairs that distinguish amber and four-base suppressors using exclusively the anticodon sequence. Therefore, a system that permitted the simultaneous incorporation of two unnatural amino acids into a polypeptide would most likely be achieved using two orthogonal pairs of distinct origin, necessitating, the development a new orthogonal tRNA-synthetase pair.

We initially focused on the lysyl synthetase/tRNA pair of the archaean *Pyrococcus horikoshii* (PhKRS) as a candidate orthogonal pair since 1) this pair is likely to be orthogonal due to the conservation of A73 in prokaryotes and G73 in archaea (Ibba et al. (1999) *Substrate recognition by class I lysyl-tRNA synthetases: a molecular basis for gene displacement. Proc. Natl. Acad. Sci. U.S.A.* 96:418-423), 2) PhKRS is tolerant of substitutions to the tRNA anticodon loop permitting the charging of suppressor tRNAs (Terada et al. (2002) *Functional convergence of two lysyl-tRNA synthetases with unrelated topologies. Nat. Struct. Biol.* 9:257-262), and 3) the crystal structure of PhKRS is available (Terada et al. (2002) *Functional convergence of two lysyl-tRNA synthetases with unrelated topologies. Nat. Struct. Biol.* 9:257-262) to facilitate changes in amino acid specificity. Unfortunately, we found that PhKRS is toxic to *E. coli* cells when expressed constitutively. However, serial culture in the mutator strain XL1-red led to the isolation of a non-toxic variant, PhΔAD, which is truncated 6 amino acids downstream of residue S357 because of a 778 bp insertion element annotated as insAcp1. As such, the anticodon loop-binding domain has been deleted, further minimizing any loss in activity that might result from anticodon loop replacement.

As noted in more detail in Example 1, to determine whether this truncation mutant is functional and orthogonal in *E. coli*, it was useful to demonstrate that the synthetase cannot charge *E. coli* tRNA to any significant extent but retains activity towards cognate archaeal tRNA. Genes for PhΔAD and EcKRS were cloned and overexpressed and protein was purified to homogeneity. Aminoacylation of whole tRNA from an archaebacterium, *Halobacterium* sp. NRC-1, or *E. coli* was assayed. PhΔAD charges a greater amount of whole halobacterial tRNA than whole *E. coli* tRNA in 20 minutes (FIG. 2; 10 µM [tRNA]). Although PhΔAD is able to weakly charge *E. coli* tRNA, the rate is 28-fold lower than the activity of the *E. coli* synthetase towards the same concentration of whole *E. coli* tRNA and only 7-fold over background charging. Furthermore, PhΔAD was unable to complement growth at 43° C. of strain PALΔSΔUTR(pMAKlysU) (Chen et al., (1994) *Properties of the lysyl-tRNA synthetase gene and product from the extreme thermophile Thermus thermophilus. J. Bacteriol.* 176:2699-705), a lysS/lysU double mutant deficient in *E. coli* lysyl-tRNA synthetase. However, EcKRS (cloned from the lysU locus of *E. coli* strain HB101) afforded normal growth. Therefore, PhΔAD is unable to substitute for EcKRS and would likely compete poorly with endogenous *E. coli* synthetases for charging of *E. coli* tRNAs in vivo.

To demonstrate that PhΔAD was functional in *E. coli*, we used a β-lactamase suppression assay with an orthogonal amber suppressor tRNA for PhΔAD. This approach also allowed us to use the selection schemes previously developed for the *M. jannaschii* orthogonal pair. A suppressor tRNA$_{CUA}$ (AK$_{CUA}$) was designed using a recently-described consensus-suppressor strategy (Anderson and Schultz, P. G. (2003) *Adaptation of an Orthogonal Archaeal Leucyl-tRNA and Synthetase Pair for Four-base, Amber, and Opal Suppression. Biochemistry* 42:9598-608). A multiple sequence alignment of all archaeal tRNA$^{Lys}$ sequences from available genomic sequences was performed and a consensus sequence was determined. The anticodon loop sequence was changed to CUCUAAA to afford an amber suppressor tRNA (FIG. 1). The gene for AK$_{CUA}$ was synthesized and inserted into plasmid pACKO-A184TAG (Anderson and Schultz, P. G. (2003) *Adaptation of an Orthogonal Archaeal Leucyl-tRNA and Synthetase Pair for Four-base, Amber, and Opal Suppression. Biochemistry* 42:9598-608) to examine amber suppression efficiency. This plasmid contains a gene for β-lactamase (bla) with a TAG codon at the permissive site A184. With no tRNA, translation affords no observable full-length β-lactamase, and sensitivity to 5 µg/mL ampicillin. When expressed with AK$_{CUA}$, no increase in ampicillin resistance was observed indicating that the tRNA is uncharged by *E. coli* synthetases. When coexpressed with PhΔAD, the orthogonal tRNA was charged leading to efficient amber suppression and resistance to 1000 µg/mL ampicillin. The PhΔAD/AK$_{CUA}$ orthogonal pair is therefore an efficient and orthogonal amber suppression system.

Previously, it was shown that the four-base codon AGGA can be efficiently suppressed by an *E. coli* tRNA$_{UCCU}^{Ser}$. In this case suppression of the four-base codon is competing with the rare codon AGG which may contribute to the efficiency and lack of toxicity of the suppressor tRNA. An AGGA suppressor tRNA was designed from AK$_{CUA}$ by changing the anticodon loop to CUUCCUAA and inserted into plasmid pACKO-A184AGGA. Similar to pACKO-A184TAG, this plasmid contains an AGGA codon at position A184 resulting in abortive translation and resistance to only 5 µg/mL ampicillin. Unfortunately, this tRNA is no longer orthogonal to *E. coli* synthetases. Cells containing the designed tRNA survive to 200 µg/mL ampicillin both in the absence and presence of PhΔAD.

Figure 5:
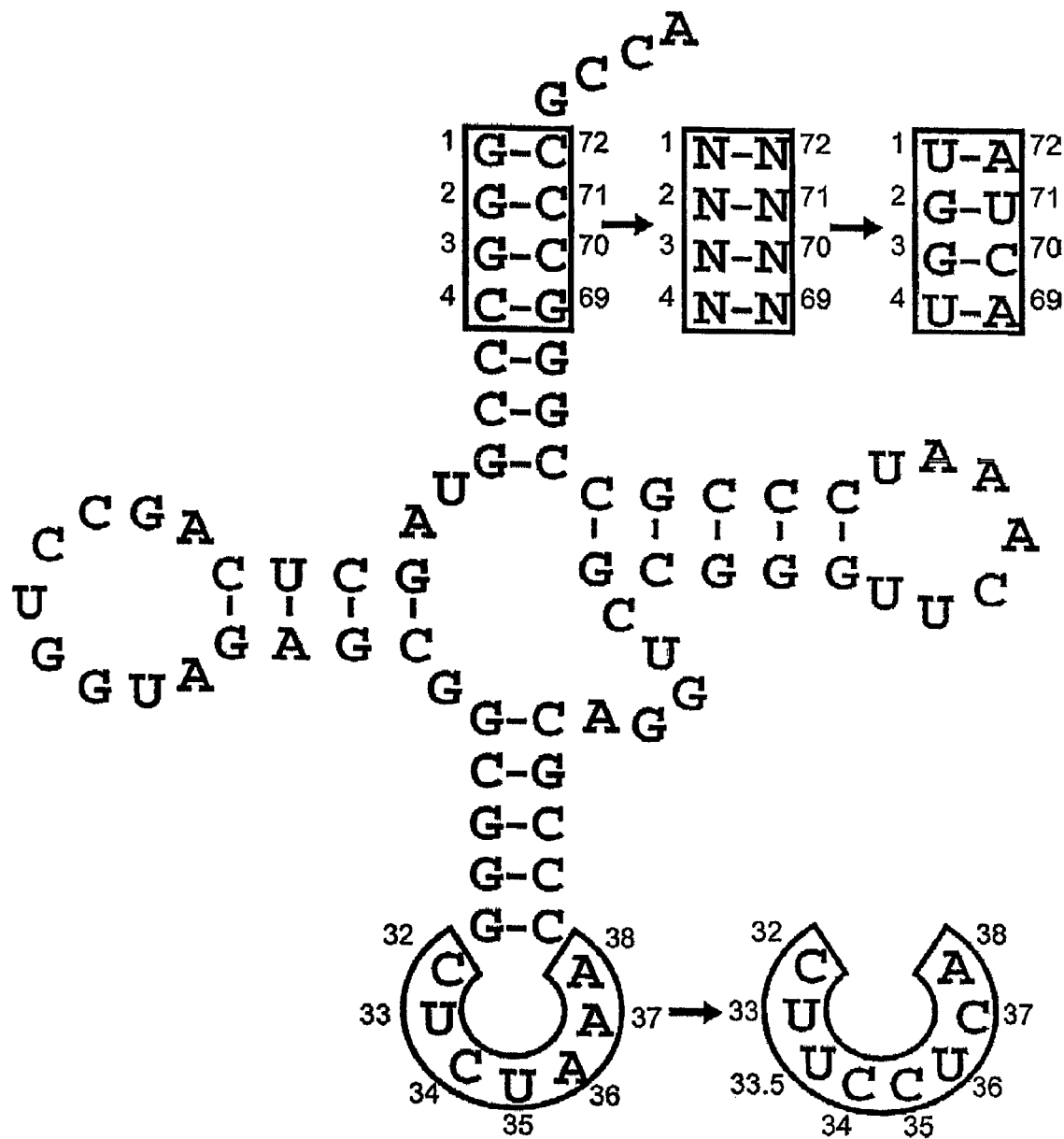
FIG. 5. Construction of amber and four-base suppressor tRNAs. An amber suppressor tRNA (SEQ ID NO:24) was constructed from the multiple sequence alignments of many tRNA$^{lys}$ sequences. An Orthogonal AGGA suppressor tRNA was identified by selection from an acceptor stem library.
Figure 6B:
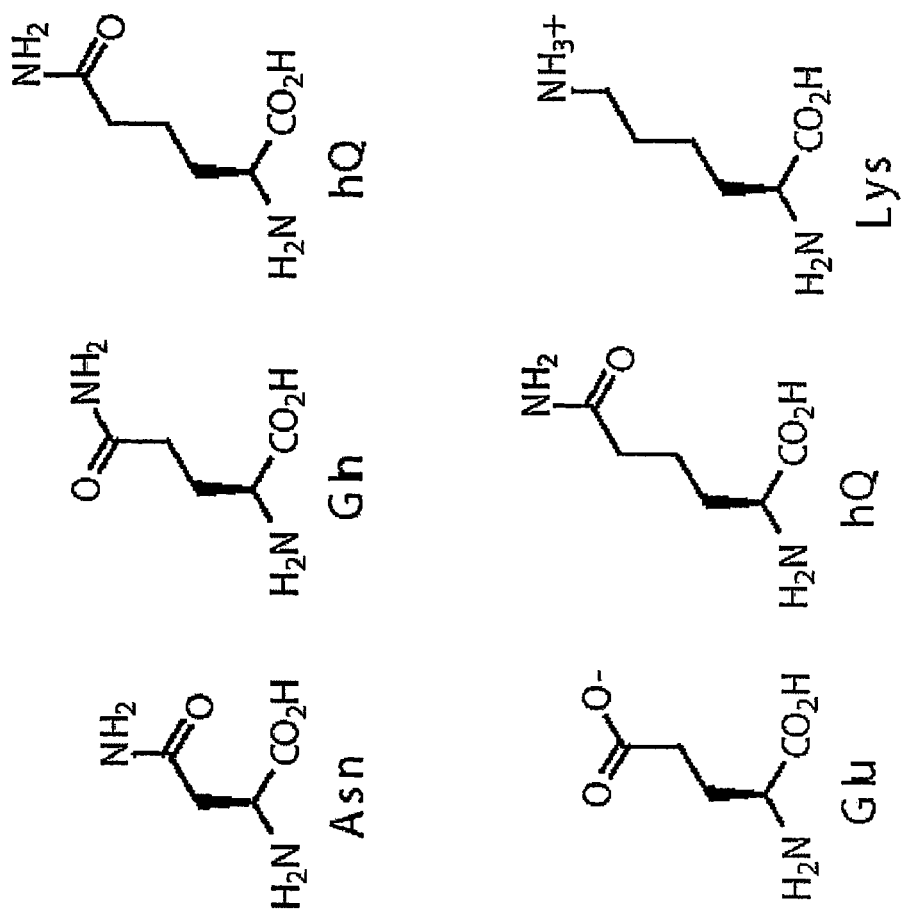
FIGS. 6A and 6B.
Figure 6A:
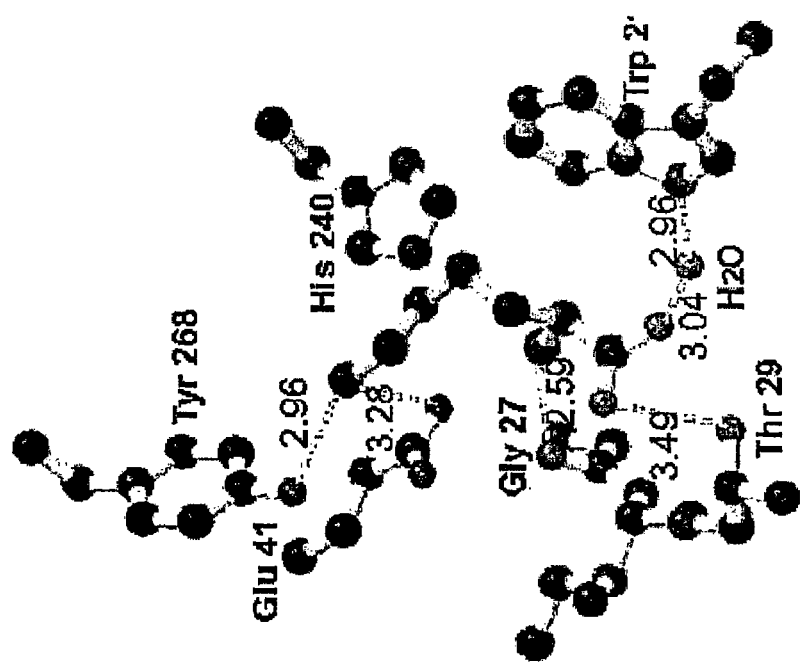

To identify orthogonal variants, we constructed a library in which the last four base pairs of the acceptor stem, positions 1-4 and 69-72, were simultaneously randomized (Anderson and Schultz, P. G. (2003) *Adaptation of an Orthogonal Archaeal Leucyl-tRNA and Synthetase Pair for Four-base, Amber, and Opal Suppression. Biochemistry* 42:9598-608). These tRNAs were coexpressed with PhΔAD and cells were subjected to two rounds of ampicillin selection at 200 µg/mL resulting in a pool of active AGGA suppressor tRNAs. To identify orthogonal variants, tRNA plasmids were isolated and 384 individual clones were screened for sensitivity to ampicillin in the absence of PhΔAD. Of these, the most efficient and orthogonal clone is resistant to 700 µg/mL ampicillin in the presence of PhΔAD but survives to only 5 µg/mL in its absence. This tRNA, AK$_{UCCU}$, contains multiple acceptor stem substitutions and a serendipitous A37C mutation of unknown importance (FIG. 5).

To incorporate homoglutamine in response to AGGA, it was next useful to alter the specificity of PhΔAD. Homoglutamine was chosen as an initial target to test the fidelity of a modified synthetase because it is similar in size to lysine and has both hydrogen bond donating and accepting properties. Examination of the PhKRS crystal structure, only two residues specifically recognize the ε-amino group of lysine, E41 and Y268. They were simultaneously randomized by saturation mutagenesis in the construction of a small active site library derived from PhΔAD. To screen for hGln-specific synthetases, we used a GFP reporter plasmid, pREP2-AK$_{CUA}$ (Santoro et al., (2002) *An efficient system for the evolution of aminoacyl-tRNA synthetase specificity. Nat. Biotechnol.* 20:1044-8) which encodes the gene for AK$_{CUA}$, a T7 RNA polymerase gene with two TAG codons at positions M1 and Q107, and GFPuv under the control of a T7 promoter. When cotransformed with pREP2-AK$_{CUA}$ and PhΔAD, the amber codons in T7RNAP are suppressed resulting in GFPuv expression and green fluorescence. In the absence of the synthetase, cells are white. As such, cells harboring active synthetases can be identified by observing fluorescence. Cells were cotransformed with pREP²-AK$_{CUA}$ and the library was then spread on plates containing hGln. Individual green colonies were isolated and grown with and without the unnatural amino acid to identify clones whose fluorescence required hGln. Of 15 colonies screened, 5 showed a higher fluorescence on plates containing hGln. Of these, all but one conserved a Y268S substitution; the most selective of these synthetases, hGlnRS, has I41 and S268 and was characterized further. The 5 mutants corresponding to the 5 colonies had the following sequence changes, as compared to PhΔAD:

| Clone | Y268(codon) | E41(codon) |
|---|---|---|
| Clone 2 | Ser(TCT) | Val(GTT) |
| Clone 3 | Ser(TCG) | Thr(ACG) |
| Clone 4 | Ser(AGT) | Ser(AGT) |
| Clone 5 | Ser(TCG) | Ile(ATT) |
| Clone 6 | Gly(GGT) | Pro(CCG). |

Myoglobin protein with a Gly24→AGGA mutation was then expressed using the orthogonal hGlnRS/AK$_{TCCT}$ pair to determine whether the observed hGln-dependent phenotype resulted from the specific incorporation of the unnatural amino acid. Upon expression of the mutant myoglobin gene in the absence hGlnRS, no detectable protein was produced. When coexpressed with hGlnRS, 1.8 mg/mL myoglobin was isolated. In comparison, 3.8 mg/mL of myoglobin was produced upon expression of plasmid pBAD-JYAMB which contains the wild-type myoglobin gene. MALDI-TOF analysis of tryptic fragments of the purified protein revealed a peptide of mass 1676.85 Da, consistent with the predicted mass of 1676.88 Da. No evidence of peptides containing lysine or glutamine at position 24 were observed. Furthermore, we observed little toxicity during hGln incorporation in response to AGGA. During midlog growth under the conditions used for myoglobin expression without arabinose induction, doubling time for GeneHogs cells is twice that of cells incorporating hGln. This reduction in growth rate was observed both in the presence and absence of hGln indicating that the slight toxicity is the result of synthetase and tRNA expression rather than AGGA suppression. Therefore, cross-reactivity of the AGGA suppressor with rare AGG codons does not limit the practical application of frameshift suppression.

Figure 7A:
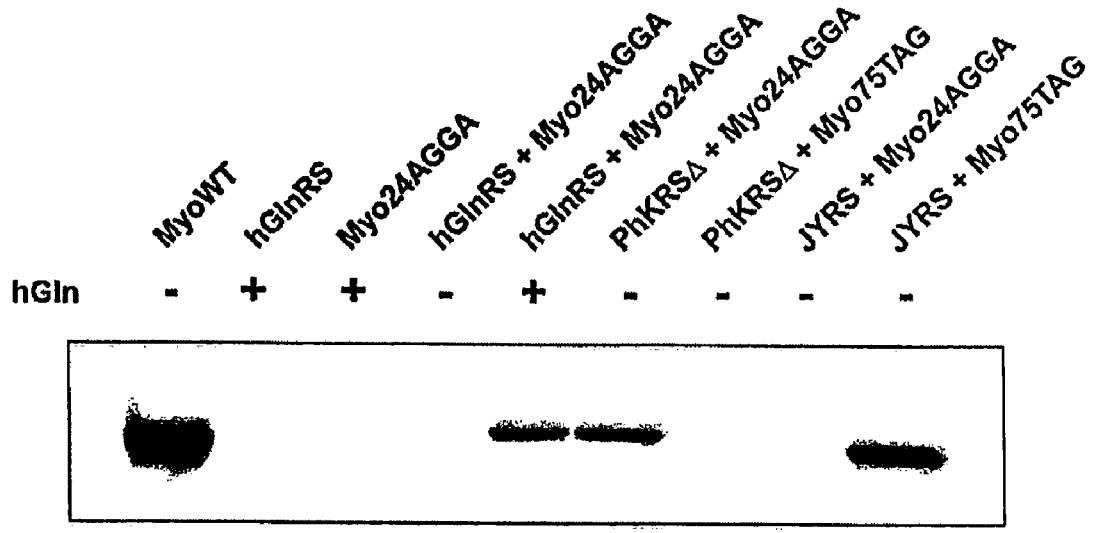
FIGS. 7A and 7B provide chemifluorescence phosphoimages illustrating expression of myoglobin by AGGA suppression.

The expression of myoglobin by AGGA suppression to incorporate a hGln residue is demonstrated in FIG. 7A. This figure provides a western blot probed with an anti-His C-terminal antibody. Protein was produced from the myoglobin gene with an AGGA codon at position G24 (Myo24AGGA) only in the presence of all three components, AK514 tRNA, hGlnRS (an hGln-specific variant of PhKRSΔ) and hGln (lanes 2-5). Expression of myoglobin by amber suppression at position 75 (Myo75TAG) was only possible with JYRS and its cognate amber tRNA, demonstrating the mutual orthogonality of the lysyl and tyrosyl pairs (lanes 6-9).

We also investigated the possibility of using the PhΔAD/AK$_{UCCU}$ pair in combination with the *M. jannaschii* tyrosine synthetase (JYRS) for the simultaneous suppression of TAG and AGGA in a single polypeptide. When coexpressed with JYRS in plasmid pBK-JYRS, pMyo-AK$_{UCCU}$ affords no detectable myoglobin. Therefore, JYRS is unable to charge AK$_{UCCU}$. Conversely, we attempted to express myoglobin from plasmid pBAD/JYAMB-4TAG by charging with PhΔAD. This expression plasmid contains the myoglobin gene with a TAG codon at position 4 and an orthogonal tRNA$^{Tyr}$, J17 (Mehl et al. (2003) *Generation of a bacterium with a 21 amino acid genetic code. J. Am. Chem. Soc.* 125: 935-9). Coexpression with JYRS affords 3.8 mg/mL of myoglobin, but no protein is observed with PhΔAD. Therefore, PhΔAD is unable to charge J17. As such, these synthetase/tRNA pairs are mutually orthogonal and could be used in combination without cross-reacting.

For the incorporation of two unnatural amino acids into myoglobin, AK$_{UCCU}$ and J17 were combined into a single plasmid expressing a mutant myoglobin with Gly24→AGGA and Ala75→TAG. An O-Methyl-L-tyrosine-specific synthetase (OMeYRS) (Chin et al., (2002) *Addition of a photocrosslinking amino acid to the genetic code of Escherichia coli. Proc. Natl. Acad. Sci. U.S.A.* 99:11020-11024) derived from JYRS and hGlnRS were combined in a second plasmid. When cells cotransformed with both plasmids were grown in the presence of both amino acids, 1.7 mg/L of myoglobin was produced. No protein was produced when either of the two unnatural amino acids or synthetases was excluded.

Figure 7B:
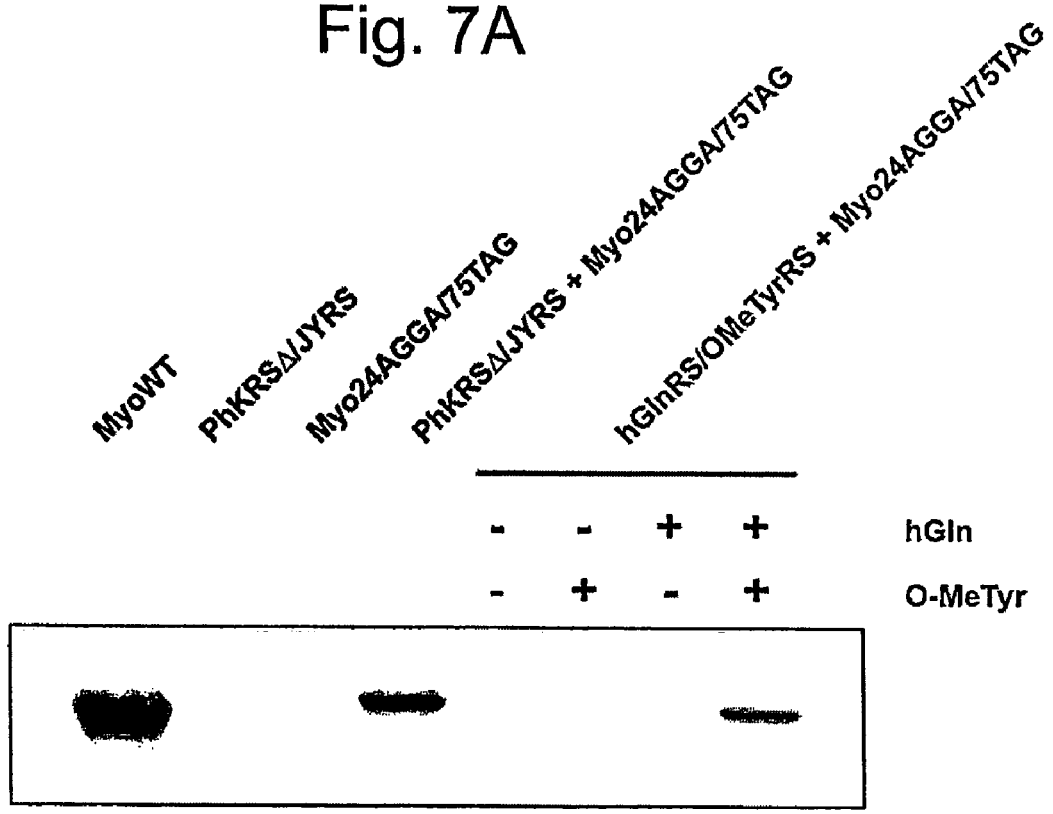

The simultaneous use of two orthogonal tRNA systems to incorporate two different unnatural amino acids using the myoglobin model system is demonstrated in FIG. 7B. This figure provides a western blot probed with an anti-His C-terminal antibody. Protein was expressed from a myoglobin gene containing an AGGA codon at position 24 and a TAG codon at position 75 (Myo24AGGA/75TAG) in the presence of both lysyl and tyrosyl orthogonal pairs. hGln was incorporated by AGGA suppression at position 24, and O-methyl-tyrosine (OMeTyr) was incorporated by amber suppression at position 75 in a single polypeptide by using hGlnRS and OMeTyrRS. As shown in the figure, a polypeptide is produced only when both unnatural amino acids are present, and furthermore, only when both the lysyl and tyrosyl orthogonal systems are present.

Figure 8:
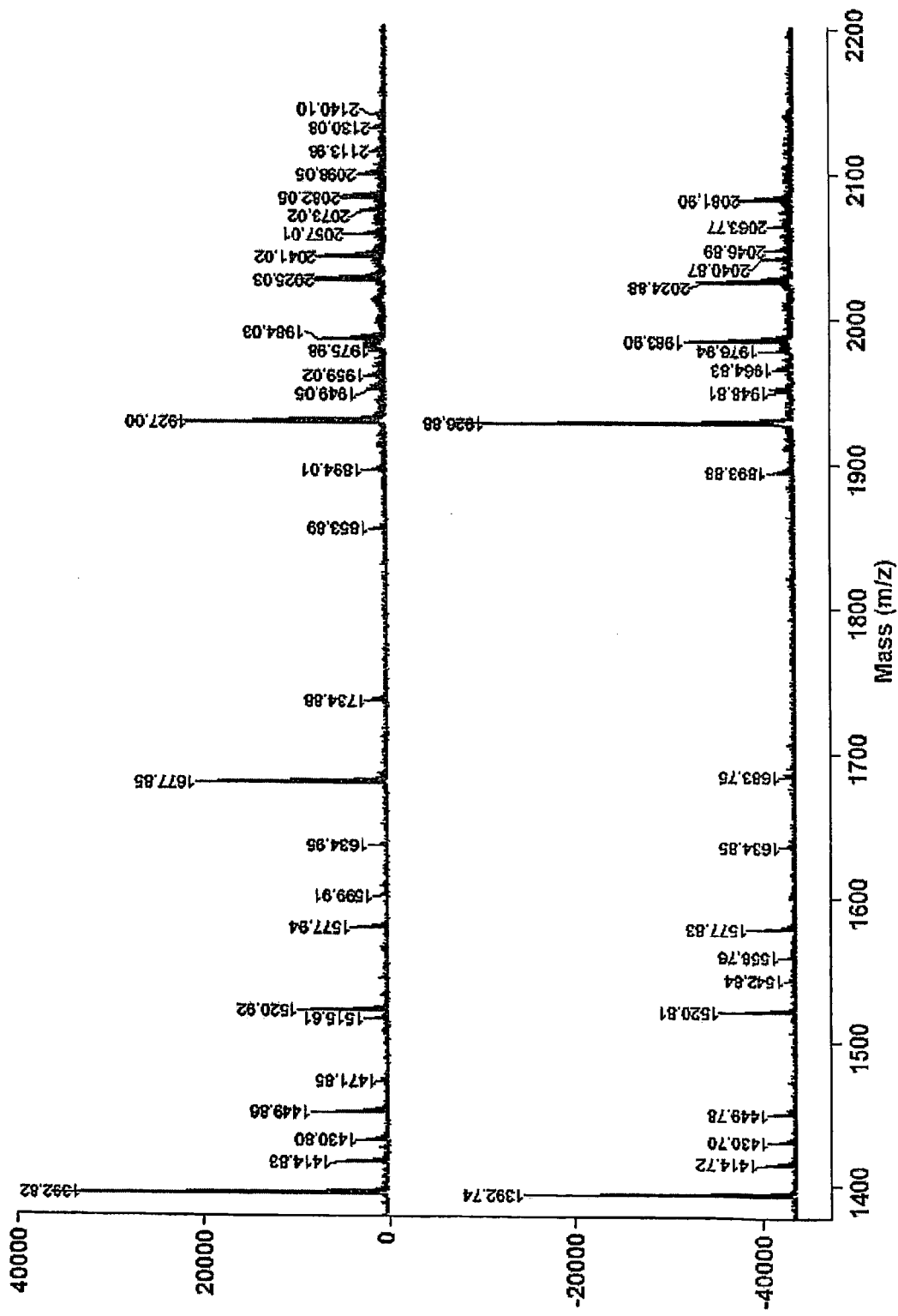
FIG. 8. MALDI-TOF analysis of tryptic fragments containing homoglutamine or lysine.
Figure 9:
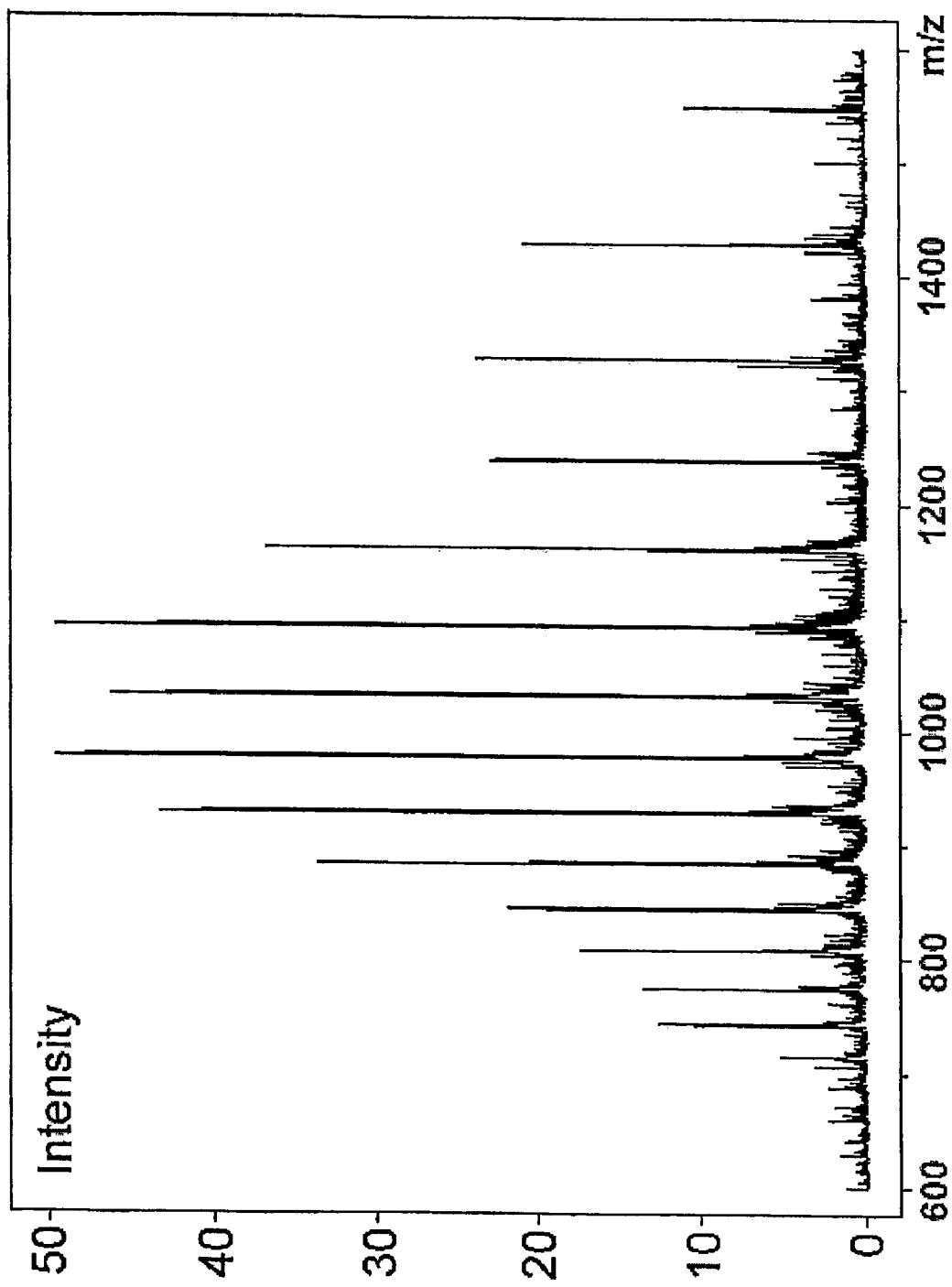
FIG. 9. Electrospray MS analysis of full-length myglobin containing homoglutamine at position 24 and O-methyl-tyrosine at position 75.

The results observed in the western blots of FIGS. 7A and 7B are further confirmed in analyses provided in FIGS. 8 and 9. FIG. 8 provides a matrix-assisted laser desorption ionization-time-of-flight analysis of tryptic fragments of the wild-type myoglobin (MyoWT; presumably containing lysine at position 24) and mutant myoglobin (24AGGA; presumably containing hGln) as produced in FIG. 7A. The analyses of these myoglobin species are shown in the upper and lower panels, respectively. The analysis revealed tryptic peptide fragments of the purified protein revealed a peptide of mass 1,676.85 Da, consistent with the predicted mass of 1676.88 Da. No evidence of peptides containing lysine (observed mass of 950.46 Da from the protein expressed with PhKRSΔ for the trypsin-cleaved peptide and calculated mass of 950.53 or 1,661.91 Da for the full-length peptide) or glutamine at position 24 (calculated mass, 1661.87 Da) was observed.

FIG. 9 provides an electrospray MS analysis of the full-length double mutant protein (produced in FIG. 7B). The MS analysis revealed a mass of 18,546.40 Ds (SD 0.11), consistent with the predicted mass of 18,546.60 (SD 0.81) for myoglobin containing both unnatural amino acid, compared with the calculated mass of 18,518.3 Da for myoglobin with the G24K and A75Y substitutions.

In summary, we have demonstrated the use of frameshift suppression for the site-specific incorporation of an unnatural amino acid in vivo. Furthermore, we have demonstrated the mutual orthogonality of this *P. horikoshii*-derived lysyl-tRNA synthetase and an orthogonal pair derived from the *M. jannaschii* tyrosyl-tRNA synthetase and shown that we can the simultaneously incorporate two unnatural amino acids into a single polypeptide. It should be possible to identify synthetase variants that permit the incorporation of mutually-orthogonal reactive handles or even fluorophore amino acids. With such materials, it is possible to incorporate a fluorophore pair into a polypeptide for FRET studies in vivo. Similarly, it is possible to incorporate moieties other than amino acids such as α-hydroxy acids for the ribosomal production of unnatural polymers. Additional codons such as CCCU or CUAG can be used, which are efficiently suppressed in *E. coli*. Alternatively, the genome of *E. coli* could be resynthesized with limited codon degeneracy thereby making up to 43 codons available for recoding.

Materials and Methods

Cloning and expression of synthetase genes: Genomic DNA was prepared from *P. horikoshii* obtained from the American Type Culture Collection (ATCC; #700860). PhKRS was amplified by PCR and cloned into the NcoI and EcoRI sites of plasmid pBAD/Myc-HisA (Invitrogen) for overexpression. For constitutive expression, the synthetase genes were cloned into pGLN and pKQ (Anderson and Schultz (2003) *Adaptation of an Orthogonal Archaeal Leucyl-tRNA and Synthetase Pair for Four-base, Amber, and Opal Suppression. Biochemistry* 42:9598-608) under the control of the glutamine promoter. These plasmids derived from pBAD/Myc-HisA confer resistance to ampicillin and kanamycin, respectively. Similarly, EcKRS was cloned from the lysU locus of *E. coli* strain HB101. Protein was overexpressed in 2YT media by the protocol described for the Qiagen QIAexpressionist kit and then dialyzed against 100 mM Tris-HCl, pH 7.5; 100 mM NaCl; and 10% glycerol.

In vitro aminoacylation assays: Whole *E. coli* tRNA was purchased from Roche and halobacterial tRNA was extracted from cultures of *Halobacterium* sp. NRC-1 (ATCC; #700922) with the RNA/DNA Extraction Kit (Qiagen). Assays were performed in 20 μL reactions containing 50 mM Tris-HCl, pH 7.5, 30 mM KCl, 20 mM $MgCl_2$, 3 mM glutathione, 0.1 mg/mL BSA, 10 mM ATP, 1 μM [3w] lysine (Amersham), 750 nM synthetase, and 0, 2, 10, or 40 μM whole tRNA at 37° C. for 20 minutes.

Complementation analysis: PALΔSΔUTR(pMAKlysU) cells were transformed with pGLN derivatives for expression of PhΔAD, EcKRS, or no synthetase and rescued on LB-agar plates containing 50 μg/mL ampicillin at 30° C. Complementation at 43° C. of the synthetase-deficient growth defect of strain PALΔSΔUTR was done on LB agar plates or liquid media with no antibiotics. Growth in GeneHogs was used as a positive control to eliminate the possibility of toxic effects from synthetase expression. For liquid media, saturated cultures were diluted 10000-fold into fresh media and growth was monitored at 600 nm for 8 hours.

Library construction: Genes for tRNAs were constructed by the overlap extension of synthetic oligonucleotides (Genosys) and subcloned into the EcoRI and PstI sites of pACKO-A184TAG or pACKO-A184AGGA. These reporter plasmids derived from pACYC184 contain the p15A origin of replication, a chloramphenicol resistance gene, and a strong constitutive promoter controlling expression of the tRNA genes. The PhΔAD-derived library was constructed in plasmid pKQ by EIPCR (Stemmer and Morris, S. K. (1992) *Enzymatic inverse PCR: a restriction site independent, single-fragment method for high-efficiency, site-directed mutagenesis. Biotechniques* 13:214-20). Premixed phosphoramidites were used during oligonucleotide synthesis for library construction. Library diversity was 900-fold higher than the theoretical diversity and shown to be free of sequence bias by sequencing.

Determination of suppression efficiency: Suppression efficiency was determined by plating on LB-agar media supplemented with 25 μg/mL kanamycin and chloramphenicol and various concentrations of ampicillin between 5 and 1000 μg/mL. Cells were plated at densities below 100 cells per plate. Efficiency was reported as the highest concentration at which cells survived to form colonies among a series of plates for which the next highest and lowest concentrations would be within 20% of the reported value.

Expression and characterization of myoglobin containing hGln: For single-site incorporation experiments, pMyo-$AK_{UCCU}$ was constructed with a p15A origin of replication and genes for chloramphenicol acetyltransferase, $AK_{UCCU}$, and sperm whale myoglobin. The myoglobin gene was placed under the control the arabinose promoter and contains an AGGA codon at position G24. For two-site incorporation another plasmid was constructed by introducing a TAG codon at position A74 of the myoglobin gene in pMyo-$AK_{UCCU}$. The orthogonal $tRNA^{Tyr}$, J17, was added under the control of a second lpp promoter. Synthetases hGlnRS and AzPheRS were expressed from plasmid pKQ under independent glutamine promoters. GeneHogs cells harboring appropriate synthetase and myoglobin expression plasmids were grown at 37° C. to $OD_{600}$=0.7 in GMML media supplemented with the 19 amino acids except lysine at 0.4 mg/ml each, vitamins and 1 mg/ml hGln (Sigma), induced with 0.02% arabinose, and then grown to saturation. Cells were lysed by sonication, and myoglobin was purified with the Qiagen QIAexpressionist kit. MALDI-MS analysis of tryptic fragments was performed at the TSRI Proteomics Facility.

Example 4

Exemplary Lysyl O-RSs and Lysyl O-tRNAs

Exemplary O-tRNAs are found in the examples and/or Table 1. Exemplary O-RSs are also found in the examples and/or Table 1. Exemplary polynucleotides that encode O-RSs or portions thereof include those found in the examples and/or Table 1.

Further details of the invention, and in particular experimental details, can be found in Anderson, John Christopher, "Pathway Engineering of the Expanding Genetic Code," Ph.D. Dissertation, The Scripps Research Institute [2003].

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 1

| SEQ ID: | Label | SEQUENCE |
|---|---|---|
| SEQ ID:1 | Pa15 | GGGCCGGUAGCUUAGCCUGGUUAGAGCGGCGGACUCUUAAUC CGCAGGUCGGGGGUUCAAAUCCCCCCCGGCCCGCCA |
| SEQ ID:2 | Pf32 | GGGCCGGUAGCUUAGCCUGGUUAGAGCGGCGGACUCUUAAUC CGCAGGUCGGGGGUUCAAAUCCCCCCCGGCCCGCCA |
| SEQ ID:3 | Ph36 | GGGCCGGUAGCUUAGCCUGGUUAGAGCGGCGGACUCUUAAUC CGCAGGUCGGGGGUUCAAAUCCCCCCCGGCCCGCCA |
| SEQ ID:4 | Pa34 | GGGCCGGUAGCUCAGCCUGGUCAGAGCACCGGGCUUUUAACC CGGUGGUCGCGGGUUCAAAUCCCGCCCGGCCCGCCA |
| SEQ ID:5 | Ph9 | GGGCCGGUAGCUCAGCCUGGUCAGAGCACCGGGCUUUUAACC CGGUGGUCGCGGGUUCAAAUCCCGCCCGGCCCGCCA |
| SEQ ID:6 | Pf4 | GGGCCGGUAGCUCAGCCUGGUUAGAGCACCGGGCUUUUAACC CGGUGGUCGCGGGUUCAAAUCCCGCCCGGCCCGCCA |
| SEQ ID:7 | Pya26 | GGGCCCGUAGCUCAGCCCGGUUAGAGCGGCGGGCUUUUAACC CGUAGGUGGUGGGUUCGAAUCCCACCGGGCCCGCCA |
| SEQ ID:8 | Ta1 | GGUCCGUAGCUUAGCUAGGUAGAGCGAUGGACUCUUAAUCC AUAGGUCAGGGGUCCAAAUCCCCUCGGACCCGCCA |
| SEQ ID:9 | Tv40 | GGGUCCGUAGCUUAGCUAGGUAGAGCGAUGGACUCUUAAUCC AUAGGUCAGGGGUCCAAAUCCCCUCGGACCCGCCA |
| SEQ ID:10 | Af18 | GGGCCGGUAGCUUAGCCAGGCAGAGCGCGGGACUCUUAAUCC CGCAGUCGGGGGUUCAAAUCCCUCCCGGCCCGCCA |
| SEQ ID:11 | Hh1 | GGGCCGGUAGCUCAGUCUGGCAGAGCGACGGACUCUUAAUCC GUCGGUCGCGUGUUCAAAUCGCGCCCGGCCCGCCA |
| SEQ ID:12 | Ta5 | GGGCCCGUAGCUCAGCCAGGUAGAGCAUCUGGCUUUUAACCA GGUGGUCAGGGGUUCGAACCCCCUCGGGCCCGCCA |
| SEQ ID:13 | Tv24 | GGGCCCGUAGCUCAGCCAGGUAGAGCAUCUGGCUUUUAACCA GGUGGUCAGGGGUUCGAACCCCCUCGGGCCCGCCA |
| SEQ ID:14 | Mj21 | GGGCCCGUAGCUCAGUCUGGCAGAGCGCCUGGCUUUUAACCA GGUGGUCGAGGGUUCAAAUCCCUUCGGGCCCGCCA |
| SEQ ID:15 | Mt15 | GGGCCCGUAGCUCAGUCUGGCAGAGCGCUUGGCUUUUAACCA AGUGGUCGCGGGUUCAAUUCCCGUCGGGCCCGCCA |
| SEQ ID:16 | Mm4 | GGGCCCGUAGCUUAGUCUGGUAGAGCGCCUGACUUUUAAUCA GGCGGUCGAGGGUUCGAAUCCCUUCGGGCCCGCCA |
| SEQ ID:17 | St1 | GGGCCCGUAGCUCAGCCAGGUAGAGCGGCGGGCUCUUAACCC GUAGGUCCCGGGUUCAAAUCCCGGCGGGCCCGCCA |
| SEQ ID:18 | St43 | GGGCCCGUAGCUCAGCCAGGUAGAGCGGCGGGCUUUUAACCC GUAGGUCCCGGGUUCAAAUCCCGGCGGGCCCGCCA |
| SEQ ID:19 | Pya13 | GGGCCCGUAGCUCAGCCUGGUAGAGCGGCGGGCUCUUAACCC GUAGGUCGUGGGUUCGAAUCCCACCGGGCCCGCCA |
| SEQ ID:20 | Af15 | GGGCUCGUAGCUCAGCCAGGCAGAGCGACGGGCUUUUAACCC GUCGGUCGCGGGUUCAAAUCCCGUCGAGCCCGCCA |
| SEQ ID:21 | Ss43 | GGGCCCGUAGCUUAGCCAGGUAGAGCGACGGGCUCUUAACCC GUAGUCCCGGGUUCGAAUCCCGGCGGGCCCGCCA |
| SEQ ID:22 | Ap47 | GGGCCCGUAGCUCAGCCUGGUAGAGCGGCGGGCUCUUACCCC GCGGAAGUCCCGGGUUCAAAUCCCGGCGGGCCCGCCA |
| SEQ ID:23 | Consensus | GGGCCCGUAGCUCAGCCUGGUUAGAGCGGCGGGCU-UUAACC- CGGAGGUCGCGGGUUCAAAUCCCGCCGGGCCCGCCA |
| SEQ ID:24 | AK$_{CUA}$ | GGGCCCGUAGCUCAGCCUGGUAGAGCGGCGGGCUCUAAACCCGCA GGUCGCGGGUUCAAAUCCCGCCGGGCCCGCCA |

TABLE 1-continued

| SEQ ID: | Label | SEQUENCE |
|---|---|---|
| SEQ ID:25 | AK$_{stemlibrary}$ | NNNNCCGUAGCUCAGCCUGGUAGAGCGGCGGGCUUCCUAACCCGC<br>AGGUCGCGGGUUCAAAUCCCGCCGGNNNNGCCA |
| SEQ ID:26 | AK$_{UCCU}$ | UGGUCCGUAGCUCAGCCUGGUAGAGCGGCGGGCUUCCUCACCCGC<br>AGGUCGCGGGUUCAAAUCCCGCCGGACUAGCCA |
| SEQ ID:27 | PhΔAD | ATGGTTCATT GGGCCGATTA TATTGctgat aaaataatta gagagagggg<br>ggagaaggag aagtacgttg ttgagagtgg aataacgcca agtggttacg<br>ttcacgttgg gaactttagg gagcttttta cagcttatat tgtgggccat<br>gccctaaggg ataaggggta tgaggttagg cacatccaca tgtgggatga<br>ttatgataga tttaggaagg ttccaaggaa cgttcccccag gaatggaaag<br>attacctggg aatgcccatt agtgaagttc ctgatccctg gggatgccat<br>gagagttatg ctgaacactt catgagaaag ttcgaggagg aggtagaaaa<br>attagggatc gaagttgact ttctttatgc gagtgaactc tacaagagag<br>gggaatattc tgaggagata aggttagcct ttgagaaaag ggataagata<br>atggagatac taaacaagta tagggaaatt gcgaaacaac ctccccttcc<br>agagaactgg tggcccgcaa tggtttactg ccctgagcat aggagggaag<br>cagagatcat tgaatgggat ggggctgga aggttaagta taagtgcccc<br>gaaggtcacg agggatgggt tgatataagg agtgggaacg tgaaactgag<br>gtggcgtgtt gattggccca tgcgttggtc tcactttggc gttgacttcg<br>aacctgctgg aaaggatcat cttgtgctg gttcaagcta cgatacggga<br>aaggagatta taaaggaagt ttatggaaag gaagctccgt tatctttaat<br>gtatgagttt gttggaatta aggggcagaa ggggaagatg agtggtagta<br>agggaaatgt tatttactc agcgatctgt atgaggttct tgagccaggt<br>ctcgttagat ttatctacgc tcggcatagg ccaaacaagg agataaagat<br>agatctaggt cttggcattc taaacctcta cgatgagttc gataaagttg<br>agagaatata cttcgggggtt gagggtggta aaggtgatga tgaagaatta<br>aggaggactt acgagctttc gGTGATGCTG CCAACTTACT GA |
| SEQ ID:28 | PhΔAD.<br>pep | MVHWADYIAD KIIRERGEKE KYVVESGITP SGYVHVGNFR ELFTAYIVGH<br>ALRDKGYEVR HIHMWDDYDR FRKVPRNVPQ EWKDYLGMPI SEVPDPWGCH<br>ESYAEHFMRK FEEEVEKLGI EVDFLYASEL YKRGEYSEEI RLAFEKRDKI<br>MEILNKYREI AKQPPLPENW WPAMVYCPEH RREAEIIEWD GGWKVKYKCP<br>EGHEGWVDIR SGNVKLRWRV DWPMRWSHFG VDFEPAGKDH LVAGSSYDTG<br>KEIIKEVYGK EAPLSLMYEF VGIKGQKGKM SGSKGNVILL SDLYEVLEPG<br>LVRFIYARHR PNKEIKIDLG LGILNLYDEF DKVERIYFGV EGGKGDDEEL<br>RRTYELSVML PTY* |
| SEQ ID:29 | PhE444G<br>also known<br>as PhKRS | atggttcatt gggccgatta tattgctgat aaaataatta gagagagggg<br>ggagaaggag aagtacgttg ttgagagtgg aataacgcca agtggttacg<br>ttcacgttgg gaactttagg gagcttttta cagcttatat tgtgggccat<br>gccctaaggg ataaggggta tgaggttagg cacatccaca tgtgggatga<br>ttatgataga tttaggaagg ttccaaggaa cgttcccccag gaatggaaag<br>attacctggg aatgcccatt agtgaagttc ctgatccctg gggatgccat<br>gagagttatg ctgaacactt catgagaaag ttcgaggagg aggtagaaaa<br>attagggatc gaagttgact ttctttatgc gagtgaactc tacaagagag<br>gggaatattc tgaggagata aggttagcct ttgagaaaag ggataagata<br>atggagatac taaacaagta tagggaaatt gcgaaacaac ctccccttcc<br>agagaactgg tggcccgcaa tggtttactg ccctgagcat aggagggaag<br>cagagatcat tgaatgggat ggggctgga aggttaagta taagtgcccc<br>gaaggtcacg agggatgggt tgatataagg agtgggaacg tgaaactgag<br>gtggcgtgtt gattggccca tgcgttggtc tcactttggc gttgacttcg<br>aacctgctgg aaaggatcat cttgtgctg gttcaagcta cgatacggga<br>aaggagatta taaaggaagt ttatggaaag gaagctccgt tatctttaat<br>gtatgagttt gttggaatta aggggcagaa ggggaagatg agtggtagta<br>agggaaatgt tatttactc agcgatctgt atgaggttct tgagccaggt<br>ctcgttagat ttatctacgc tcggcatagg ccaaacaagg agataaagat<br>agatctaggt cttggcattc taaacctcta cgatgagttc gataaagttg<br>agagaatata cttcgggggtt gagggtggta aaggtgatga tgaagaatta<br>aggaggactt acgagctttc aatgcctaag aagcctgaga gattagtcgc<br>tcaagctcct tttaggttcc tagcggtgtt ggtcagtta ccgcatttaa<br>ccgaagaaga cataataaat gttctaatca aacagggaca tattcccagg<br>gatctatcca aggaggacgt tgagagggtt aaacttagga taaaccttgc<br>taggaattgg gttaaaaagt atgcccctga ggatgttaaa ttctcaatac<br>ttgagaaacc tcagaagtt gaggtaagtg gagatgttag ggaggccatg<br>aatgaggttg ctgagtggct tgagaatcat gaggaattta gcgttgaaga<br>gtttaataac attctattcg aagttgccaa gaggaggggg atatccagta<br>gggagtggtt ttcgacgctc tacagattat ttattggaaa ggaaagggga<br>ccgagattgg ccagtttcct ggcatctctt gataggagtt tcgttattaa<br>acgacttaga cttgagggat ag |

TABLE 1-continued

| SEQ ID: | Label | SEQUENCE |
|---|---|---|
| SEQ ID:30 | PhE444G.pep also known as PhKRS | MVHWADYIAD KIIRERGEKE KYVVESGITP SGYVHVGNFR ELFTAYIVGH<br>ALRDKGYEVR HIHMWDDYDR FRKVPRNVPQ EWKDYLGMPI SEVPDPWGCH<br>ESYAEHFMRK FEEEVEKLGI EVDPLYASEL YKRGEYSEEI RLAFEKRDKI<br>MEILNKYREI AKQPPLPENW WPAMVYCPEH RREAEIIEWD GGWKVKYKCP<br>EGHEGWVDIR SGNVKLRWRV DWPMRWSHFG VDFEPAGKDH LVAGSSYDTG<br>KEIIKEVYGK EAPLSLMYEF VGIKGQKGKM SGSKGNVILL SDLYEVLEPG<br>LVRFIYARHR PNKEIKIDLG LGILNLYDEF DKVERIYFGV EGGKGDDEEL<br>RRTYELSMPK KPERLVAQAP FRFLAVLVQL PHLTEEDIIN VLIKQGHIPR<br>DLSKEDVERV KLRINLARNW VKKYAPEDVK FSILEKPPEV EVSGDVREAM<br>NEVAEWLENH EEFSVEEFNN ILFEVAKRRG ISSREWFSTL YRLFIGKERG<br>PRLASFLASL DRSFVIKRLR LEG* |
| SEQ ID:31 | pACKO-A184TAG | gaactccgga tgagcattca tcaggcgggc aagaatgtga ataaaggccg<br>gataaaactt gtgcttattt ttctttacgg tctttaaaaa ggccgtaata<br>tccagctgaa cggtctggtt ataggtacat tgagcaactg actgaaatgc<br>ctcaaaatgt tctttacgat gccattggga tatatcaacg gtggtatatc<br>cagtgatttt tttctccatt ttagcttcct tagctcctga aaatctcgat<br>aactcaaaaa atacgcccgg tagtgatctt atttcattat ggtgaaagtt<br>ggaacctctt acgtgccgat caacgtctca ttttcgccaa aagttggccc<br>agggcttccc ggtatcaaca gggacaccag gatttattta ttctgcgaag<br>tgatcttccg tcacaggtat ttattcggcg caaagtgcgt cgggtgatgc<br>tgccaactta ctgatttagt gtatgatggt gttttgagg tgctccagtg<br>gcttctgttt ctatcagctg tccctcctgt tcagctactg acggggtggt<br>gcgtaacggc aaaagcaccg ccggacatca gcgctagcgg agtgtatact<br>ggcttactat gttggcactg atgagggtgt cagtgaagtg cttcatgtgg<br>caggagaaaa aaggctgcac cggtgcgtca gcagaatatg tgatacagga<br>tatattccgc ttcctcgctc actgactcgc tacgctcggt cgttcgactg<br>cggcgagcgg aaatggctta cgaacggggc ggagatttcc tggaagatgc<br>caggaagata cttaacaggg aagtgagagg gccgcggcaa agccgttttt<br>ccataggctc cgccccctg acaagcatca cgaaatctga cgctcaaatc<br>agtggtggcg aaacccgaca ggactataaa gataccaggc gtttcccct<br>ggcggctccc tcgtgcgctc tcctgttcct gcctttcggt ttaccggtgt<br>cattccgctg ttatggccgc gtttgtctca ttccacgcct gacactcagt<br>tccgggtagg cagttcgctc caagctggac tgtatgcacg aaccccccgt<br>tcagtccgac cgctgcgcct tatccggtaa ctatcgtctt gagtccaacc<br>cggaaagaca tgcaaaagca ccactggcag cagccactgg taattgattt<br>agaggagtta gtcttgaagt catgcgccgg ttaaggctaa actgaaagga<br>caagttttgg tgactgcgct cctccaagcc agttacctcg gttcaaagag<br>ttggtagctc agagaacctt cgaaaaaccg ccctgcaagg cggttttttc<br>gttttcagag caagagatta cgcgcagacc aaaacgatct caagaagatc<br>atcttattaa tcagataaaa tatttctaga tttcagtgca atttatctct<br>tcaaatgtag cacctgaagt cagcccata cgatataagt tgtaattctc<br>atgtttgaca gcttatcatc gataagcttt aatgcggtag tttatcacag<br>ttaaattgct aacgcagtca ggcaccgtgt atgaaatcta acaatgcgct<br>catcgtcatc ctcggcaccg tcacccctgga tgctgtaggc ataggcttgg<br>ttatgccggt actgccgggc ctcttgcggg atatcGGTTT CTTAGACGTC<br>AGGTGGCACT TTcggggaa atgtgcgcgg aaccccctatt tgtttatttt<br>tctaaataca ttcaaatatg tatccgctca tgagacataa accctgataa<br>atgcttcaat aatattgaaa aaggaagagt atgagtattc aacatttccg<br>tgtcgccctt attccttttt ttgcggcatt ttgccttcct gtttttgctc<br>acccagaaac gctggtgaaa gtaaaagatg ctgaagatca gttgggtgca<br>cgagtgggtt acatcgaact ggatctcaac agcggtaaga tccttgagag<br>ttttcgcccc gaagaacgtt ttccaatgat gagcacttt aaagttctgc<br>tatgtggcgc ggtattatcc cgtgttgacg ccgggcaaga gcaactcggt<br>cgccgcatac actattctca gaatgacttg gttgagtact caccagtcac<br>agaaaagcat cttacggatg gcatgacagt aagagaatta tgcagtgctg<br>ccataaccat gagtgataac actgcggcca acttacttct gacaacgatc<br>ggaggaccga aggagctaac cgcttttttg cacaacatgg gggatcatgt<br>aactcgcctt gatcgttggg aaccggagct gaatgaagcc ataccaaacg<br>acgagcgtga caccacgatg cctTAGgcaa tggcaacaac gttgcgcaaa<br>ctattaactg gcgaactact tactctagct tcccggcaac aattaataga<br>ctggatggag gcggataaag ttgcaggacc acttctgcgc tcggcccttc<br>cggctggctg gtttattgct gataaatctg gagccggtga gcgtgggtct<br>cgcggtatca ttgcagcact ggggccagat ggtaagccct cccgtatcgt<br>agttatctac acgacgggga gtcaggcaac tatggatgaa cgaaatagac<br>agatcgctga gataggtgcc tcactgatta gcattggca ccaccaccac<br>caccactaaC CCGGGACCAA GTTTACTCAT ATATActta gattgattta<br>aaacttcatt tttaatttaa aaggatctag gtgaagatcc ttttttgataa<br>tCTCATGACC AAAATCCCTT AACGgcatgc accattcctt gcggcggcgg<br>tgctcaacgg cctcaaccta ctactGGGCT GCTTCCTAAT GCAGGAGTCG<br>CATAAGGGAG AGCGTCTGGC GAAAGGGGGA TGTGCTGCAA GGCGATTAAG<br>TTGGGTAACG CCAGGGTTTT CCCAGTCACG ACGTTGTAAA ACGACGGCCA<br>GTGCCAAGCT TAAAAaaaat ccttagcctt cgctaaggat CTGCAGTTAT<br>AATCTCTTTC TAATTGGCTC TAAAATCTTT ATAAGTTCTT CAGCTACAGC<br>ATTTTTTAAA TCCATTGGAT GCAATTCCTT ATTTTTAAAT AAACTCTCTA<br>ACTCCTCATA GCTATTAACT GTCAAATCTC CACCAAATTT TTCTGGCCTT<br>TTTATGGTTA AAGGATATTC AAGGAAGTAT TTAGCTATCT CCATTATTGG |

TABLE 1-continued

| SEQ ID: | Label | SEQUENCE |
|---|---|---|
| | | ATTTCCTTCA ACAACTCCAG CTGGGCAGTA TGCTTTCTTT ATCTTAGCCC |
| | | TAATCTCTTC TGGAGAGTCA TCAACAGCTA TAAAATTCCC TTTTGAAGAA |
| | | CTCATCTTTC CTTCTCCATC CAAACCCGTT AAGACAGGGT TGTGAATACA |
| | | AACAACCTTT TTTGGTAAAA GCTCCCTTGC TAACATGTGT ATTTTTCTCT |
| | | GCTCCATCCC TCCAACTGCA ACATCAACGC CTAAATAATG AATATCATTA |
| | | ACCTGCATTA TTGGATAGAT AACTTCAGCA ACCTTTGGAT TTTCATCCTC |
| | | TCTTGCTATA AGTTCCATAC TCCTTCTTGC TCTTTTTAAG GTAGTTTTTA |
| | | AAGCCAATCT ATAGACATTC AGTGTATAAT CCTTATCAAG CTGGAATTCa |
| | | gcgttacaag tattacacaa agttttttat gttgagaata ttttttgat |
| | | ggggcgccac ttatttttga tcgttcgctc aaagAAGCGG CGCCAGGGNT |
| | | GTTTTTCTTT TCACCAGTNA GACGGGCAAC AGAACGCCAT Gagcggcctc |
| | | atttcttatt ctgagttaca acagtccgca ccgctgtccg gtagctcctt |
| | | ccggtgggcg cggggcatga ctatcgtcgc cgcacttatg actgtcttct |
| | | ttatcatgca actcgtagga caggtgccgg cagcgcccaa cagtcccccg |
| | | gccacggggc ctgccaccat acccacgccg aaacaagcgc cctgcaccat |
| | | tatgttccgg atctgcatcg caggatgctg ctggctaccc tgtggaacac |
| | | ctacatctgt attaacgaag cgctaaccgt ttttatcagg ctctgggagg |
| | | cagaataaat gatcatatcg tcaattatta cctccacggg gagagcctga |
| | | gcaaactggc ctcaggcatt tgagaagcac acggtcacac tgcttccggt |
| | | agtcaataaa ccggtaaacc agcaatagac ataagcggct atttaacgac |
| | | cctgccctga accgacgacc gggtcgaatt tgctttcgaa tttctgccat |
| | | tcatccgctt attatcactt attcaggcgt agcaccaggc gtttaagggc |
| | | accaataact gccttaaaaa aattacgccc cgccctgcca ctcatcgcag |
| | | tactgttgta attcattaag cattctgccg acatggaagc catcacagac |
| | | ggcatgatga acctgaatcg ccagcggcat cagcaccttg tcgccttgcg |
| | | tataatattt gcccatggtg aaaacggggg cgaagaagtt gtccatattg |
| | | gccacgttta aatcaaaact ggtgaaactc acccagggat tggctgagac |
| | | gaaaaacata ttctcaataa acccttaggg gaaataggcc aggttttcac |
| | | cgtaacacgc cacatcttgc gaatatatgt gtagaaactg ccggaaatcg |
| | | tcgtggtatt cactccagag cgatgaaaac gtttcagttt gctcatggaa |
| | | aacggtgtaa caagggtgaa cactatccca tatcaccagc tcaccgtctt |
| | | tcattgccat acg |
| SEQ ID:32 | pACKO-A184AGGA | gaactccgga tgagcattca tcaggcgggc aagaatgtga ataaaagccg |
| | | gataaaactt gtgcttattt tctttacggg tcttaaaaaa ggccgtaata |
| | | tccagctgaa cggtctggtt ataggtacat tgagcaactg actgaaatgc |
| | | ctcaaaatgt tctttacgat gccattggga tatatcaacg gtggtatatc |
| | | cagtgatttt tttctccatt ttagcttcct tagctcctga aaatctcgat |
| | | aactcaaaaa atacgcccgg tagtgatctt atttcattat ggtgaaagtt |
| | | ggaacctctt acgtgccgat caacgtctca ttttcgccaa aagttggccc |
| | | agggcttccc ggtatcaaca gggacaccag gatttattta ttctgcgaag |
| | | tgatcttccg tcacaggtat ttattcggcg caaagtgcgt cgggtgatgc |
| | | tgccaactta ctgatttagt gtatgatggt gttttttgagg tgctccagtg |
| | | gcttctgttt ctatcagctg tccctcctgt tcagctactg acggggtggt |
| | | gcgtaacggc aaaagcaccg ccggacatca gcgctagcgg agtgtatact |
| | | ggcttactat gttggcactg atgagggtgt cagtgaagtg cttcatgtgg |
| | | caggagaaaa aaggctgcac cggtgcgtca gcagaatatg tgatacagga |
| | | tatattccgc ttcctcgctc actgactcgc tacgctcggt cgttcgactg |
| | | cggcgagcgg aaatggctta cgaacggggc ggagatttcc tggaagatgc |
| | | caggaagata cttaacaggg aagtgagagg gccgcggcaa agccgttttt |
| | | ccataggctc cgcccccctg acaagcatca cgaaatctga cgctcaaatc |
| | | agtggtggcg aaacccgaca ggactataaa gataccaggc gtttccccct |
| | | ggcggctccc tcgtgcgctc tcctgttcct gcctttcggt ttaccggtgt |
| | | cattccgctg ttatggccgc gtttgtctca ttccacgcct gacactcagt |
| | | tccgggtagg cagttcgctc caagctggac tgtatgcacg aaccccccgt |
| | | tcagtccgac cgctgcgcct tatccggtaa ctatcgtctt gagtccaacc |
| | | cggaaagaca tgcaaaagca ccactggcag cagccactgg taattgattt |
| | | agaggagtta gtcttgaagt catgcgccgg ttaaggctaa actgaaagga |
| | | caagttttgg tgactgcgct cctccaagcc agttacctcg gttcaaagag |
| | | ttggtagctc agagaacctt cgaaaaaccg ccctgcaagg cggttttttc |
| | | gttttcagag caagagatta cgcgcagacc aaaacgatct caagaagatc |
| | | atcttattaa tcagataaaa tatttctaga tttcagtgca atttatctct |
| | | tcaaatgtag cacctgaagt cagccccata cgatataagt tgtaattctc |
| | | atgtttgaca gcttatcatc gataagcttt aatgcggtag tttatcacag |
| | | ttaaattgct aacgcagtca ggcaccgtgt atgaaatcta acaatgcgct |
| | | catcgtcatc ctcggcaccg tcacccctgga tgctgtaggc ataggcttgg |
| | | ttatgccggt actgccgggc ctcttgcggg atatcGGTTT CTTAGACGTC |
| | | AGGTGGCACT TTtcggggaa atgtgcgcgg aaccccctatt tgtttatttt |
| | | tctaaataca ttcaaatatg tatccgctca tgagacaata accctgataa |
| | | atgcttcaat aatattgaaa aaggaagagt atgagtattc aacatttccg |
| | | tgtcgccctt attcccttttt tgcggcatt ttgccttcct gttttttgctc |
| | | acccagaaac gctggtgaaa gtaaaagatg ctgaagatca gttgggtgca |
| | | cgagtgggtt acatcgaact ggatctcaac agcggtaaga tccttgagag |
| | | ttttcgcccc gaagaacgtt ttccaatgat gagcactttt aaagttctgc |
| | | tatgtggcgc ggtattatcc cgtgttgacg ccgggcaaga gcaactcggt |
| | | cgccgcatac actattctca gaatgacttg gttgagtact caccagtcac |
| | | agaaaagcat cttacggatg gcatgacagt aagagaatta tgcagtgctg |

TABLE 1-continued

| SEQ ID: | Label | SEQUENCE |
|---|---|---|
| | | ccataaccat gagtgataac actgcggcca acttacttct gacaacgatc |
| | | ggaggaccga aggagctaac cgcttttttg cacaacatgg gggatcatgt |
| | | aactcgcctt gatcgttggg aaccggagct gaatgaagcc ataccaaacg |
| | | acgagcgtga caccacgatg cctAGGAgca atggcaacaa cgttgcgcaa |
| | | actattaact ggcgaactac ttactctagc ttcccggcaa caattaatag |
| | | actggatgga ggcggataaa gttgcaggac cacttctgcg ctcggccctt |
| | | ccggctggct ggtttattgc tgataaatct ggagccggtg agcgtgggtc |
| | | tcgcggtatc attgcagcac tggggccaga tggtaagccc tcccgtatcg |
| | | tagttatcta cacgacgggg agtcaggcaa ctatggatga acgaaataga |
| | | cagatcgctg agataggtgc ctcactgatt aagcattggc accaccacca |
| | | ccaccactaa CCCGGGACCA AGTTTACTCA TATATACttt agattgattt |
| | | aaaacttcat ttttaattta aaaggatcta ggtgaagatc cttttttgata |
| | | atCTCATGAC CAAAATCCCT TAACGgcatg caccattcct tgcggcggcg |
| | | gtgctcaacg gcctcaacct actactGGGC TGCTTCCTAA TGCAGGAGTC |
| | | GCATAAGGGA GAGCGTCTGG CGAAAGGGGG ATGTGCTGCA AGGCGATTAA |
| | | GTTGGGTAAC GCCAGGGTTT TCCCAGTCAC GACGTTGTAA AACGACGGCC |
| | | AGTGCCAAGC TTAAAAAaaa tccttagctt tcgctaagga tCTGCAGTTA |
| | | TAATCTCTTT CTAATTGGCT CTAAAATCTT TATAAGTTCT TCAGCTACAG |
| | | CATTTTTTAA ATCCATTGGA TGCAATTCCT TATTTTTAAA TAAACTCTCT |
| | | AACTCCTCAT AGCTATTAAC TGTCAAATCT CCACCAAATT TTTCTGGCCT |
| | | TTTTATGGTT AAAGGATATT CAAGGAAGTA TTTAGCTATC TCCATTATTG |
| | | GATTTCCTTC AACAACTCCA GCTGGGCAGT ATGCTTTCTT TATCTTAGCC |
| | | CTAATCTCTT CTGGAGAGTC ATCAACAGCT ATAAAATTCC CTTTTGAAGA |
| | | ACTCATCTTT CCTTCTCCAT CCAAACCCGT TAAGACAGGG TTGTGAATAC |
| | | AAACAACCTT TTTTGGTAAA AGCTCCCTTG CTAACATGTG TATTTTTCTC |
| | | TGCTCCATCC CTCCAACTGC AACATCAACG CCTAAATAAT GAATATCATT |
| | | AACCTGCATT ATTGGATAGA TAACTTCAGC AACCTTTGGA TTTTCATCCT |
| | | CTCTTGCTAT AAGTTCCATA CTCCTTCTTG CTCTTTTTAA GGTAGTTTTT |
| | | AAAGCCAATC TATAGACATT CAGTGTATAA TCCTTATCAA GCTGGAATTC |
| | | agcgttacaa gtattacaca aagtttttta tgttgagaat attttttga |
| | | tggggcgcca cttattttg atcgttcgct caaagAAGCG GCGCCAGGGN |
| | | TGTTTTTCTT TTCACCAGTN AGACGGGCAA CAGAACGCCA TGAgcggcct |
| | | catttcttat tctgagttac aacagtccgc accgctgtcc ggtagctcct |
| | | tccggtgggc gcggggcatg actatcgtcg ccgcacttat gactgtcttc |
| | | tttatcatgc aactcgtagg acaggtgccg gcagcgccca acagtccccc |
| | | ggccacgggg cctgccacca tacccacgcc gaaacaagcg ccctgcacca |
| | | ttatgttccg gatctgcatc gcaggatgct gctggctacc ctgtggaaca |
| | | cctacatctg tattaacgaa gcgctaaccg tttttatcag gctctgggag |
| | | gcagaataaa tgatcatatc gtcaattatt acctccacgg ggagagcctg |
| | | agcaaactgg cctcaggcat ttgagaagca cacggtcaca ctgcttccgg |
| | | tagtcaataa accggtaaac cagcaataga cataagcggc tatttaacga |
| | | ccctgccctg aaccgacgac cgggtcgaat ttgctttcga atttctgcca |
| | | ttcatccgct tattatcact tattcaggcg tagcaccagg cgtttaaggg |
| | | caccaataac tgccttaaaa aaattacgcc ccgccctgcc actcatcgca |
| | | gtactgttgt aattcattaa gcattctgcc gacatggaag ccatcacaga |
| | | cggcatgatg aacctgaatc gccagcggca tcagcacctt gtcgccttgc |
| | | gtataatatt tgcccatggt gaaaacgggg gcgaagaagt tgtccatatt |
| | | ggccacgttt aaatcaaaac tggtgaaact cacccaggga ttggctgaga |
| | | cgaaaaacat attctcaata aacccttttag ggaaataggc caggttttca |
| | | ccgtaacacg ccacatcttg cgaatatatg tgtagaaact gccggaaatc |
| | | gtcgtggtat tcactccaga gcgatgaaaa cgtttcagtt tgctcatgga |
| | | aaacggtgta acaagggtga acactatccc atatcaccag ctcaccgtct |
| | | ttcattgcca tacg |
| SEQ ID:33 | pACKO-Bla | gaactccgga tgagcattca tcaggcgggc aagaatgtga ataaaggccg |
| | | gataaaactt gtgcttattt ttctttacgg tctttaaaaa ggccgtaata |
| | | tccagctgaa cggtctggtt ataggtacat tgagcaactg actgaaatgc |
| | | ctcaaaatgt tctttacgat gccattggga tatatcaacg gtggtatatc |
| | | cagtgatttt tttctccatt ttagcttcct tagctcctga aaatctcgat |
| | | aactcaaaaa atacgcccgg tagtgatctt atttcattat ggtgaaagtt |
| | | ggaacctctt acgtgccgat caacgtctca ttttcgccaa aagttggccc |
| | | agggcttccc ggtatcaaca gggacaccag gatttattta ttctgcgaag |
| | | tgatcttccg tcacaggtat ttattcggcg caaagtgcgt cgggtgatgc |
| | | tgccaactta ctgatttagt gtatgatggt gttttttgagg tgctccagtg |
| | | gcttctgttt ctatcagctg tccctcctgt tcagctactg acggggtggt |
| | | gcgtaacggc aaaagcaccg ccggacatca gcgctagcgg agtgtatact |
| | | ggcttactat gttggcactg atgagggtgt cagtgaagtg cttcatgtgg |
| | | caggagaaaa aaggctgcac cggtgcgtca gcagaatatg tgatacagga |
| | | tatattccgc ttcctcgctc actgactcgc tacgctcggt cgttcgactg |
| | | cggcgagcgg aaatggctta cgaacggggc ggagatttcc tggaagatgc |
| | | caggaagata cttaacaggg aagtgagagg gccgcggcaa agccgttttt |
| | | ccataggctc cgcccccctg acaagcatca cgaaatctga cgctcaaatc |
| | | agtggtggcg aaacccgaca ggactataaa gataccaggc gtttccccct |
| | | ggcggctccc tcgtgcgctc tcctgttcct gcctttcggt ttaccggtgt |
| | | cattccgctg ttatggccgc gtttgtctca ttccacgcct gacactcagt |
| | | tccgggtagg cagttcgctc caagctggac tgtatgcacg aaccccccgt |
| | | tcagtccgac cgctgcgcct tatccggtaa ctatcgtctt gagtccaacc |

TABLE 1-continued

| SEQ ID: | Label | SEQUENCE |
|---|---|---|
| | | cggaaagaca tgcaaaagca ccactggcag cagccactgg taattgattt |
| | | agaggagtta gtcttgaagt catgcgccgg ttaaggctaa actgaaagga |
| | | caagttttgg tgactgcgct cctccaagcc agttacctcg gttcaaagag |
| | | ttggtagctc agagaacctt cgaaaaaccg ccctgcaagg cggttttttc |
| | | gttttcagag caagagatta cgcgcagacc aaaacgatct caagaagatc |
| | | atcttattaa tcagataaaa tatttctaga tttcagtgca atttatctct |
| | | tcaaatgtag cacctgaagt cagccccata cgatataagt tgtaattctc |
| | | atgtttgaca gcttatcatc gataagcttt aatgcggtag tttatcacag |
| | | ttaaattgct aacgcagtca ggcaccgtgt atgaaatcta acaatgcgct |
| | | catcgtcatc ctcggcaccg tcaccctgga tgctgtaggc ataggcttgg |
| | | ttatgccggt actgccgggc ctcttgcggg atatcGGTTT CTTAGACGTC |
| | | AGGTGGCact tttcggggaa atgtgcgcgg aacccctatt tgtttatttt |
| | | tctaaataca ttcaaatatg tatccgctca tgagacaata accctgataa |
| | | atgcttcaat aatattgaaa aaggaagagt atgagtattc aacatttccg |
| | | tgtcgccctt attcccttt ttgcggcatt ttgccttccT GTTTTTGCTC |
| | | ACCCAGAAAC ACTAGtgcag caatggcaac aacgttgcgc aaactattaa |
| | | ctggcgaact acttactcta gcttcccggc aacaattaat agactggatg |
| | | gaggcggata aagttgcagg accacttctg cgctcggccc ttccggctgg |
| | | ctggtttatt gctgataaat ctggagccgg tgagcgtggg tctcgcggta |
| | | tcattgcagc actggggcca gatggtaagc cctcccgtat cgtagttatc |
| | | tacacgacgg ggagtcaggc aactatggat gaacgaaata gacagatcgc |
| | | tgagataggt gcctCACTGA TTAAGCATTG GTAACCCGGG ACCAAGTTTA |
| | | CTCATATATA Ctttagattg atttaaaact tcatttttaa tttaaaagga |
| | | tctaggtgaa gatccttttt gataatCTCA TGACCAAAAT CCCTTAACGg |
| | | catgcaccat tccttgcggc ggcggtgctc aacggcctca acctactact |
| | | GGGCTGCTTc CTAATGCAGG AGTCGCATAA GGGAGAGCGT CTGGCGAAAG |
| | | GGGGATGTGC TGCAAGGCGA TTAAGTTGGG TAACGCCAGG GTTTTCCCAG |
| | | TCACGACGTT GTAAAACGAC GGCCAGTGCC AAGCTTAAAA Aaaatcctta |
| | | gctttcgcta aggatCTGCA GTTATAATCT CTTTCTAATT GGCTCTAAAA |
| | | TCTTTATAAG TTCTTCAGCT ACAGCATTTT TTAAATCCAT TGGATGCAAT |
| | | TCCTTATTTT TAAATAAACT CTCTAACTCC TCATAGCTAT TAACTGTCAA |
| | | ATCTCCACCA AATTTTTCTG GCCTTTTTAT GGTTAAAGGA TATTCAAGGA |
| | | AGTATTTAGC TATCTCCATT ATTGGATTTC CTTCAACAAC TCCAGCTGGG |
| | | CAGTATGCTT TCTTTATCTT AGCCCTAATC TCTTCTGGAG AGTCATCAAC |
| | | AGCTATAAAA TTCCCTTTTG AAGAACTCAT CTTTCCTTCT CCATCCAAAC |
| | | CCGTTAAGAC AGGGTTGTGA ATACAAACAA CCTTTTTTGG TAAAAGCTCC |
| | | CTTGCTAACA TGTGTATTTT TCTCTGCTCC ATCCCTCCAA CTGCAACATC |
| | | AACGCCTAAA TAATGAATAT CATTAACCTG CATTATTGGA TAGATAACTT |
| | | CAGCAACCTT TGGATTTTCA TCCTCTCTTG CTATAAGTTC CATACTCCTT |
| | | CTTGCTCTTT TAAGGTAGT TTTTAAAGCC AATCTATAGA CATTCAGTGT |
| | | ATAATCCTTA TCAAGCTGGA ATTCagcgtt acaagtatta cacaaagttt |
| | | tttatgttga gaatatttt ttgatggggc gccacttatt tttgatcgtt |
| | | cgctcaaagA AGCGGCGCCA GGGNTGTTTT TCTTTTCACC AGTNAGACGG |
| | | GCAACAGAAC GCCATGAgcg gcctcatttc ttattctgag ttacaacagt |
| | | ccgcaccgct gtccggtagc tccttccggt gggcgcgggg catgactatc |
| | | gtcgccgcac ttatgactgt cttctttatc atgcaactcg taggacaggt |
| | | gccggcagcg cccaacagtc ccccggccac ggggcctgcc accatacccca |
| | | cgccgaaaca agcgccctgc accattatgt tccggatctg catcgcagga |
| | | tgctgctggc taccctgtgg aacacctaca tctgtattaa cgaagcgcta |
| | | accgttttta tcaggctctg ggaggcagaa taaatgatca tatcgtcaat |
| | | tattacctcc acggggagag cctgagcaaa ctggcctcag gcatttgaga |
| | | agcacacggt cacactgctt ccggtagtca ataaaccggt aaaccagcaa |
| | | tagacataag cggctattta acgaccctgc cctgaaccga cgaccgggtc |
| | | gaatttgctt tcgaatttct gccattcatc cgcttattat cacttattca |
| | | ggcgtagcac caggcgttta agggcaccaa taactgcctt aaaaaaatta |
| | | cgccccgccc tgccactcat cgcagtactg ttgtaattca ttaagcattc |
| | | tgccgacatg gaagccatca cagacggcat gatgaacctg aatcgccagc |
| | | ggcatcagca ccttgtcgcc ttgcgtataa tatttgccca tggtgaaaac |
| | | ggggcgaag aagttgtcca tattggccac gtttaaatca aaactggtga |
| | | aactcaccca gggattggct gagacgaaaa acatattctc aataaaccct |
| | | ttagggaaat aggccaggtt ttcaccgtaa cacgccacat cttgcgaata |
| | | tatgtgtaga aactgccgga aatcgtcgtg gtattcactc cagagcgatg |
| | | aaaacgtttc agtttgctca tggaaaacgg tgtaacaagg gtgaacacta |
| | | tcccatatca ccagctcacc gtctttcatt gccatacg |
| SEQ ID:34 | pKQ | ATGGATCCGA GCTCGAGATC TGCAGCTGGT ACCATATGGG AATTCGAAGC |
| | | TTGGGCCCGA ACAAAAACTC ATCTCAGAAG AGGATCTGAA TAGCGCCGTC |
| | | GACCATCATC ATCATCATCA TTGAGTTTAA ACGGTCTCCA GCTTGGCTGT |
| | | TTTGGCGGAT GAGAGAAGAT TTTCAGCCTG ATACAGATTA AATCAGAACG |
| | | CAGAAGCGGT CTGATAAAAC AGAATTTGCC TGGCGGCAGT AGCGCGGTGG |
| | | TCCCACCTGA CCCCATGCCG AACTCAGAAG TGAAACGCCG TAGCGCCGAT |
| | | GGTAGTGTGG GGTCTCCCCA TGCGAGAGTA GGGAACTGCC AGGCATCAAA |
| | | TAAAACGAAA GGCTCAGTCG AAAGACTGGG CCTTTCGTTT TATCTGTTGT |
| | | TTGTCGGTGA ACGATATCTG CTTTTCTTCG CGAATtaatt ccgcttcgca |
| | | ACATGTgagc aaaaggccag caaaaggcca ggaaccgtaa aaaggccgcg |
| | | ttgctggcgt ttttccatag gctccgcccc cctgacgagc atcacaaaaa |
| | | tcgacgctca agtcagaggt ggcgaaaccc gacaggacta taaagatacc |

TABLE 1-continued

| SEQ ID: | Label | SEQUENCE |
|---|---|---|
| | | aggcgtttcc ccctggaagc tccctcgtgc gctctcctgt tccgaccctg<br>ccgcttaccg gatacctgtc cgcctttctc ccttcgggaa gcgtggcgct<br>ttctcatagc tcacgctgta ggtatctcag ttcggtgtag gtcgttcgct<br>ccaagctggg ctgtgtgcac gaacccccg ttcagcccga ccgctgcgcc<br>ttatccggta actatcgtct tgagtccaac ccggtaagac acgacttatc<br>gccactggca gcagccactg gtaacaggat tagcagagcg aggtatgtag<br>gcggtgctac agagttcttg aagtggtggc ctaactacgg ctacactaga<br>aggacagtat ttggtatctg cgctctgctg aagccagtta ccttcggaaa<br>aagagttggt agctcttgat ccggcaaaca aaccaccgct ggtagcggtg<br>gtttttttgt ttgcaagcag cagattacgc gcagaaaaaa aggatctcaa<br>gaagatcctt tgatcttttc tacggggtct gacgctcagt ggaacgaaaa<br>ctcacgttaa gggatttggg TCATGAgttg tgtctcaaaa tctctgatgt<br>tacattgcac aagataaaaa tatatcatca tgaacaataa aactgtctgc<br>ttacataaac agtaatacaa ggggtgttat gagccatatt caacgggaaa<br>cgtcttgctc gaggccgcga ttaaattcca acatggatgc tgatttatat<br>gggtataaat gggctcgcga taatgtcggg caatcaggtg cgacaatcta<br>tcgattgtat gggaagcccg atgcgccaga gttgtttctg aaacatggca<br>aaggtagcgt tgccaatgat gttacagatg agatggtcag actaaactgg<br>ctgacggaat ttatgcctct tccgaccatc aagcatttta tccgtactcc<br>tgatgatgca tggttactca ccactgcgat ccccgggaaa acagcattcc<br>aggtattaga agaatatcct gattcaggtg aaaatattgt tgatgcgctg<br>gcagtgttcc tgcgccggtt gcattcgatt cctgtttgta attgtccttt<br>taacagcgat cgcgtatttc gtctcgctca ggcgcaatca cgaatgaata<br>acggtttggt tgatgcgagt gattttgatg acgagcgtaa tggctggcct<br>gttgaacaag tctggaaaga aatgcataag cttttgccat tctcaccgga<br>ttcagtcgtc actcatggtg atttctcact tgataacctt atttttgacg<br>aggggaaatt aataggttgt attgatgttg gacgagtcgg aatcgcagac<br>cgataccagg atcttgccat cctatggaac tgcctcggtg agttttctcc<br>ttcattacag aaacggcttt tcaaaaata tggtattgat aatcctgata<br>tgaataaatt gcagtttcat ttgatgctcg atgagttttt ctaatcagaa<br>ttggttaatt ggttgtaaca ctggcagagc attacgctga cttgacggga<br>cggcggcttt gttgaataaa tcgaacttt gctgagttga aggatcCTCG<br>GGagttgtca gcctgtcccg cttataagat catacgccgt tatacGTTGT<br>TTACGCTTTG AGGAATTAAC C |
| SEQ ID:35 | pKQ-<br>PhKep | ATGGTTCATT GGGCCGATTA TATTGctgat aaaataatta gagagagggg<br>ggagaaggag aagtacgttg ttgagagtgg aataacgcca agtggttacg<br>ttcacgttgg gaactttagg gagcttttta cagcttatat tgtgggccat<br>gccctaaggg ataaggggta tgaggttagg cacatccaca tgtgggatga<br>ttatgataga tttaggaagg ttccaaggaa cgttccccag gaatggaaag<br>attacctggg aatgcccatt agtgaagttc ctgatccctg gggatgccat<br>gagagttatg ctgaacactt catgagaaag ttcgaggagg aggtagaaaa<br>attagggatc gaagttgact tctttatgc gagtgaactc tacaagagag<br>gggaatattc tgaggagata aggttagcct ttgagaaaag ggataagata<br>atggagatac taaacaagta tagggaaatt gcgaaacaac ctcccttcc<br>agagaactgg tggcccgcaa tggtttactg ccctgagcat aggagggaag<br>cagagatcat tgaatgggat ggggctgga aggttaagta taagtgcccc<br>gaaggtcacg agggatgggt tgatataagg agtgggaacg tgaaactgag<br>gtggcgtgtt gattggccca tgcgttggtc tcactttggc gttgacttcg<br>aacctgctgg aaaggatcat cttgtggctg gttcaagcta cgatacggga<br>aaggagatta taaaggaagt ttatggaaag gaagctccgt tatctttaat<br>gtatgagttt gttggaatta aggggcagaa gggggaagatg agtggtagta<br>agggaaatgt tatttactc agcgatctgt atgaggttct tgagccaggt<br>ctcgttagat ttatctacgc tcggcatagg ccaaacaagg agataaagat<br>agatctaggt cttggcattc taaacctcta cgatgagttc gataaagttg<br>agagaatata cttcgggggtt gagggtggta aaggtgatga tgaagaatta<br>aggaggactt acgagcttc ggtgatgctg ccaacttact gatttagtgt<br>atgatggtgt ttttgaggtg ctccagtggc ttctgtttct atcagctgtc<br>cctcctgttc agctactgac ggggtggtgc gtaacggcaa aagcaccgcc<br>ggacatcagc gctatctctg ctctcactgc cgtaaaacat ggcaactgca<br>gttcacttac accgcttctc aacccggtac gcaccagaaa atcattgata<br>tggccatgaa tggcgttgga tgccgggcaa ccgcccgcat tatgggcgtt<br>ggcctcaaca cgattttccg ccatttaaaa aactcaggcc gcagtcggta<br>acctcgcgca tacagccggg cagtgacgtc atcgtctgcg cggaaatgga<br>cgaacagtgg ggatacgtcg gtgctaaatc gcgccagcgc tggctgtttt<br>acgcgtatga caggctccgg aagacggttg ttgcgcacgt attcggtgaa<br>cgcactatgg cgacgctggg gcgtcttatg agcctgctgt cacccttga<br>cgtggtgata tggatgacgg atggctggcc gctgtatgaa tcccgcctga<br>agggaaagct gcacgtaatc agcaagcgat atacgcagcg aattgagcgg<br>cataacctga atctgaggca gcacctggca cggctgggac ggaagtcgct<br>gtcgttctca aaatcggtgg agctgcatga caaagtcatc gggcattatc<br>tgaacataaa acactatcaa taagttggag tcattacccc gagctttcaa<br>tgcctaagaa gctgagaga ttagtcgctc aagctccttt taggttccta<br>gcggtgttgg ttcagttacc gcatttaacc gaagaagaca taataaatgt<br>tctaatcaaa caggacata ttccaggga tctatccaag gaggacgttg<br>agagggttaa acttaggata aaccttgcta ggaattgggt taaaaagtat<br>gccctgagg atgttaaatt ctcaatactt gagaaacctc cagaagttga |

TABLE 1-continued

| SEQ ID: | Label | SEQUENCE |
|---|---|---|
| | | ggtaagtgaa gatgttaggg aggccatgaa tgaggttgct gagtggcttg
agaatcatga ggaatttagc gttgaagagt ttaataacat tctattcgaa
gttgccaaga ggaggggat atccagtagg gagtggtttt cgacgctcta
cagattattt attggaaagg aaaggggacc gagattggcc agtttcctgg
catctcttga taggagtttc gttattAAAC GACTTAGACT TGAGGGATAA
GAATTCGAAG CTTGGGCCCG AACAAAAACT CATCTCAGAA GAGGATCTGA
ATAGCGCCGT CGACCATCAT CATCATCATC ATTGAGTTTA AACGGTCTCC
AGCTTGGCTG TTTTGGCGGA TGAGAGAAGA TTTTCAGCCT GATACAGATT
AAATCAGAAC GCAGAAGCGG TCTGATAAAA CAGAATTTGC CTGGCGGCAG
TAGCGCGGTG GTCCCACCTG ACCCCATGCC GAACTCAGAA GTGAAACGCC
GTAGCGCCGA TGGTAGTGTG GGGTCTCCCC ATGCGAGAGT AGGGAACTGC
CAGGCATCAA ATAAAACGAA AGGCTCAGTC GAAAGACTGG GCCTTTCGTT
TTATCTGTTG TTTGTCGGTG AACGATATCT GCTTTTCTTC GCGAATtaat
tccgcttcgc aACATGTgag caaaaggcca gcaaaaggcc aggaaccgta
aaaaggccgc gttgctggcg ttttttccata ggctccgccc ccctgacgag
catcacaaaa atcgacgctc aagtcagagg tggcgaaacc cgacaggact
ataaagatac caggcgtttc ccctggaag ctcccctgtg cgctctcctg
ttccgaccct gccgcttacc ggatacctgt ccgcctttct cccttcggga
agcgtggcgc tttctcatag ctcacgctgt aggtatctca gttcggtgta
ggtcgttcgc tccaagctgg gctgtgtgca cgaaccccccc gttcagcccg
accgctgcgc cttatccggt aactatcgtc ttgagtccaa cccggtaaga
cacgacttat cgccactggc agcagccact ggtaacagga ttagcagagc
gaggtatgta ggcggtgcta cagagttctt gaagtggtgg cctaactacg
gctacactag aaggacagta tttggtatct gcgctctgct gaagccagtt
accttcggaa aaagagttgg tagctcttga tccggcaaac aaaccaccgc
tggtagcggt ggttttttg tttgcaagca gcagattacg cgcagaaaaa
aaggatctca agaagatcct ttgatctttt ctacggggtc tgacgctcag
tggaacgaaa actcacgtta agggattttg gTCATGAgtt gtgtctcaaa
atctctgatg ttacattgca caagataaaa atatatcatc atgaacaata
aaactgtctg cttacataaa cagtaataca aggggtgtta tgagccatat
tcaacgggaa acgtcttgct cgaggccgcg attaaattcc aacatggatg
ctgatttata tgggtataaa tgggctcgcg ataatgtcgg gcaatcaggt
gcgacaatct atcgattgta tgggaagccc gatgcgccag agttgtttct
gaaacatggc aaaggtagcg ttgccaatga tgttacagat gagatggtca
gactaaactg gctgacggaa tttatgcctc ttccgaccat caagcatttt
atccgtactc ctgatgatgc atggttactc accactgcga tccccgggaa
aacagcattc caggtattag aagaatatcc tgattcaggt gaaaatattg
ttgatgcgct ggcagtgttc ctgcgccggt tgcattcgat tcctgtttgt
aattgtcctt ttaacagcga tcgcgtattt cgtctcgctc aggcgcaatc
acgaatgaat aacggtttgg ttgatgcgag tgattttgat gacgagcgta
atggctggcc tgttaacaa gtctggaaag aaatgcataa gcttttgcca
ttctcaccgg attcagtcgt cactcatggt gatttctcac ttgataacct
tattttgac gaggggaaat taataggttg tattgatgtt ggacgagtcg
gaatcgcaga ccgataccag gatcttgcca tcctatggaa ctgcctcggt
gagttttctc cttcattaca gaaacggctt tttcaaaaat atggtattga
taatcctgat atgaataaat tgcagtttca tttgatgctc gatgagtttt
tctaatcaga attggttaat tggttgtaac actggcagag cattacgctg
acttgacggg acggcggctt tgttgaataa atcgaacttt tgctgagttg
aaggatcCTC GGGagttgtc agcctgtccc gcttataaga tcatacgccg
ttatacGTTG TTTACGCTTT GAGGAATTAA CC |

What is claimed is:

1. A translation system comprising:
an orthogonal lysyl tRNA (lysyl O-tRNA);
an orthogonal aminoacyl tRNA synthetase (O-RS) that preferentially charges the orthogonal lysyl tRNA with homoglutamine; or
the orthogonal lysyl tRNA (lysyl O-tRNA) and the orthogonal aminoacyl tRNA synthetase (O-RS);
wherein the O-RS is PhΔAD (SEQ ID NO: 28), or an O-RS comprising at least 95% identity to PhΔAD (SEQ ID NO: 28) further comprising an isoleucine at a position corresponding to position 41 and a serine at a position corresponding to position 268;
and wherein the lysyl O-tRNA comprises an anti-codon loop comprising a CU(X)$_n$XXXAA sequence and at least 95% identity to SEQ ID NO: 26, wherein n is an integer, and
wherein the O-RS in combination with the O-tRNA of SEQ ID NO: 26 and homoglutamine is at least 50% as effective at suppressing a selector codon as an I41 and S268 mutant of PhΔAD (SEQ ID NO: 28; a mutant of *Pyrococcus horikoshii* tRNA synthetase), in combination with an O-tRNA of SEQ ID NO: 26 and homoglutamine.

2. The translation system of claim 1, wherein the translation system comprises a cell.

3. The translation system of claim 2, wherein the cell is an *E. coli* cell.

4. The translation system of claim 1, wherein the lysyl O-tRNA or modified variant thereof, the O-RS, or both, are derived from an archaebacterium or from *Pyrococcus horikoshii* (PhKRS).

5. The translation system of claim 4, wherein the O-RS, when expressed in an *E. coli* cell displays a toxicity that is the same as or less than an I41 and/or S268 mutant of PhΔAD (SEQ ID NO:28).

6. The translation system of claim 1, wherein the lysyl O-tRNA comprises a recognition sequence for a four base codon or an amber codon.

7. The translation system of claim 1, wherein the lysyl O-tRNA or comprises a recognition sequence for AGGA.

8. The translation system of claim 1, wherein the CU(X)$_n$XXXAA sequence comprises CUCUAAA or CUUCCUAA.

9. The translation system of claim 1, comprising an additional O-RS and an additional O-tRNA, wherein the additional O-RS and the additional O-tRNA suppress a frame shift selector codon that is different from a frame shift selector codon suppressed by the lysyl O-tRNA and the O-RS that preferentially charges the lysyl O-tRNA.

10. The translation system of claim 1, wherein the translation system suppresses both a four base selector codon and a stop selector codon in a target nucleic acid that encodes a target polypeptide.

11. The translation system of claim 10, wherein the four base selector codon comprises the sequence AGGA and the stop selector codon comprises the sequence TAG or UAG.

12. The translation system of claim 1, comprising a target nucleic acid that comprises a four base selector codon.

13. The translation system of claim 12, comprising a protein encoded by the target nucleic acid.

14. The translation system of claim 1, comprising a target nucleic acid that comprises a four base selector codon and a stop selector codon.

15. The translation system of claim 14, comprising a protein encoded by the target nucleic acid, wherein the protein comprises at least two different unnatural amino acids.

* * * * *

UNITED STATES PATENT AND TRADEMARK OFFICE
CERTIFICATE OF CORRECTION

PATENT NO. : 7,638,297 B2
APPLICATION NO. : 10/563686
DATED : December 29, 2009
INVENTOR(S) : J. Christopher Anderson et al.

It is certified that error appears in the above-identified patent and that said Letters Patent is hereby corrected as shown below:

Col. 1 line 18-20 please delete paragraph 0002, "STATEMENT AS TO RIGHTS TO INVENTIONS MADE UNDER FEDERALLY SPONSORED RESEARCH AND DEVELOPMENT", and replace it with the following paragraph:

This invention was made with government support under grant number GM62159 from the National Institutes of Health, and grant number ER45812 from the Department of Energy. The United States Government has certain rights in this invention.

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,638,297 B2  Page 1 of 1
APPLICATION NO. : 10/563686
DATED : December 29, 2009
INVENTOR(S) : Anderson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 337 days.

Signed and Sealed this

Ninth Day of November, 2010

David J. Kappos
*Director of the United States Patent and Trademark Office*